(12) United States Patent
Selby et al.

(10) Patent No.: US 10,913,719 B2
(45) Date of Patent: Feb. 9, 2021

(54) INTERMEDIATES TO PREPARE PYRIDAZINONE HERBICIDES, AND A PROCESS TO PREPARE THEM

(71) Applicant: FMC Corporation, Philadelphia, PA (US)

(72) Inventors: Thomas Paul Selby, Hockessin, DE (US); Kanu Maganbhai Patel, Sugarland, TX (US); Thomas Martin Stevenson, Newark, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/771,896

(22) PCT Filed: Oct. 26, 2016

(86) PCT No.: PCT/US2016/058755
§ 371 (c)(1),
(2) Date: Apr. 27, 2018

(87) PCT Pub. No.: WO2017/074988
PCT Pub. Date: May 4, 2017

(65) Prior Publication Data
US 2018/0312467 A1  Nov. 1, 2018

Related U.S. Application Data

(60) Provisional application No. 62/247,438, filed on Oct. 28, 2015.

(51) Int. Cl.
*C07D 405/14* (2006.01)
*C07D 401/12* (2006.01)
(Continued)

(52) U.S. Cl.
CPC ........... *C07D 213/16* (2013.01); *A01N 43/56* (2013.01); *C07D 213/71* (2013.01);
(Continued)

(58) Field of Classification Search
CPC .. C07D 213/71; C07D 237/16; C07D 401/12; C07D 405/04; C07D 405/14; C07D 409/04; C07D 409/14; A01N 43/58
See application file for complete search history.

(56) References Cited

U.S. PATENT DOCUMENTS

| 9,049,864 B2 | 6/2015 | Burton et al. | |
| 2004/0225125 A1* | 11/2004 | Chang | C07D 251/42 506/15 |

(Continued)

FOREIGN PATENT DOCUMENTS

| EP | 2042491 A | 4/2009 |
| GB | 1130716 A | 10/1968 |

(Continued)

OTHER PUBLICATIONS

Sotelo, Eddy et al., "Pyridazines. Part XXIX: synthesis and platelet aggregation inhibition activity of 5-substituted-6-phenyl-3(2H)-pyridazinones. Novel aspects of their biological actions," Bioorganic & Medicinal Chemistry, vol. 10, No. 9, pp. 2873-2882 (2002).*
International Search Report of PCT/US2016/058755 dated Dec. 14, 2016.
Sotelo et al., "Pyridazines. Part XXIX: Synthesis and Platelet Aggregation Inhibition Activity of 5-substituted-6-phenyl-3(2H)-pyridazinones. Novel Aspects of Their Biological Actions", Bioorganic & Medicinal Chemistry, vol. 10, No 9, Sep. 1, 2002, p. 2873-2882, XP055102768.

(Continued)

*Primary Examiner* — John Pak
(74) *Attorney, Agent, or Firm* — FMC Corporation

(57) ABSTRACT

Disclosed is a process for preparing a compound of Formula 1,

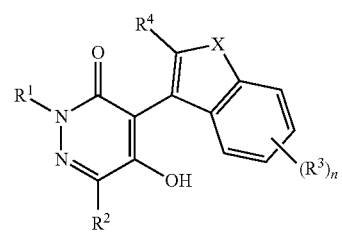

from a compound of Formula 2 wherein X, $R^1$, $R^2$, $R^3$, $R^4$, $R^5$, n, $R^6$, $R^7$, G and W are as defined in the disclosure. Also disclosed are compounds of Formulae 2 and 4

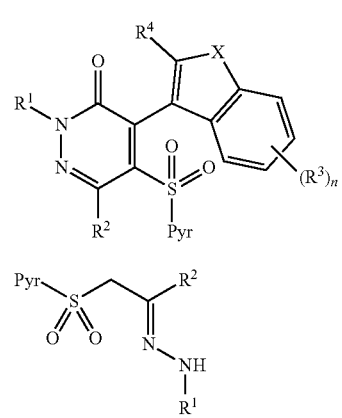

wherein X, $R^1$, $R^2$, $R^3$, $R^4$, $R^5$, n, $R^6$, $R^7$, G and W are as defined in the disclosure. Also disclosed is a process for preparing the compounds of Formulae 2 and 4.

10 Claims, No Drawings

(51) Int. Cl.
  C07D 409/14    (2006.01)
  C07D 213/16    (2006.01)
  C07D 213/71    (2006.01)
  C07D 405/04    (2006.01)
  C07D 409/04    (2006.01)
  C07D 237/16    (2006.01)
  A01N 43/56     (2006.01)
  A01N 43/58     (2006.01)

(52) U.S. Cl.
  CPC ......... *C07D 237/16* (2013.01); *C07D 401/12* (2013.01); *C07D 405/04* (2013.01); *C07D 405/14* (2013.01); *C07D 409/04* (2013.01); *C07D 409/14* (2013.01); *A01N 43/58* (2013.01)

(56) References Cited

U.S. PATENT DOCUMENTS

| | | |
|---|---|---|
| 2005/0020594 A1 | 1/2005 | Hepperle |
| 2010/0216642 A1 | 8/2010 | Fusaka |
| 2011/0098269 A1 | 4/2011 | Becknell et al. |
| 2013/0172556 A1 | 7/2013 | Jachmann et al. |
| 2014/0378688 A1 | 12/2014 | Jachmann et al. |
| 2017/0050953 A1* | 2/2017 | Selby ................ A01N 43/58 |

FOREIGN PATENT DOCUMENTS

| | | |
|---|---|---|
| GB | 2519092 A | 4/2015 |
| WO | 2009/086041 A1 | 7/2009 |
| WO | 2011/045271 A1 | 4/2011 |
| WO | WO 2012/033225 * | 3/2012 |
| WO | WO 2012/091156 * | 7/2012 |
| WO | 2013/160126 A1 | 10/2013 |
| WO | 2014/031971 A1 | 2/2014 |
| WO | 2015/052095 A1 | 4/2015 |
| WO | WO 2015/168010 * | 11/2015 |
| WO | 2017/074988 A1 | 5/2017 |

OTHER PUBLICATIONS

Babichev et al. 6-Amino-1-Aryl-4-Pyridazinones and Their Derivatives, Ukrainian Chemical Journal, 1983, vol. 49, No. 11, p. 1197-1202.

Wu et al, "Synthesis of γ-Oxo-α,β-dehydro-α-amino Acids from N-tert-Butyloxycarbonyl-α-Imino Esters and Carbonylmethyl 2-Pyridinylsulfones via an Mannich-Elimination Cascade", Asian Journal of Organic Chemistry, 2014, vol. 3, No. 7, p. 766-768.

Deng et al, "Synthesis of 3-substituted 1,5-aldehyde esters via an organocatalytic highly enantioselective conjugate addition of new carbonylmethyl 2-pyridinylsulfone to enals", Chemical Communications, 2012, vol. 48, No. 1, p. 148-150.

Settimo et al, "Isosteric replacement of the indole nucleus by benzothiophene and benzofuran in a series of ndolylglyoxylylamine derivatives with partial agonist activity at the benzodiazepine receptor", European Journal of Medicinal Chemistry, 1996, vol. 31, No. 12, p. 951-956.

* cited by examiner

INTERMEDIATES TO PREPARE PYRIDAZINONE HERBICIDES, AND A PROCESS TO PREPARE THEM

FIELD OF THE INVENTION

This invention relates to the preparation of certain pyridazinone compounds useful as herbicides and methods for their preparation.

BACKGROUND OF THE INVENTION

The invention relates to the method of preparation of certain pyridazinone herbicides of Formula 1, novel intermediates used to prepare them, and a novel method for preparing these intermediates.

SUMMARY OF THE INVENTION

This invention provides a process for preparing a compound of Formula 1

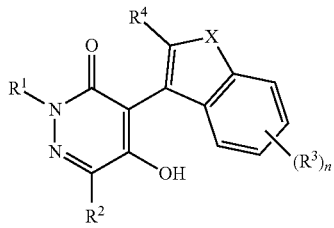

wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_1$-$C_7$ haloalkyl, $C_3$-$C_7$ haloalkenyl, $C_2$-$C_7$ alkoxyalkyl or $C_3$-$C_7$ alkylthioalkyl;
$R^2$ is $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl or $C_2$-$C_3$ alkoxycarbonyl; or phenyl optionally substituted by halogen, $C_1$-$C_4$ alkyl or $C_1$-$C_4$ haloalkyl;
X is O or S; or
X is —$C(R^6)$=$C(R^7)$—, wherein the carbon atom bonded to $R^6$ is also bonded to the carbon atom bonded to $R^4$, and the carbon atom bonded to $R^7$ is also bonded to the phenyl ring moiety in Formula 1;
each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;
n is 0, 1, 2 or 3; and
$R^4$, $R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl;

comprising hydrolyzing a herbicide intermediate compound of Formula 2

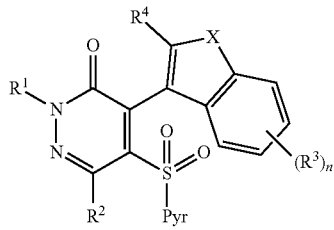

wherein
$R^1$, $R^2$, $R^3$, n, $R^4$, X, $R^6$ and $R^7$ are as defined for Formula 1 above; and
Pyr is a pyridine ring optionally substituted with halogen or $C_1$-$C_4$ alkyl.
This invention is also directed to a herbicide intermediate compound of Formula 2

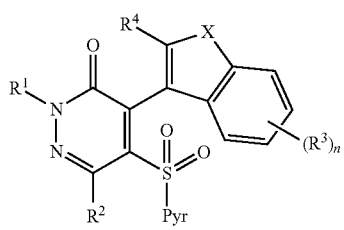

wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_1$-$C_7$ haloalkyl, $C_3$-$C_7$ haloalkenyl, $C_2$-$C_7$ alkoxyalkyl or $C_3$-$C_7$ alkylthioalkyl;
$R^2$ is $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl or $C_2$-$C_3$ alkoxycarbonyl; or phenyl optionally substituted by halogen, $C_1$-$C_4$ alkyl or $C_1$-$C_4$ haloalkyl;
X is O or S; or
X is —$C(R^6)$=$C(R^7)$—, wherein the carbon atom bonded to $R^6$ is also bonded to the carbon atom bonded to $R^4$, and the carbon atom bonded to $R^7$ is also bonded to the phenyl ring moiety in Formula 2;
each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;
n is 0, 1, 2 or 3;
$R^4$, $R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl; and Pyr is a pyridine ring optionally substituted with halogen or $C_1$-$C_4$ alkyl.

This invention also provides a process for preparing the herbicide intermediate compound of Formula 2
comprising cyclizing the product of the reaction of a herbicide intermediate compound of Formula 4

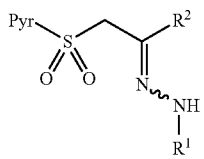

4 wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_1$-$C_7$ haloalkyl, $C_3$-$C_7$ haloalkenyl, $C_2$-$C_7$ alkoxyalkyl or $C_3$-$C_7$ alkylthioalkyl;

$R^2$ is $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl or $C_2$-$C_3$ alkoxycarbonyl; or phenyl optionally substituted by halogen, $C_1$-$C_4$ alkyl or $C_1$-$C_4$ haloalkyl; and Pyr is a pyridine ring optionally substituted with halogen or $C_1$-$C_4$ alkyl;
with a compound of Formula 3

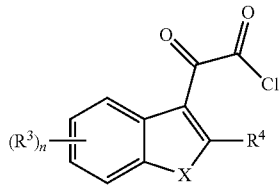

3 wherein
X is O or S; or
X is —C($R^6$)═C($R^7$)—, wherein the carbon atom bonded to $R^6$ is also bonded to the carbon atom bonded to $R^4$, and the carbon atom bonded to $R^7$ is also bonded to the phenyl ring moiety in Formula 3;

each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

n is 0, 1, 2 or 3; and $R^4$, $R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl.

This invention is also directed to the herbicide intermediate compound of Formula 4

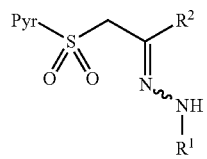

4 wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_1$-$C_7$ haloalkyl, $C_3$-$C_7$ haloalkenyl, $C_2$-$C_7$ alkoxyalkyl or $C_3$-$C_7$ alkylthioalkyl;

$R^2$ is $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl or $C_2$-$C_3$ alkoxycarbonyl; or phenyl optionally substituted by halogen, $C_1$-$C_4$ alkyl or $C_1$-$C_4$ haloalkyl; and Pyr is a pyridine ring optionally substituted with halogen or $C_1$-$C_4$ alkyl.

This invention also provides a process for preparing the herbicide intermediate compound of Formula 4
comprising contacting a compound of Formula 5

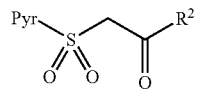

5 wherein
$R^2$ is $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl, $C_2$-$C_3$ alkoxycarbonyl; or phenyl optionally substituted by halogen, $C_1$-$C_4$ alkyl or $C_1$-$C_4$ haloalkyl; and Pyr is a pyridine ring optionally substituted with halogen or $C_1$-$C_4$ alkyl;
with a hydrazine of Formula 6

$R^1NHNH_2$   6 wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_1$-$C_7$ haloalkyl, $C_3$-$C_7$ haloalkenyl, $C_2$-$C_7$ alkoxyalkyl or $C_3$-$C_7$ alkylthioalkyl.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a process or method that comprises a list of elements is not necessarily limited to only those elements but may include other elements not expressly listed or inherent to such process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "alkylating" refers reaction in which nucleophile displaces a leaving group such as halide or sulfonate from a carbon-containing radical. Unless otherwise indicated, the term "alkylating" does not limit the carbon-containing radical to alkyl.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Cyanoalkyl" denotes an alkyl group substituted with one cyano group. Examples of "cyanoalkyl" include $NCCH_2$ and $NCCH_2CH_2$ (alternatively identified as $CH_2CH_2CN$). "Nitroalkyl" denotes an alkyl group substituted with one nitro group. Examples of "nitroalkyl" include $—CH_2NO_2$ and $—CH_2CH_2NO_2$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkoxyalkyl", "haloalkylthio", "haloalkenyl", "haloalkynyl", and the like, areis defined analogously to the term "haloalkyl". Examples of "haloalkoxy" include $CF_3O—$, $CCl_3CH_2O—$, $HCF_2CH_2CH_2O—$ and $CF_3CH_2O—$. Examples of "haloalkoxyalkyl" include $CF_3OCH_2—$, $CCl_3CH_2OCH_2—$, $HCF_2CH_2CH_2OCH_2—$ and $CF_3CH_2OCH_2—$. Examples of "haloalkylthio" include $CCl_3S—$, $CF_3S—$, $CCl_3CH_2S—$ and $ClCH_2CH_2CH_2S—$. Examples of "haloalkenyl" include $(Cl)_2C=CHCH_2—$ and $CF_3CH_2CH=CHCH_2—$. Examples of "haloalkynyl" include $HC≡CHCl—$, $CF_3C≡C—$, $CCl_3C≡C—$ and $FCH_2C≡CCH_2—$.

"Alkoxycarbonyl" denotes a straight-chain or branched alkoxy moieties bonded to a $C(=O)$ moiety. Examples of "alkoxycarbonyl" include $CH_3OC(=O)—$, $CH_3CH_2OC(=O)—$, $CH_3CH_2CH_2OC(=O)—$, $(CH_3)_2CHOC(=O)—$ and the different butoxy- or pentoxycarbonyl isomers. "Alkylcarbonylalkyl" denotes a straight-chain or branched alkylcarbonyl moiety bonded through a straight-chain or branched alkyl group. Examples of "alkylcarbonylalkyl" include $CH_3C(=O)CH_2—$, $CH_3CH_2C(=O)CH_2—$, $CH_3CH_2CH_2C(=O)CH_2—$, $(CH_3)_2CHC(=O)CH_2—$ and the different butoxy- or pentoxycarbonyl isomers.

The total number of carbon atoms in a substituent group is indicated by the "$C_i$-$C_j$" prefix where i and j are numbers from 1 to 7. For example, $C_1$-$C_4$ alkylsulfonyl designates methylsulfonyl through butylsulfonyl; $C_2$ alkoxyalkyl designates $CH_3OCH_2—$; $C_3$ alkoxyalkyl designates, for example, $CH_3CH(OCH_3)—$, $CH_3OCH_2CH_2—$ or $CH_3CH_2OCH_2—$; and $C_4$ alkoxyalkyl designates the various isomers of an alkyl group substituted with an alkoxy group containing a total of four carbon atoms, examples including $CH_3CH_2CH_2OCH_2—$ and $CH_3CH_2OCH_2CH_2—$.

When a compound is substituted with a substituent bearing a subscript that indicates the number of said substituents can exceed 1, said substituents (when they exceed 1) are independently selected from the group of defined substituents, e.g., $(R^3)_n$, wherein n is 1, 2, or 3. When a group contains a substituent which can be hydrogen, for example $R^4$, then when this substituent is taken as hydrogen, it is recognized that this is equivalent to said group being unsubstituted. When a variable group is shown to be optionally attached to a position, for example $(R^3)_n$ wherein n may be 0, then hydrogen may be at the position even if not recited in the variable group definition. When one or more positions on a group are said to be "not substituted" or "unsubstituted", then hydrogen atoms are attached to take up any free valency. The term "ring system" denotes two or more fused rings.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Herbicide intermediate compounds of Formulae 2 and 4 typically exist in more than one form, and thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of herbicide intermediate compounds of Formula 2 and 4 can exhibit beneficial effects (e.g., suitability for preparation in a process of preparation) relative to another polymorph or a mixture of polymorphs of the same compounds of herbicide intermediate compound of Formula 2 or 4. Preparation and isolation of a particular polymorph of herbicide intermediate compounds of Formula 2 or 4 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art recognizes that because under process conditions, chemical compounds can be isolated in their corresponding nonsalt or salt forms. Thus, a wide variety of salts of a compound of Formula 1 can be isolated using the present process or processes depending on the base utilized in the method to prepare a compound of Formula 1. Likewise, the herbicide intermediate compound of Formula 2 can be isolated as the salt or non-salt form depending on the base used in the method to prepare them. Suitable salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The present invention comprises herbicide intermediate compounds of Formula 2 and 4, and methods to make the compound of Formulae 1 and herbicide intermediate compounds of Formulae 2 and 4.

Embodiments of the present invention as described in the Summary of the Invention include:

Embodiment A1

The process for preparing a compound of Formula 1 as described in the Summary of the Invention wherein hydrolyzing the herbicide intermediate compound of Formula 2 is performed in a suitable solvent and in the presence of a suitable organic or inorganic base.

Embodiment A2

The process of Embodiment A1 wherein hydrolyzing is performed in a solvent selected from N-methylpyrrolidinone, $H_2O$, N,N-dimethylformamide and dimethylsulfoxide, and the base is selected from sodium hydroxide, potassium hydroxide or potassium carbonate.

Embodiment A3

The process of Embodiment A2 wherein hydrolyzing is performed in a solvent selected from N-methylpyrrolidinone and water, and the base is an inorganic base selected from sodium hydroxide or potassium hydroxide.

Embodiment A4

The process of Embodiment A1 wherein hydrolyzing is performed in a mixture of N-methylpyrrolidinone and $H_2O$, and the base is sodium hydroxide.

Embodiment A5

The process of any one of Embodiments A1 through A4 wherein in the compound of Formula 1
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_1$-$C_7$ haloalkyl, $C_2$-$C_7$ alkoxyalkyl or $C_3$-$C_7$ alkylthioalkyl;
$R^2$ is $C_1$-$C_7$ alkyl, $C_3$-$C_7$ cycloalkyl, $C_4$-$C_7$ cycloalkylalkyl, $C_1$-$C_7$ haloalkyl or $C_2$-$C_7$ alkoxyalkyl;
each $R^3$ is independently halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy, $C_1$-$C_5$ haloalkoxy or $C_1$-$C_5$ alkylthio;
n is 0, 1 or 2;
$R^4$, $R^6$ and $R^7$ are independently H, halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy, $C_1$-$C_5$ alkylthio; and
wherein in the compound of 2
$R^1$, $R^2$, $R^3$, n, $R^4$, X, $R^6$ and $R^7$ are as defined for Formula 1 above; and Pyr is a pyridine ring optionally substituted with F, Cl, Br or $CH_3$.

Embodiment A6

The process of Embodiment A5 wherein in the compound of Formula 1
- $R^1$ is H, $C_1$-$C_7$ alkyl, $C_3$-$C_7$ alkenyl, $C_3$-$C_7$ alkynyl, $C_3$-$C_7$ cycloalkyl or $C_4$-$C_7$ cycloalkylalkyl;
- $R^2$ is $C_1$-$C_7$ alkyl, $C_3$-$C_7$ cycloalkyl, $C_4$-$C_7$ cycloalkylalkyl or $C_2$-$C_7$ alkoxyalkyl;
- X is S; or
- X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 2;
- each $R^3$ is independently halogen, $C_1$-$C_5$ alkyl, $C_3$-$C_5$ cycloalkyl or $C_1$-$C_5$ alkoxy;
- $R^4$, $R^6$ and $R^7$ are independently H, halogen, $C_1$-$C_5$ alkyl or $C_1$-$C_5$ alkoxy; and wherein in the compound of 2
- $R^1$, $R^2$, $R^3$, $R^4$, X, $R^6$ and $R^7$ are as defined for Formula 1 above; and
- Pyr is a 2-pyridinyl ring optionally substituted with F, Cl, Br or $CH_3$.

Embodiment A7

The process of Embodiment A6 wherein in the compound of Formula 1
- $R^1$ is H or $C_1$-$C_7$ alkyl;
- $R^2$ is $C_1$-$C_7$ alkyl or $C_3$-$C_7$ cycloalkyl;
- X is S;
- each $R^3$ is independently halogen $C_1$-$C_5$ alkyl or $C_1$-$C_5$ alkoxy;
- $R^4$ is H, halogen or $C_1$-$C_5$ alkyl; and wherein in the compound of 2
- $R^1$, $R^2$, $R^3$, $R^4$ and X are as defined for Formula 1 above; and
- Pyr is an unsubstituted 2-pyridinyl ring.

Embodiment A8

The process of Embodiment A6 wherein in the compound of Formula 1
- $R^1$ is H or $C_1$-$C_7$ alkyl;
- $R^2$ is $C_1$-$C_7$ alkyl or $C_3$-$C_7$ cycloalkyl;
- X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 2;
- each $R^3$ is independently halogen, $C_1$-$C_5$ alkyl or $C_1$-$C_5$ alkoxy;
- $R^4$, $R^6$ and $R^7$ are independently H, halogen or $C_1$-$C_5$ alkyl; and wherein in the compound of 2
- $R^1$, $R^2$, $R^3$, $R^4$, X, $R^6$ and $R^7$ are as defined for Formula 1 above; and
- Pyr is an unsubstituted 2-pyridinyl ring.

Embodiment A9

The process of any one of Embodiments A1 through A8 wherein
- $R^1$ is H or $CH_3$; and
- $R^2$ is $CH_3$ or c-Pr.

Embodiment A10

The process of Embodiment A9 wherein
- $R^1$ is $CH_3$; and
- $R^2$ is $CH_3$.

Embodiment A11

The process of any of Embodiments A1 through A10 wherein the term "hydrolyzing" is replaced with "de-protecting".

Embodiment B1

The herbicide intermediate compound of Formula 2 as defined in the Summary of the Invention wherein
- $R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_1$-$C_7$ haloalkyl, $C_2$-$C_7$ alkoxyalkyl or $C_3$-$C_7$ alkylthioalkyl;
- $R^2$ is $C_1$-$C_7$ alkyl, $C_3$-$C_7$ cycloalkyl, $C_4$-$C_7$ cycloalkylalkyl, $C_1$-$C_7$ haloalkyl or $C_2$-$C_7$ alkoxyalkyl;
- each $R^3$ is independently halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy, $C_1$-$C_5$ haloalkoxy or $C_1$-$C_5$ alkylthio;
- n is 0, 1 or 2;
- $R^4$, $R^6$ and $R^7$ are independently H, halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy or $C_1$-$C_5$ alkylthio; and
- Pyr is a pyridine ring optionally substituted with F, Cl, Br or $CH_3$.

Embodiment B2

The herbicide intermediate compound of Embodiment B1 wherein
- $R^1$ is H, $C_1$-$C_7$ alkyl, $C_3$-$C_7$ alkenyl, $C_3$-$C_7$ alkynyl, $C_3$-$C_7$ cycloalkyl or $C_4$-$C_7$ cycloalkylalkyl;
- $R^2$ is $C_1$-$C_7$ alkyl, $C_3$-$C_7$ cycloalkyl, $C_4$-$C_7$ cycloalkylalkyl or $C_2$-$C_7$ alkoxyalkyl;
- X is S; or
- X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 2;
- each $R^3$ is independently halogen, $C_1$-$C_5$ alkyl, $C_3$-$C_5$ cycloalkyl or $C_1$-$C_5$ alkoxy;
- $R^4$, $R^6$ and $R^7$ are independently H, halogen, $C_1$-$C_5$ alkyl or $C_1$-$C_5$ alkoxy; and
- Pyr is a 2-pyridinyl ring optionally substituted with F, Cl, Br or $CH_3$.

Embodiment B3

The herbicide intermediate compound of Embodiment B2 wherein
- $R^1$ is H or $C_1$-$C_7$ alkyl;
- $R^2$ is $C_1$-$C_7$ alkyl or $C_3$-$C_7$ cycloalkyl;
- X is S;
- each $R^3$ is independently halogen $C_1$-$C_5$ alkyl or $C_1$-$C_5$ alkoxy;
- $R^4$ is H, halogen or $C_1$-$C_5$ alkyl; and
- Pyr is an unsubstituted 2-pyridinyl ring.

Embodiment B4

The herbicide intermediate compound of Embodiment B2 wherein
$R^1$ is H or $C_1$-$C_7$ alkyl;
$R^2$ is $C_1$-$C_7$ alkyl or $C_3$-$C_7$ cycloalkyl;
X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 2;
each $R^3$ is independently halogen, $C_1$-$C_5$ alkyl or $C_1$-$C_5$ alkoxy;
$R^4$, $R^6$ and $R^7$ are independently H, halogen or $C_1$-$C_5$ alkyl; and
Pyr is an unsubstituted 2-pyridinyl ring.

Embodiment B5

The herbicide intermediate compound of any one of Embodiments B1 through B4 wherein
$R^1$ is H or $CH_3$; and
$R^2$ is $CH_3$ or c-Pr.

Embodiment B6

The herbicide intermediate compound of Embodiment B5 wherein
$R^1$ is $CH_3$; and
$R^2$ is $CH_3$.

Embodiment C1

The process for preparing the herbicide intermediate compound of Formula 2 as described in the Summary of the Invention wherein cyclizing product of the reaction of a herbicide intermediate compound of Formula 4 with a compound of Formula 3 is performed in the presence of a suitable organic or inorganic base wherein in the Formula 4
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_1$-$C_7$ haloalkyl, $C_2$-$C_7$ alkoxyalkyl or $C_3$-$C_7$ alkylthioalkyl;
$R^2$ is $C_1$-$C_7$ alkyl, $C_3$-$C_7$ cycloalkyl, $C_4$-$C_7$ cycloalkylalkyl, $C_1$-$C_7$ haloalkyl or $C_2$-$C_7$ alkoxyalkyl;
and wherein in the compound of Formula 3
each $R^3$ is independently halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy, $C_1$-$C_5$ haloalkoxy or $C_1$-$C_5$ alkylthio;
n is 0, 1 or 2; and
$R^4$, $R^6$ and $R^7$ are independently H, halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy or $C_1$-$C_5$ alkylthio.

Embodiment C2

The process of Embodiment C1 wherein cyclizing the product of the reaction of a herbicide intermediate compound of Formula 4 with a compound of Formula 3 is performed in the presence of a suitable organic base and wherein in the Formula 4
$R^1$ is H or $C_1$-$C_7$ alkyl;
$R^2$ is $C_1$-$C_7$ alkyl or $C_3$-$C_7$ cycloalkyl;
and wherein in the compound of Formula 3
X is S; or X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 3;
each $R^3$ is independently halogen, $C_1$-$C_5$ alkyl, $C_3$-$C_5$ cycloalkyl or $C_1$-$C_5$ alkoxy; and
$R^4$, $R^6$ and $R^7$ are independently H, halogen, $C_1$-$C_5$ alkyl or $C_1$-$C_5$ alkoxy.

Embodiment C3

The process of Embodiment C2 wherein cyclizing the product of the reaction of a herbicide intermediate compound of Formula 4 with a compound of Formula 3 is performed in the presence of a suitable base selected from trimethylamine, triethylamine and tributylamine and wherein in the compound of Formula 4
$R^1$ is H or $C_1$-$C_7$ alkyl;
$R^2$ is $C_1$-$C_7$ alkyl or $C_3$-$C_7$ cycloalkyl;
and wherein in the compound of Formula 3
X is S;
each $R^3$ is independently halogen $C_1$-$C_5$ alkyl or $C_1$-$C_5$ alkoxy; and
$R^4$ is H, halogen or $C_1$-$C_5$ alkyl.

Embodiment C4

The process of Embodiment C2 wherein cyclizing the product of the reaction of a herbicide intermediate compound of Formula 4 with a compound of Formula 3 is performed in the presence of a suitable base selected from trimethylamine, triethylamine and tributylamine and wherein in the compound of Formula 4
$R^1$ is H or $C_1$-$C_7$ alkyl;
$R^2$ is $C_1$-$C_7$ alkyl or $C_3$-$C_7$ cycloalkyl;
and wherein in the compound of Formula 3
X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 3;
each $R^3$ is independently halogen, $C_1$-$C_5$ alkyl or $C_1$-$C_5$ alkoxy; and
$R^4$, $R^6$ and $R^7$ are independently H, halogen or $C_1$-$C_5$ alkyl.

Embodiment C5

The process of any one of Embodiments C1 through C4 wherein
$R^1$ is H or $CH_3$; and
$R^2$ is $CH_3$ or c-Pr.

Embodiment C6

The process of Embodiment C5 wherein
$R^1$ is $CH_3$; and
$R^2$ is $CH_3$.

Embodiment C7

The compound of Formula 1 prepared by the process of any one of Embodiments A1 through A10 using the compound of Formula 2 characterized by preparing the compound of Formula 2 by the method of any one of Embodiments C1 through C6.

Embodiment C8

The compound of Formula 2 prepared by the process of any one of Embodiments C1 through C6.

Embodiment C9

The process of any one of Embodiments C1 through C8 wherein the phrase "cyclizing the product of the reaction of a herbicide intermediate compound of Formula 4 with a compound of Formula 3" is replaced with "cyclizing a herbicide intermediate compound of Formula 4 with a compound of Formula 3".

Embodiment D1

The herbicide intermediate compound of Formula 4 wherein
- $R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_1$-$C_7$ haloalkyl, $C_2$-$C_7$ alkoxyalkyl or $C_3$-$C_7$ alkylthioalkyl;
- $R^2$ is $C_1$-$C_7$ alkyl, $C_3$-$C_7$ cycloalkyl, $C_4$-$C_7$ cycloalkylalkyl, $C_1$-$C_7$ haloalkyl or $C_2$-$C_7$ alkoxyalkyl; and
- Pyr is a pyridine ring optionally substituted with F, Cl, Br or $CH_3$.

Embodiment D2

The herbicide intermediate compound of Embodiment D1 wherein
- $R^1$ is H, $C_1$-$C_7$ alkyl, $C_3$-$C_7$ alkenyl, $C_3$-$C_7$ alkynyl, $C_3$-$C_7$ cycloalkyl or $C_4$-$C_7$ cycloalkylalkyl;
- $R^2$ is $C_1$-$C_7$ alkyl, $C_3$-$C_7$ cycloalkyl, $C_4$-$C_7$ cycloalkylalkyl or $C_2$-$C_7$ alkoxyalkyl; and
- Pyr is a 2-pyridinyl ring optionally substituted with F, Cl, Br or $CH_3$.

Embodiment D3

The herbicide intermediate compound of Embodiment D2 wherein
- $R^1$ is H or $C_1$-$C_7$ alkyl;
- $R^2$ is $C_1$-$C_7$ alkyl or $C_3$-$C_7$ cycloalkyl; and
- Pyr is an unsubstituted 2-pyridinyl ring.

Embodiment D4

The herbicide intermediate compound of any one of Embodiments D1 through D3 wherein
- $R^1$ is H or $CH_3$; and
- $R^2$ is $CH_3$ or c-Pr.

Embodiment D5

The herbicide intermediate compound of Embodiment D4 wherein
- $R^1$ is $CH_3$; and
- $R^2$ is $CH_3$.

Embodiment E1

The process for preparing the herbicide intermediate compound of Formula 4 as described in the Summary of the Invention wherein in the compound of Formula 5
- $R^2$ is $C_1$-$C_7$ alkyl, $C_3$-$C_7$ cycloalkyl, $C_4$-$C_7$ cycloalkylalkyl, $C_1$-$C_7$ haloalkyl or $C_2$-$C_7$ alkoxyalkyl;

and wherein in the compound of Formula 6
- $R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_1$-$C_7$ haloalkyl, $C_2$-$C_7$ alkoxyalkyl or $C_3$-$C_7$ alkylthioalkyl.

Embodiment E2

The process of Embodiment E1 wherein in the compound of Formula 5
- $R^2$ is $C_1$-$C_7$ alkyl or $C_3$-$C_7$ cycloalkyl;

and wherein in the compound of Formula 6
- $R^1$ is H or $C_1$-$C_7$ alkyl.

Embodiment E3

The process of Embodiment E3 wherein in the compound of Formula 5
- $R^2$ is $CH_3$ or c-Pr;

and wherein in the compound of Formula 6
- $R^1$ is H or $CH_3$.

Embodiment E4

The process of Embodiment E3 wherein in the compound of Formula 5
- $R^2$ is $CH_3$;

and wherein in the compound of Formula 6
- $R^1$ is $CH_3$.

Embodiment E5

The compound of Formula 2 prepared by the process of any one of Embodiments C2 through C4 using the compound of Formula 4 characterized by preparing the compound of Formula 4 by the method of any one of Embodiments E1 through E4.

Embodiment E6

The compound of Formula 4 prepared by the process of any one of Embodiments E1 through E4.

Embodiments of this invention, including Embodiments A1 through A11, B1 through B6, C1 through C9, D1 through D5, and E1 through E6 above as well as any other embodiments described herein, can be combined in any manner, and the descriptions of variables in the embodiments pertain not only to the compounds of Formula 1 but also to the starting intermediate compounds of Formulae 2, 4, 5 and 6 useful for preparing the compounds of Formula 1. In addition, embodiments of this invention, including Embodiments A1 through A11, B1 through B6, C1 through C9, D1 through D5, and E1 through E6 above as well as any other embodiments described herein, and any combination thereof, pertain to the compounds and methods of the present invention.

A compound of Formula 1 can be prepared by general methods known in the art of synthetic organic chemistry. A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Hydroxypyridazinones of Formula 1 can be made by hydrolysis of pyridinylsulfonyl pyridazinones of Formula 2 (i.e. "hydrolyzing" or, alternatively "de-protecting") under basic aqueous conditions as shown in Scheme 1. Examples of suitable bases ("hydrolyzing bases" or alternatively "de-protecting bases") include but are not limited to sodium hydroxide, potassium hydroxide, other alkaline or alkali metal hydroxides and alkali or alkaline metal carbonates. Useful co-solvents for this reaction include but are not limited to methanol, ethanol, isopropanol, acetone, acetonitrile, tetrahydrofuran, dioxane, dimethylsulfoxide, N,N-dimethylformamide or N-methylpyrrolidinone (or mixtures thereof). The hydrolysis reaction is usually conducted in a temperature range from about 0 to 120° C. The effects of solvent, base, temperature and addition time are all interdependent, and choice of reaction conditions is important to minimize the formation of byproducts. Base mediated hydrolysis of the pyridinylsulfonyl group affords an aqueous mixture comprising an ionized form of the resulting hydroxypyridazinone of Formula 1. Acidification with a suitable acid, such as hydrochloric acid, sulfuric acid or acetic acid yields the free hydroxypyridazinone 1 which can be isolated by methods known to those skilled in the art that include precipitation, extraction, crystallization or distillation methods. In some cases, purification by chromatography may be required.

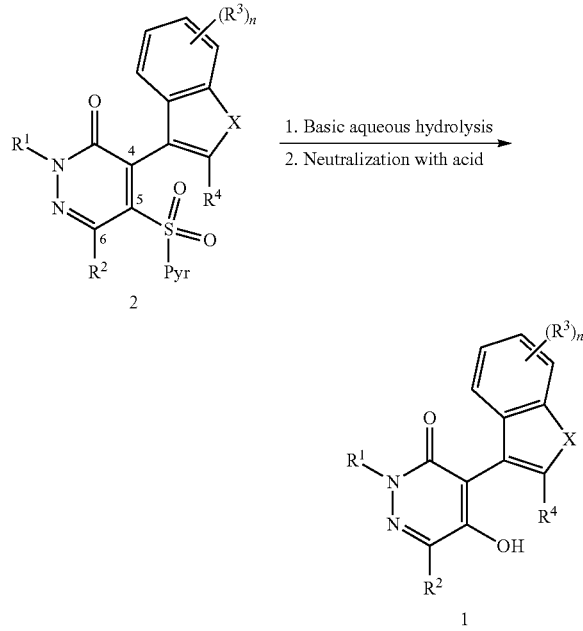

Scheme 1

Pyridinylsulfonyl pyridazinones of Formula 2 can be prepared by cyclizing a substituted aryl or heteroaryl oxalyl chloride of Formula 3 with a pyridinylsulfonylmethyl hydrazone of Formula 4 in the presence of a suitable base and solvent as shown in Scheme 2. Preferred bases (i.e. "cyclizing bases") include but are not limited to trialkylamines (such as triethylamine or Hunigs base), amidine bases such as 1,8-Diazabicyclo[5.4.0]undec-7-ene (DBU), pyridine or a metal carbonate. Solvents for this cyclization reaction can be aprotic or protic and include but are not limited to methanol, ethanol, isopropanol, dimethoxyethane, acetone, acetonitrile, dioxane, diethyl ether, tetrahydrofuran, dimethylsulfoxide, N,N-dimethylformamide or N-methyl pyrrolidinone (or mixtures thereof). The cyclizing reaction can be run under a range of temperatures, typically from 0° C. to the reflux temperature of the solvent. The cyclizing reaction can take place under anhydrous conditions or as aqueous mixtures under Schotten-Baumann conditions.

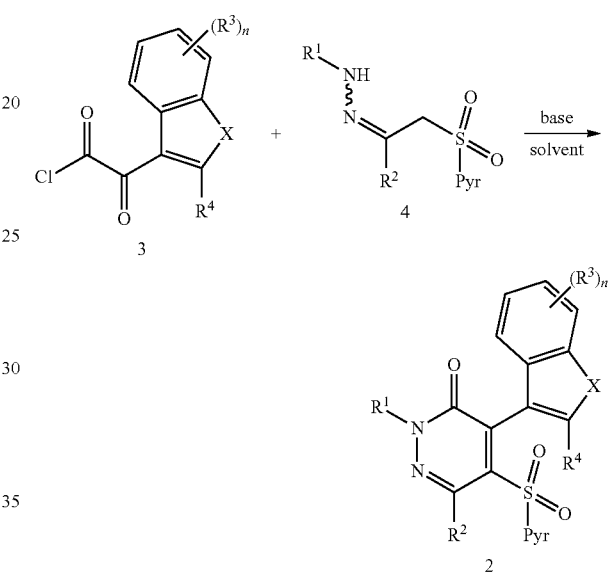

Scheme 2

The herbicide intermediate compound (pyridinylsulfonyl pyridazinones) of Formula 2 can be prepared by cyclizing the product of the reaction of a (pyridinylsulfonylmethyl hydrazone) herbicide intermediate compound of Formula 4 with a (substituted aryl or heteroaryl oxalyl chloride) compound of Formula 3. As used herein the phrase "product of the reaction" refers to the keto-amide compound of Formula 2A. The compound of Formula 2A can be isolated as an intermediate, but normally cyclizes in-situ in the presence of the same cyclizing base used to react a compound of Formula 4 with a compound of Formula 3. As shown in Scheme 2A, the keto-amide compound of Formula 2A cyclizes in the presence of a suitable base and solvent. Preferred bases for the cylization of a compound of Formula 2A are generally the same as the "cyclizing bases" defined above for Scheme 2, but also include sodium hydride, sodium alkoxides or other metal alkoxides. Appropriate "cyclizing bases" also include mono- di- or tri-alkylamine bases such as methylamine, diethylamine or N,N-diisopropylethylamine.

Scheme 2A

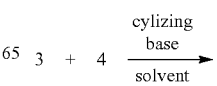

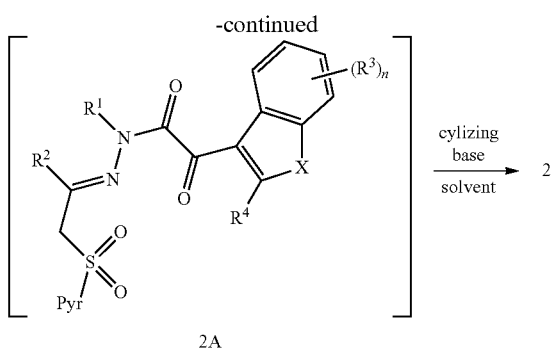

Hydrazones of Formula 4 are synthetically accessible by reaction of a substituted hydrazine of Formula 6 (i.e. R¹NHNH₂) with a pyridinylsulfonyl ketone compound of Formula 5 as shown in Scheme 3. Suitable solvents for this reaction include as methanol, ethanol, isopropanol, dimethoxyethane, acetone, acetonitrile, dioxane, diethyl ether, tetrahydrofuran, dimethylsulfoxide, N,N-dimethylformamide or N-methyl pyrrolidinone (or mixtures thereof). In some cases, a salt of the hydrazine (i.e. hydrochloride or sulfate salt) can be used where an equivalent or more of base is added to the reaction mixture allowing for conversion to the hydrazine free base in situ. Examples of effective bases used to prepare the free hydrazine include metal acetates (i.e. potassium or sodium acetate), metal carbonates or bicarbonates (i.e. potassium carbonate) and pyridine. The temperature of this reaction typically ranges from 0° C. to room temperature. Some hydrazones of Formula 4 are isolated as geometric isomers that can be used in the next step as a mixture or separated (by crystallization or chromatography) into the syn and anti isomers where either of them can be used in the following cyclization.

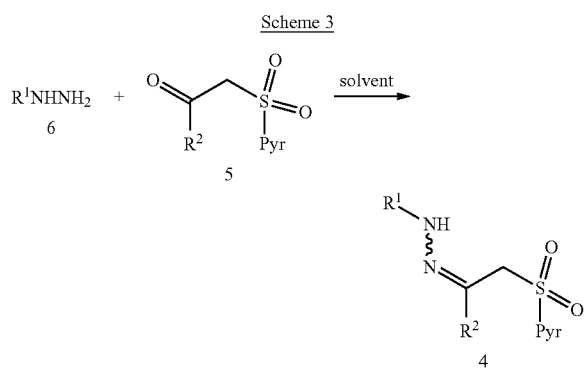

Pyridinylsulfonyl ketones of Formula 5 can be made by methods previously reported in the literature (*Tetrahedron* 2010, 66 (48), p 9445-9449; *Asian Journal of Organic Chemistry*, 2014, 3 (7), p 766-768, and WO 2009106817). Generally a pyridinylmercaptan of Formula Pyr-SH (which can exist in part or exclusively as the thiopyridone tautomer) is allowed to react with an α-haloketone of Formula XCH₂COR² where X is halogen) in the presence of a base such as potassium carbonate, potassium hydroxide, sodium hydroxide or pyridine in a suitable solvent, preferably acetone, acetonitrile, ethanol, dimethylsulfoxide, N,N-dimethylformamide or N-methyl pyrrolidinone (or mixtures thereof) at temperature ranging from 0° C. to 100° C.

Substituted aryl or heteroaryl oxalyl chlorides of Formula 3 can be made in some cases by a Friedal-Crafts acylation of an appropriately substituted aryl or heteroaryl compound of Formula 7 with ethyl or methyl oxalyl chloride in the presence of a Lewis Acid such as aluminum trichloride in a chlorinated solvent (i.e. dichloromethane), toluene or xylene at a temperature ranging from 0° C. to the reflux temperature of the solvent. The resulting oxalate compound of Formula 8 can be then hydrolyzed to the free acid or the sodium salt of the free acid. The resulting free acid can then be converted to the corresponding acid chloride of Formula 3 by reacting with oxalyl chloride or sulfonyl chloride in a solvent such as toluene, dichloromethane or dichloroethane. Some literature references on preparing aryl oxalyl chlorides include: WO 2015035051; *Tetrahedron* 2015, 71 (35), p 5776-5780; *J.A.C.S.* 2015, 137 (14), p 4626-4629 and WO 2012033225. Alternatively, oxalates of Formula 8 can be made from substituted bromoaryls and bromoheteroaryls of Formula 9 by initial formation of a Grignard Reagent by reaction with magnesium in a solvent such as tetrahydrofuran followed by addition of ethyl or methyl oxalate (CO₂Et₂ or CO₂Me₂) [see WO 2012033225 and *Chem. Comm.* 2014, 50 (100), p 15987-15990.

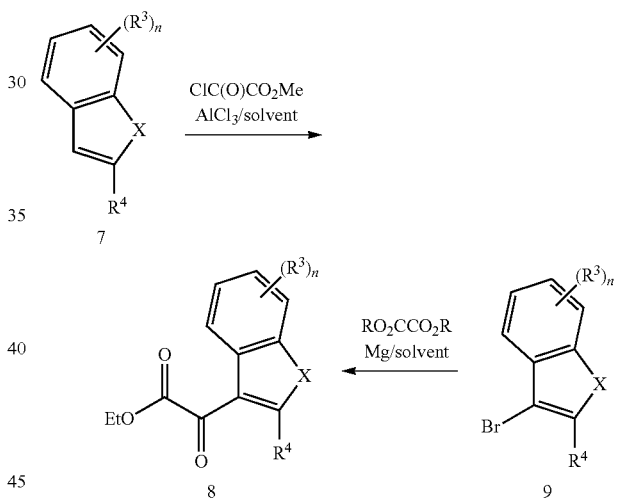

Compounds of Formula 3 can be prepared hydrolysis of the ester to the carboxylic acid, followed by treatment with oxalyl chloride as shown in Scheme 5 to provide the acyl chlorides of Formula 3. Compounds of Formula 8 are commercially available or can be prepared by methods known in the art.

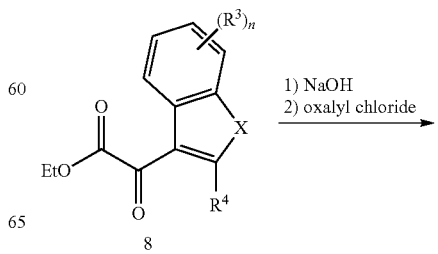

-continued

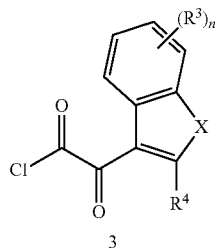

It is recognized that some reagents and reaction conditions described above for preparing compounds of Formulae 1, 2 and 4 using the methods described may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formulae 1, 2 and 4. One skilled in the art will also recognize that it may be necessary to perform a combination of the steps illustrated in the above schemes in an order other than that implied by the particular presented to prepare the compounds of Formulae 1, 2 and 4. One skilled in the art will also recognize that compounds of Formula 1 2 and 4 and the intermediates described herein can be subjected to various electrophilic, nucleophilic, radical, organometallic, oxidation, and reduction reactions to add substituents or modify existing substituents.

The following non-limiting Examples are meant to be illustrative of the present processes for preparing compounds of Formula 1, 2 and 4 and preparing the intermediates of Formulae 2 and 4. All NMR spectra are reported in CDCl$_3$ at 500 MHz downfield from tetramethylsilane unless otherwise indicated.

Synthesis Example 1

Preparation of 4-(4-fluoro-1-naphthalenyl)-5-hydroxy-2,6-dimethyl-3(2H)-pyridazinone Step A: Preparation of 1-(2-pyridinylsulfonyl)-2-propanone 1-(2-Pyridinylthio)-2-propanone, (e.g. Bradsher, C. K and Lohr D. F., *J. Het. Chem.* 1966, 3, 27-32) (9.26 g, 55.44 mmol) was dissolved in a solvent mixture of water (150 mL) tetrahydrofuran (150 mL) and methanol (150 mL) and Oxone® (potassium monopersulfate) (66 g, 292 mmol) was added. The biphasic reaction mixture was stirred at room temperature for 24 h. The reaction mixture was concentrated to ⅓ volume and extracted with ethyl acetate (3×50 mL). The organic layer was washed with water (2×20 mL) and brine (30 mL). The organic layer was collected, dried over MgSO$_4$ and concentrated under reduced pressure to provide the title compound as brown oil (8.00 g).

$^1$H NMR δ 8.75 (m, 1H), 8.12 (m, 1H), 8.00 (t, 1H), 7.64 (m, 1H), 4.48 (s, 2H), 2.41 (s, 3H).

Step B: Preparation of 1-(2-pyridinylsulfonyl)-2-propanone 2-methylhydrazone (Compound 3)

To a solution of compound of 1-(2-pyridinylsulfonyl)-2-propanone (i.e. the product of Example 1, Step A) (8.00 g, 44.00 mmol) in chloroform (30 mL), magnesium sulfate (8.00 g, 66.46 mmol) was added. The mixture was stirred at room temperature and methyl hydrazine (2.62 mL, 50.00 mmol) was added drop wise in 5 min. The reaction mixture was stirred at room temperature for 3 h. The reaction mixture was filtered through Celite® diatomaceaous earth filter aid, washed with chloroform (30 mL). The filtrate was concentrated under reduced pressure to provide the title compound as thick brown oil (9.00 g).

$^1$H NMR δ 8.82 (m, 1H), 8.00 (m, 1H), 7.92 (t, 1H), 7.62 (m, 1H), 4.82 (bs, 1H), 4.22 (s, 2H), 2.78 (s, 3H), 1.89 (d, 3H). The presence of 28% of the second isomer was evident by NMR.

Step C: Preparation of 4-fluoro-α-oxo-1-naphthaleneacetic Acid, Ethyl Ester

A suspension of aluminum chloride (30.2 g, 226 mmol) in dichloromethane (200 mL) was cooled to 0° C. The suspension was stirred and a solution containing 1-fluoronaphthalene (25.1 g, 172 mmol) and ethyl chlorooxoacetae (25.2 g, 184 mmol) in dichloromethane (150 mL) was added drop wise over 30 min (slight exothermic, maximum temperature of reaction mixture was about 7° C.). The mixture was stirred for 15 min and allowed to stir at room temperature for 4 h. The reaction mixture was slowly added to a solution of ice water (300 mL) and 1 N aqueous hydrochloric acid (50 mL). The biphasic mixture was stirred for 30 min and the organic layer was isolated. The organic layer was washed with water (2×25 mL) and brine (30 mL), dried (MgSO$_4$) and concentrated under reduced pressure to provide a yellow oil (42 g). This material was diluted with hexane (150 mL) and stirred. The resulting precipitate that formed was collected by filtration, washed with hexane (15 mL) and dried to provide the title compound as an off-white solid (34 g).

$^1$H NMR δ 9.21 (m, 1H), 8.21 (m, 1H), 8.00 (m, 1H), 7.77 (m, 1H), 7.63 (m, 1H) 7.34 (m, 1H), 4.52 (q, 2H), 1.50 (t, 3H).

Step D: Preparation of 4-fluoro-α-oxo-1-naphthaleneacetic Acid

4-Fluoro-α-oxo-1-naphthaleneacetic acid, ethyl ester (i.e. the product of Example 1, Step C) (21 g, 85 mmol) was dissolved in tetrahydrofuran (35 mL) and 1 N aqueous solution of sodium hydroxide (112 mL, 101 mmol) was added, the reaction mixture was stirred for 2 h. A solid precipitated from the reaction mixture. The mixture was diluted with water (100 mL). 1 N Aqueous hydrochloric acid was added until the pH of the reaction mixture was 3. The resulting solids were collected by filtration, washed with water (2×20 mL), hexane (1×20 mL) and dried under vacuum to provide of title compound as a white solid (15 g).

$^1$H NMR δ 9.21 (m, 1H), 8.21 (m, 1H), 8.00 (m, 1H), 7.77 (m, 1H), 7.63 (m, 1H), 7.34 (m, 1H).

Step E: Preparation of 4-fluoro-α-oxo-1-naphthaleneacetyl Chloride 4-fluoro-α-oxo-1-naphthaleneacetic acid (i.e. the product of Example 1, Step D) (2.18 g, 10 mmol) was suspended in dichloromethane (20 mL) and oxalyl chloride (3.81 g, 30 mmol) was added in one portion followed by 3 drops of N,N-dimethylformamide and the reaction mixture was stirred at room temperature for 3 h. The reaction mixture was concentrated under reduced pressure to provide the title compound as a yellow solid (2.4 g).

$^1$H NMR δ 9.21 (m, 1H), 8.21 (m, 1H), 8.10 (m, 1H), 7.80 (m, 1H), 7.77 (m, 1H), 7.34 (m, 1H).

Step F: Preparation of 4-(4-fluoro-1-naphthalenyl)-2,6-dimethyl-5-(2-pyridinylsulfonyl)-3(2H)-pyridazinone (Compound 1)

1-(2-Pyridinylsulfonyl)-2-propanone 2-methylhydrazone (i.e. the product obtained in Example 1, Step B) (2.5 g, 11 mmol) was dissolved in dichloromethane (20 mL) and triethylamine (2.6 g, 26 mmol) was added. The reaction mixture was cooled to 5° C. with ice water, and a suspension of 4-fluoro-α-oxo-1-naphthaleneacetyl chloride (i.e. the product obtained in Example 1, Step E) in dichloromethane (2.4 g, 10 mmol) was added in 5 min. The reaction mixture was stirred at room temperature for further 18 h. The reaction mixture was diluted with water (50 mL) and extracted with dichloromethane (3×30 mL). The organic layer was further washed with water (2×20 mL) and brine (20 mL) and dried (MgSO$_4$). The organic layer was filtered and concentrated under reduced pressure to provide a solid product. The solid product was suspended in dichloromethane:diethyl ether (2:8) (30 mL) and resulting solids were collected, dried under vacuum to provide the title compound as a light yellow solid (2.2 g).

$^1$H NMR δ 8.21 (m, 1H), 7.91 (m, 1H), 7.42 (m, 1H), 7.30 (m, 1H), 7.23 (m, 2H), 7.12 (m, 3H), 6.8 (m, 1H), 3.84 (s, 3H), 2.88 (s, 3H).

Step G: Preparation of 4-(4-fluoro-1-naphthalenyl)-5-hydroxy-2,6-dimethyl-3(2H)-pyridazinone 4-(4-Fluoro-1-naphthalenyl)-2,6-dimethyl-5-(2-pyridinylsulfonyl)-3(2H)-pyridazinone (i.e. the product obtained in Example 1, Step F) (0.41 g, 1 mmol) was dissolved in 1,4-dioxane (5 mL) and sodium hydroxide (0.100 g, 2.5 mmol) was added followed by water (0.5 mL) and the reaction mixture was heated at 90° C. for 1 h. The reaction mixture was concentrated under reduced pressure and residual solids were suspended in water (5 mL). The mixture was acidified to a pH of 3 by adding 1 N aqueous hydrochloric acid. The resulting solids were stirred at room temperature for 15 min and collected by filtration, washed with water (2×5 mL), hexane (2×5 mL) and dried under vacuum to provide the title compound as an off-white solid (0.265 g).

$^1$H NMR (dmso-d$_6$) δ 10.21 (bs, 1H), 8.15 (d, 1H), 7.70 (m, 1H), 7.55 (m, 2H), 7.40 (m, 1H), 7.30 (m, 1H).

Synthesis Example 2

Preparation of 4-(2,5-dimethylbenzo[b]thien-3-yl)-5-hydroxy-2,6-dimethyl-3(2H)-pyridazinone Step A: Preparation of 1-[(2-chloro-2-propen-1-yl)thio]-4-methyl-benzene 2,3-Dichloro-1-propene (20.5 g, 185 mmol) was added to a solution of 4-methylbenzenethiol (22.0 g, 177 mmol) in acetone (150 mL). The mixture was cooled to 12° C. and a solution of potassium carbonate (26 g, 188 mmol) in water (75 mL) was added drop wise over 15 min. The reaction mixture was stirred at 20° C. for 18 h. The mixture was diluted with water (400 mL) and hexane (500 mL). The mixture was extracted and organic layer was collected. The organic layer was washed with water (2×50 mL) and brine (50 mL), and concentrated under reduced pressure to provide the title compound as a clear orange oil (34.7 g).

$^1$H NMR δ 7.29 (m, 2H), 7.24 (m, 2H), 5.23 (m, 2H), 3.66 (m, 2H), 2.32 (s, 3H).

Step B: Preparation of 2,5-dimethyl-benzo[b]thiophene

1-[(2-Chloro-2-propen-1-yl)thio]-4-methyl-benzene (i.e. the compound of Example 2, Step A) (34.7 g, 175 mmol) was added to N,N-dimethylaniline (200 mL, 947 mmol) and the resultant mixture was flushed with nitrogen for 10 min. The reaction mixture was slowly heated to 195° C. for 24 h. The reaction mixture was concentrated under reduced pressure to remove N,N-dimethylaniline. The residue was diluted with hexanes (500 mL) and filtered to remove any insoluble solids. The filtrate was washed with 1 N aqueous hydrochloric acid (2×50 mL), water (2×50 mL) and the organic layer was collected. The organic layer was concentrated under reduced pressure to provide an amber oil (20.95 g). This material was further purified by silica gel column chromatography eluting with hexane to provide the title compound as a crystalline yellow solid (17 g).

$^1$H NMR δ 7.79 (d, 1H), 7.41 (s, 1H), 7.23 (d, 1H), 6.80 (d, 1H), 2.57 (s, 3H), 2.43 (s, 3H).

Step C: Preparation of ethyl 2,5-dimethyl-α-oxobenzo[b]thiophene-3-acetate

Under a nitrogen atmosphere 2,5-dimethyl-benzo[b]thiophene (i.e. the compound of Example 2, Step B) (23 g, 140 mmol) was dissolved in dichloromethane (280 mL), cooled to 0° C. and ethyl chlorooxoacetate (18 mL, 160 mmol) was added over 2 min. The reaction mixture was stirred and aluminum chloride (24 g, 180 mmol) was added in portions over 1 h. The reaction mixture was stirred at ambient temperature for 18 h. The reaction mixture was poured over a mixture of ice and water (300 mL) and 1 N hydrochloric acid (50 mL). The mixture was stirred for 1 h and the organic layer was separated. The organic layer was washed with water (2×20 mL) and brine (20 mL). The organic layer was dried over MgSO$_4$, concentrated under reduced pressure to provide of title compound as an amber oil (37.6 g).

$^1$H NMR δ 8.20 (s, 1H), 7.64 (d, 1H), 7.23 (d, 1H), 4.45 (q, 2H), 2.73 (s, 3H), 2.47 (s, 3H), 1.43 (t, 3H).

Step D: Preparation of 2,5-dimethyl-α-oxobenzo[b]thiophene-3-acetic Acid

Ethyl 2,5-dimethyl-α-oxobenzo[b]thiophene-3-acetate (i.e. the product obtained in Example 2, step C) (30.25 g, 115 mmol) was dissolved in tetrahydrofuran and 1 N aqueous sodium hydroxide (150 mL, 150 mmol) was added. The reaction mixture was heated at 68° C. for 2 h. The reaction mixture was allowed to come to room temperature and concentrated under reduced pressure to provide a solid residue. The solid residue was diluted with water (100 mL) and acidified to pH 3 with 6 N hydrochloric acid, and extracted with dichloromethane (3×50 mL). The organic layer was collected, washed with water (2×20 mL), brine (20 mL), dried over MgSO$_4$ and filtered. The filtrate was concentrated under reduced pressure to provide the title compound as a light yellow solid (26 g).

$^1$H NMR δ 10.4 (bs, 1H), 8.12 (s, 1H), 7.65 (d, 1H), 7.21 (d, 1H), 2.79 (s, 3H), 2.47 (s, 3H).

Step E: Preparation of 2,5-dimethyl-α-oxobenzo[b]thiophene-3-acetyl Chloride 2,5-Dimethyl-α-oxobenzo[b]thiophene-3-acetic acid (i.e. the product obtained in Example 2, Step D) (12.55 g, and 53.6 mmol) was dissolved in dichloromethane (50 mL) and 3 drops of N,N-dimethylformamide was added. The mixture was stirred at room temperature and oxalyl chloride (13.6 mL, 160 mmol) was added drop wise. The reaction mixture was stirred at room temperature for 2 h. The mixture was concentrated under reduced pressure to provide the title compound as a light yellow solid (13.56 g).

$^1$H NMR δ 8.15 (s, 1H), 7.70 (d, 1H), 7.31 (d, 1H), 2.81 (s, 3H), 2.50 (s, 3H).

Step F: Preparation of 4-(2,5-dimethylbenzo[b]thien-3-yl)-2,6-dimethyl-5-(2-pyridinylsulfonyl)-3(2H)-pyridazinone (Compound 2)

1-(2-Pyridinylsulfonyl)-2-propanone 2-methylhydrazone (i.e. the compound obtained in Example 1, Step B) (2.5 g, 11 mmol) was dissolved in dichloromethane (20 mL) and triethylamine (2.6 g, 26 mmol) was added. The reaction mixture was cooled to 5° C. with ice water, and a suspension of 2,5-dimethyl-α-oxobenzo[b]thiophene-3-acetyl chloride (i.e. the product obtained in Example 3, Step E) (2.53 g, 10 mmol) was added in 5 min. The reaction mixture was allowed to warm to room temperature and stirred at room temperature for further 18 h. The reaction mixture was diluted with water (50 mL) and extracted with dichloromethane (3×30 mL). The organic layer was further washed with water (2×20 mL) and brine (20 mL) and dried over MgSO$_4$. The organic layer was filtered and concentrated under reduced pressure to provide a solid. The solid was further purified by silica gel column chromatography, eluting with a gradient of ethyl acetate in hexanes to provide the title compound as a light yellow solid (3.25 g).

$^1$H NMR δ 8.25 (s, 1H), 7.40 (d, 1H), 7.31 (m, 2H), 6.91 (m, 1H), 6.81 (m, 1H), 6.63 (m, 1H), 3.83 (s, 3H), 2.91 (s, 3H), 2.35 (s, 3H), 2.27 (s, 3H).

Step G: Preparation of 4-(2,5-dimethylbenzo[b]thien-3-yl)-5-hydroxy-2,6-dimethyl-3(2H)-pyridazinone 4-(2,5-Dimethylbenzo[b]thien-3-yl)-2,6-dimethyl-5-(2-pyridinyl sulfonyl)-3 (2H)-pyridazinone (i.e. the product obtained in Example 2, Step F) (1.65 g, 3.88 mmol) was dissolved in N-methylpyrrolidone, sodium hydroxide (0.40 g, 10 mmol) was added followed by water (1 mL) and reaction mixture was heated at 90° C. for 2 h. The reaction mixture was allowed to warm to ambient temperature then water (10 mL) and toluene (15 mL) were added. The mixture was transferred to a seperatory funnel and the toluene layer was removed. The aqueous layer was acidified to pH 3 with 1N aqueous hydrochloric acid and the mixture was extracted with dichloromethane (2×20 mL). The organic layer was collected, dried over MgSO$_4$ and concentrated under reduced pressure to provide a semi-solid product. This solid was further purified by silica gel column chromatography eluting with a gradient of ethyl acetate in hexanes to provide the title compound as an off white solid (0.70 g).

$^1$H NMR δ 7.68 (d, 1H), 7.14 (d, 1H), 7.07 (s, 1H), 5.65 (s, 1H), 3.77 (s, 3H), 2.4 (s, 6H), 2.36 (s, 3H).

Examples of intermediates useful in the preparation of compounds of this invention and used in the processes are shown in Tables 1 through 5. The position(s) of the R$^3$ group(s) in Tables I-1a through I-3d is(are) based on the locant numbering shown below.

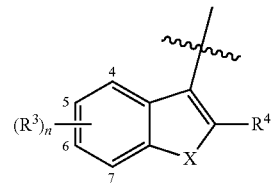

The following abbreviations are used in the Tables which follow: Me means methyl, Et means ethyl, Pr means propyl, and Ph means phenyl.

TABLE 1

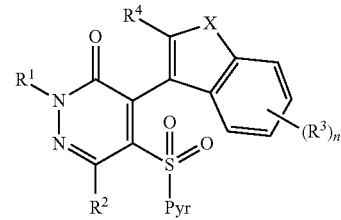

X is S, R$^1$ is Me, R$^2$ is Me, and Pyr is 2-pyridinyl.

| (R$^3$)$_n$ | R$^4$ |
|---|---|
| — | H |
| 4-Me | H |
| 5-Me | H |
| 6-Me | H |
| 7-Me | H |
| 4-Et | H |
| 5-Et | H |
| 6-Et | H |
| 7-Et | H |
| 4-Pr | H |
| 5-Pr | H |
| 6-Pr | H |
| 7-Pr | H |
| 4-OMe | H |
| 5-OMe | H |
| 6-OMe | H |
| 7-OMe | H |
| 4-CN | H |
| 5-CN | H |
| 6-CN | H |
| 7-CN | H |
| 4-CF$_3$ | H |
| 5-CF$_3$ | H |
| 6-CF$_3$ | H |
| 7-CF$_3$ | H |
| 4-F | H |
| 5-F | H |
| 6-F | H |
| 7-F | H |
| 4-Cl | H |
| 5-Cl | H |
| 6-Cl | H |
| 7-Cl | H |
| 4-Br | H |
| 5-Br | H |
| 6-Br | H |
| 7-Br | H |
| 4-OCHF$_2$ | H |

TABLE 1-continued

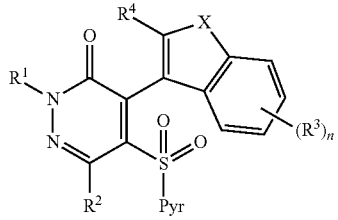

X is S, R¹ is Me, R² is Me, and Pyr is 2-pyridinyl.

| (R³)ₙ | R⁴ |
|---|---|
| 5OCHF₂ | H |
| 6-OCHF₂ | H |
| 7-OCHF₂ | H |
| 4-(C≡CH) | H |
| 5-(C≡CH) | H |
| 6-(C≡CH) | H |
| 7-(C≡CH) | H |
| 4,5-di-Me | H |
| 4,6-di-Me | H |
| 4,7-di-Me | H |
| 5,6-di-Me | H |
| 5,7-di-Me | H |
| 5-Cl, 7-Me | H |
| 5-Cl, 7-OMe | H |
| 5-F, 7-Me | H |
| 5-Me, 7-F | H |
| 5-Me, 7-Cl | H |
| 5-Me, 7-CN | H |
| 5-Me, 7-OMe | H |
| 5-(C≡CH), 7-Me | H |
| 5,7-di-F | H |
| 5,7-di-Cl | H |
| 5,7-di-Br | H |
| — | Pr |
| 4-Me | Pr |
| 5-Me | Pr |
| 6-Me | Pr |
| 7-Me | Pr |
| 4-Et | Pr |
| 5-Et | Pr |
| 6-Et | Pr |
| 7-Et | Pr |
| 4-Pr | Pr |
| 5-Pr | Pr |
| 6-Pr | Pr |
| 7-Pr | Pr |
| 4-OMe | Pr |
| 5-OMe | Pr |
| 6-OMe | Pr |
| 7-OMe | Pr |
| 4-CN | Pr |
| 5-CN | Pr |
| 6-CN | Pr |
| 7-CN | Pr |
| 4-CF₃ | Pr |
| 5-CF₃ | Pr |
| 6-CF₃ | Pr |
| 7-CF₃ | Pr |
| 4-F | Pr |
| 5-F | Pr |
| 6-F | Pr |
| 7-F | Pr |
| 4-Cl | Pr |
| 5-Cl | Pr |
| 6-Cl | Pr |
| 7-Cl | Pr |
| 4-Br | Pr |
| 5-Br | Pr |
| 6-Br | Pr |
| 7-Br | Pr |
| 4-OCHF₂ | Pr |
| 5OCHF₂ | Pr |
| 6-OCHF₂ | Pr |
| 7-OCHF₂ | Pr |

TABLE 1-continued

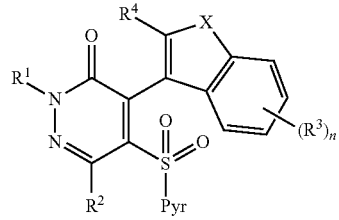

X is S, R¹ is Me, R² is Me, and Pyr is 2-pyridinyl.

| (R³)ₙ | R⁴ |
|---|---|
| 4-(C≡CH) | Pr |
| 5-(C≡CH) | Pr |
| 6-(C≡CH) | Pr |
| 7-(C≡CH) | Pr |
| 4,5-di-Me | Pr |
| 4,6-di-Me | Pr |
| 4,7-di-Me | Pr |
| 5,6-di-Me | Pr |
| 5,7-di-Me | Pr |
| 5-Cl, 7-Me | Pr |
| 5-Cl, 7-OMe | Pr |
| 5-F, 7-Me | Pr |
| 5-Me, 7-F | Pr |
| 5-Me, 7-Cl | Pr |
| 5-Me, 7-CN | Pr |
| 5-Me, 7-OMe | Pr |
| 5-(C≡CH), 7-Me | Pr |
| 5,7-di-F | Pr |
| 5,7-di-Cl | Pr |
| 5,7-di-Br | Pr |
| — | Br |
| 4-Me | Br |
| 5-Me | Br |
| 6-Me | Br |
| 7-Me | Br |
| 4-Et | Br |
| 5-Et | Br |
| 6-Et | Br |
| 7-Et | Br |
| 4-Pr | Br |
| 5-Pr | Br |
| 6-Pr | Br |
| 7-Pr | Br |
| 4-OMe | Br |
| 5-OMe | Br |
| 6-OMe | Br |
| 7-OMe | Br |
| 4-CN | Br |
| 5-CN | Br |
| 6-CN | Br |
| 7-CN | Br |
| 4-CF₃ | Br |
| 5-CF₃ | Br |
| 6-CF₃ | Br |
| 7-CF₃ | Br |
| 4-F | Br |
| 5-F | Br |
| 6-F | Br |
| 7-F | Br |
| 4-Cl | Br |
| 5-Cl | Br |
| 6-Cl | Br |
| 7-Cl | Br |
| 4-Br | Br |
| 5-Br | Br |
| 6-Br | Br |
| 7-Br | Br |
| 4-OCHF₂ | Br |
| 5OCHF₂ | Br |
| 6-OCHF₂ | Br |
| 7-OCHF₂ | Br |
| 4-(C≡CH) | Br |
| 5-(C≡CH) | Br |
| 6-(C≡CH) | Br |

TABLE 1-continued

X is S, R¹ is Me, R² is Me, and Pyr is 2-pyridinyl.

| (R³)ₙ | R⁴ |
|---|---|
| 7-(C≡CH) | Br |
| 4,5-di-Me | Br |
| 4,6-di-Me | Br |
| 4,7-di-Me | Br |
| 5,6-di-Me | Br |
| 5,7-di-Me | Br |
| 5-Cl, 7-Me | Br |
| 5-Cl, 7-OMe | Br |
| 5-F, 7-Me | Br |
| 5-Me, 7-F | Br |
| 5-Me, 7-Cl | Br |
| 5-Me, 7-CN | Br |
| 5-Me, 7-OMe | Br |
| 5-(C≡CH), 7-Me | Br |
| 5,7-di-F | Br |
| 5,7-di-Cl | Br |
| 5,7-di-Br | Br |
| — | OMe |
| 4-Me | OMe |
| 5-Me | OMe |
| 6-Me | OMe |
| 7-Me | OMe |
| 4-Et | OMe |
| 5-Et | OMe |
| 6-Et | OMe |
| 7-Et | OMe |
| 4-Pr | OMe |
| 5-Pr | OMe |
| 6-Pr | OMe |
| 7-Pr | OMe |
| 4-OMe | OMe |
| 5-OMe | OMe |
| 6-OMe | OMe |
| 7-OMe | OMe |
| 4-CN | OMe |
| 5-CN | OMe |
| 6-CN | OMe |
| 7-CN | OMe |
| 4-CF₃ | OMe |
| 5-CF₃ | OMe |
| 6-CF₃ | OMe |
| 7-CF₃ | OMe |
| 4-F | OMe |
| 5-F | OMe |
| 6-F | OMe |
| 7-F | OMe |
| 4-Cl | OMe |
| 5-Cl | OMe |
| 6-Cl | OMe |
| 7-Cl | OMe |
| 4-Br | OMe |
| 5-Br | OMe |
| 6-Br | OMe |
| 7-Br | OMe |
| 4-OCHF₂ | OMe |
| 5OCHF₂ | OMe |
| 6-OCHF₂ | OMe |
| 7-OCHF₂ | OMe |
| 4-(C≡CH) | OMe |
| 5-(C≡CH) | OMe |
| 6-(C≡CH) | OMe |
| 7-(C≡CH) | OMe |
| 4,5-di-Me | OMe |
| 4,6-di-Me | OMe |
| 4,7-di-Me | OMe |
| 5,6-di-Me | OMe |
| 5,7-di-Me | OMe |
| 5-Cl, 7-Me | OMe |
| 5-Cl, 7-OMe | OMe |
| 5-F, 7-Me | OMe |
| 5-Me, 7-F | OMe |
| 5-Me, 7-Cl | OMe |
| 5-Me, 7-CN | OMe |
| 5-Me, 7-OMe | OMe |
| 5-(C≡CH), 7-Me | OMe |
| 5,7-di-F | OMe |
| 5,7-di-Cl | OMe |
| 5,7-di-Br | OMe |
| — | SCHF₂ |
| 4-Me | SCHF₂ |
| 5-Me | SCHF₂ |
| 6-Me | SCHF₂ |
| 7-Me | SCHF₂ |
| 4-Et | SCHF₂ |
| 5-Et | SCHF₂ |
| 6-Et | SCHF₂ |
| 7-Et | SCHF₂ |
| 4-Pr | SCHF₂ |
| 5-Pr | SCHF₂ |
| 6-Pr | SCHF₂ |
| 7-Pr | SCHF₂ |
| 4-OMe | SCHF₂ |
| 5-OMe | SCHF₂ |
| 6-OMe | SCHF₂ |
| 7-OMe | SCHF₂ |
| 4-CN | SCHF₂ |
| 5-CN | SCHF₂ |
| 6-CN | SCHF₂ |
| 7-CN | SCHF₂ |
| 4-CF₃ | SCHF₂ |
| 5-CF₃ | SCHF₂ |
| 6-CF₃ | SCHF₂ |
| 7-CF₃ | SCHF₂ |
| 4-F | SCHF₂ |
| 5-F | SCHF₂ |
| 6-F | SCHF₂ |
| 7-F | SCHF₂ |
| 4-Cl | SCHF₂ |
| 5-Cl | SCHF₂ |
| 6-Cl | SCHF₂ |
| 7-Cl | SCHF₂ |
| 4-Br | SCHF₂ |
| 5-Br | SCHF₂ |
| 6-Br | SCHF₂ |
| 7-Br | SCHF₂ |
| 4-OCHF₂ | SCHF₂ |
| 5OCHF₂ | SCHF₂ |
| 6-OCHF₂ | SCHF₂ |
| 7-OCHF₂ | SCHF₂ |
| 4-(C≡CH) | SCHF₂ |
| 5-(C≡CH) | SCHF₂ |
| 6-(C≡CH) | SCHF₂ |
| 7-(C≡CH) | SCHF₂ |
| 4,5-di-Me | SCHF₂ |
| 4,6-di-Me | SCHF₂ |
| 4,7-di-Me | SCHF₂ |
| 5,6-di-Me | SCHF₂ |
| 5,7-di-Me | SCHF₂ |

TABLE 1-continued

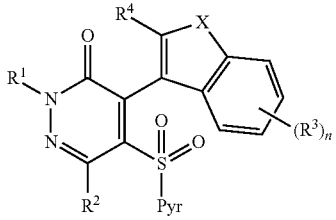

X is S, R¹ is Me, R² is Me, and Pyr is 2-pyridinyl.

| (R³)ₙ | R⁴ |
|---|---|
| 5-Cl, 7-Me | SCHF₂ |
| 5-Cl, 7-OMe | SCHF₂ |
| 5-F, 7-Me | SCHF₂ |
| 5-Me, 7-F | SCHF₂ |
| 5-Me, 7-Cl | SCHF₂ |
| 5-Me, 7-CN | SCHF₂ |
| 5-Me, 7-OMe | SCHF₂ |
| 5-(C≡CH), 7-Me | SCHF₂ |
| 5,7-di-F | SCHF₂ |
| 5,7-di-Cl | SCHF₂ |
| 5,7-di-Br | SCHF₂ |
| — | Me |
| 4-Me | Me |
| 5-Me | Me |
| 6-Me | Me |
| 7-Me | Me |
| 4-Et | Me |
| 5-Et | Me |
| 6-Et | Me |
| 7-Et | Me |
| 4-Pr | Me |
| 5-Pr | Me |
| 6-Pr | Me |
| 7-Pr | Me |
| 4-OMe | Me |
| 5-OMe | Me |
| 6-OMe | Me |
| 7-OMe | Me |
| 4-CN | Me |
| 5-CN | Me |
| 6-CN | Me |
| 7-CN | Me |
| 4-CF₃ | Me |
| 5-CF₃ | Me |
| 6-CF₃ | Me |
| 7-CF₃ | Me |
| 4-F | Me |
| 5-F | Me |
| 6-F | Me |
| 7-F | Me |
| 4-Cl | Me |
| 5-Cl | Me |
| 6-Cl | Me |
| 7-Cl | Me |
| 4-Br | Me |
| 5-Br | Me |
| 6-Br | Me |
| 7-Br | Me |
| 4-OCHF₂ | Me |
| 5OCHF₂ | Me |
| 6-OCHF₂ | Me |
| 7-OCHF₂ | Me |
| 4-(C≡CH) | Me |
| 5-(C≡CH) | Me |
| 6-(C≡CH) | Me |
| 7-(C≡CH) | Me |
| 4,5-di-Me | Me |
| 4,6-di-Me | Me |
| 4,7-di-Me | Me |
| 5,6-di-Me | Me |
| 5,7-di-Me | Me |
| 5-Cl, 7-Me | Me |
| 5-Cl, 7-OMe | Me |
| 5-F, 7-Me | Me |

TABLE 1-continued

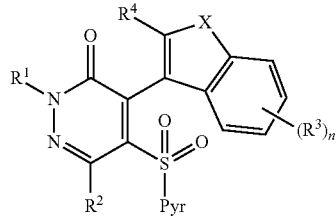

X is S, R¹ is Me, R² is Me, and Pyr is 2-pyridinyl.

| (R³)ₙ | R⁴ |
|---|---|
| 5-Me, 7-F | Me |
| 5-Me, 7-Cl | Me |
| 5-Me, 7-CN | Me |
| 5-Me, 7-OMe | Me |
| 5-(C≡CH), 7-Me | Me |
| 5,7-di-F | Me |
| 5,7-di-Cl | Me |
| 5,7-di-Br | Me |
| — | F |
| 4-Me | F |
| 5-Me | F |
| 6-Me | F |
| 7-Me | F |
| 4-Et | F |
| 5-Et | F |
| 6-Et | F |
| 7-Et | F |
| 4-Pr | F |
| 5-Pr | F |
| 6-Pr | F |
| 7-Pr | F |
| 4-OMe | F |
| 5-OMe | F |
| 6-OMe | F |
| 7-OMe | F |
| 4-CN | F |
| 5-CN | F |
| 6-CN | F |
| 7-CN | F |
| 4-CF₃ | F |
| 5-CF₃ | F |
| 6-CF₃ | F |
| 7-CF₃ | F |
| 4-F | F |
| 5-F | F |
| 6-F | F |
| 7-F | F |
| 4-Cl | F |
| 5-Cl | F |
| 6-Cl | F |
| 7-Cl | F |
| 4-Br | F |
| 5-Br | F |
| 6-Br | F |
| 7-Br | F |
| 4-OCHF₂ | F |
| 5OCHF₂ | F |
| 6-OCHF₂ | F |
| 7-OCHF₂ | F |
| 4-(C≡CH) | F |
| 5-(C≡CH) | F |
| 6-(C≡CH) | F |
| 7-(C≡CH) | F |
| 4,5-di-Me | F |
| 4,6-di-Me | F |
| 4,7-di-Me | F |
| 5,6-di-Me | F |
| 5,7-di-Me | F |
| 5-Cl, 7-Me | F |
| 5-Cl, 7-OMe | F |
| 5-F, 7-Me | F |
| 5-Me, 7-F | F |
| 5-Me, 7-Cl | F |
| 5-Me, 7-CN | F |

TABLE 1-continued

X is S, R¹ is Me, R² is Me, and Pyr is 2-pyridinyl.

| (R³)ₙ | R⁴ |
|---|---|
| 5-Me, 7-OMe | F |
| 5-(C≡CH), 7-Me | F |
| 5,7-di-F | F |
| 5,7-di-Cl | F |
| 5,7-di-Br | F |
| — | CN |
| 4-Me | CN |
| 5-Me | CN |
| 6-Me | CN |
| 7-Me | CN |
| 4-Et | CN |
| 5-Et | CN |
| 6-Et | CN |
| 7-Et | CN |
| 4-Pr | CN |
| 5-Pr | CN |
| 6-Pr | CN |
| 7-Pr | CN |
| 4-OMe | CN |
| 5-OMe | CN |
| 6-OMe | CN |
| 7-OMe | CN |
| 4-CN | CN |
| 5-CN | CN |
| 6-CN | CN |
| 7-CN | CN |
| 4-CF₃ | CN |
| 5-CF₃ | CN |
| 6-CF₃ | CN |
| 7-CF₃ | CN |
| 4-F | CN |
| 5-F | CN |
| 6-F | CN |
| 7-F | CN |
| 4-Cl | CN |
| 5-Cl | CN |
| 6-Cl | CN |
| 7-Cl | CN |
| 4-Br | CN |
| 5-Br | CN |
| 6-Br | CN |
| 7-Br | CN |
| 4-OCHF₂ | CN |
| 5OCHF₂ | CN |
| 6-OCHF₂ | CN |
| 7-OCHF₂ | CN |
| 4-(C≡CH) | CN |
| 5-(C≡CH) | CN |
| 6-(C≡CH) | CN |
| 7-(C≡CH) | CN |
| 4,5-di-Me | CN |
| 4,6-di-Me | CN |
| 4,7-di-Me | CN |
| 5,6-di-Me | CN |
| 5,7-di-Me | CN |
| 5-Cl, 7-Me | CN |
| 5-Cl, 7-OMe | CN |
| 5-F, 7-Me | CN |
| 5-Me, 7-F | CN |
| 5-Me, 7-Cl | CN |
| 5-Me, 7-CN | CN |
| 5-Me, 7-OMe | CN |
| 5-(C≡CH), 7-Me | CN |
| 5,7-di-F | CN |
| 5,7-di-Cl | CN |
| 5,7-di-Br | CN |
| — | OCHF₂ |
| 4-Me | OCHF₂ |
| 5-Me | OCHF₂ |
| 6-Me | OCHF₂ |
| 7-Me | OCHF₂ |
| 4-Et | OCHF₂ |
| 5-Et | OCHF₂ |
| 6-Et | OCHF₂ |
| 7-Et | OCHF₂ |
| 4-Pr | OCHF₂ |
| 5-Pr | OCHF₂ |
| 6-Pr | OCHF₂ |
| 7-Pr | OCHF₂ |
| 4-OMe | OCHF₂ |
| 5-OMe | OCHF₂ |
| 6-OMe | OCHF₂ |
| 7-OMe | OCHF₂ |
| 4-CN | OCHF₂ |
| 5-CN | OCHF₂ |
| 6-CN | OCHF₂ |
| 7-CN | OCHF₂ |
| 4-CF₃ | OCHF₂ |
| 5-CF₃ | OCHF₂ |
| 6-CF₃ | OCHF₂ |
| 7-CF₃ | OCHF₂ |
| 4-F | OCHF₂ |
| 5-F | OCHF₂ |
| 6-F | OCHF₂ |
| 7-F | OCHF₂ |
| 4-Cl | OCHF₂ |
| 5-Cl | OCHF₂ |
| 6-Cl | OCHF₂ |
| 7-Cl | OCHF₂ |
| 4-Br | OCHF₂ |
| 5-Br | OCHF₂ |
| 6-Br | OCHF₂ |
| 7-Br | OCHF₂ |
| 4-OCHF₂ | OCHF₂ |
| 5OCHF₂ | OCHF₂ |
| 6-OCHF₂ | OCHF₂ |
| 7-OCHF₂ | OCHF₂ |
| 4-(C≡CH) | OCHF₂ |
| 5-(C≡CH) | OCHF₂ |
| 6-(C≡CH) | OCHF₂ |
| 7-(C≡CH) | OCHF₂ |
| 4,5-di-Me | OCHF₂ |
| 4,6-di-Me | OCHF₂ |
| 4,7-di-Me | OCHF₂ |
| 5,6-di-Me | OCHF₂ |
| 5,7-di-Me | OCHF₂ |
| 5-Cl, 7-Me | OCHF₂ |
| 5-Cl, 7-OMe | OCHF₂ |
| 5-F, 7-Me | OCHF₂ |
| 5-Me, 7-F | OCHF₂ |
| 5-Me, 7-Cl | OCHF₂ |
| 5-Me, 7-CN | OCHF₂ |
| 5-Me, 7-OMe | OCHF₂ |
| 5-(C≡CH), 7-Me | OCHF₂ |
| 5,7-di-F | OCHF₂ |
| 5,7-di-Cl | OCHF₂ |
| 5,7-di-Br | OCHF₂ |
| — | SCF₃ |

TABLE 1-continued

X is S, R¹ is Me, R² is Me, and Pyr is 2-pyridinyl.

| (R³)ₙ | R⁴ |
|---|---|
| 4-Me | SCF₃ |
| 5-Me | SCF₃ |
| 6-Me | SCF₃ |
| 7-Me | SCF₃ |
| 4-Et | SCF₃ |
| 5-Et | SCF₃ |
| 6-Et | SCF₃ |
| 7-Et | SCF₃ |
| 4-Pr | SCF₃ |
| 5-Pr | SCF₃ |
| 6-Pr | SCF₃ |
| 7-Pr | SCF₃ |
| 4-OMe | SCF₃ |
| 5-OMe | SCF₃ |
| 6-OMe | SCF₃ |
| 7-OMe | SCF₃ |
| 4-CN | SCF₃ |
| 5-CN | SCF₃ |
| 6-CN | SCF₃ |
| 7-CN | SCF₃ |
| 4-CF₃ | SCF₃ |
| 5-CF₃ | SCF₃ |
| 6-CF₃ | SCF₃ |
| 7-CF₃ | SCF₃ |
| 4-F | SCF₃ |
| 5-F | SCF₃ |
| 6-F | SCF₃ |
| 7-F | SCF₃ |
| 4-Cl | SCF₃ |
| 5-Cl | SCF₃ |
| 6-Cl | SCF₃ |
| 7-Cl | SCF₃ |
| 4-Br | SCF₃ |
| 5-Br | SCF₃ |
| 6-Br | SCF₃ |
| 7-Br | SCF₃ |
| 4-OCHF₂ | SCF₃ |
| 5OCHF₂ | SCF₃ |
| 6-OCHF₂ | SCF₃ |
| 7-OCHF₂ | SCF₃ |
| 4-(C≡CH) | SCF₃ |
| 5-(C≡CH) | SCF₃ |
| 6-(C≡CH) | SCF₃ |
| 7-(C≡CH) | SCF₃ |
| 4,5-di-Me | SCF₃ |
| 4,6-di-Me | SCF₃ |
| 4,7-di-Me | SCF₃ |
| 5,6-di-Me | SCF₃ |
| 5,7-di-Me | SCF₃ |
| 5-Cl, 7-Me | SCF₃ |
| 5-Cl, 7-OMe | SCF₃ |
| 5-F, 7-Me | SCF₃ |
| 5-Me, 7-F | SCF₃ |
| 5-Me, 7-Cl | SCF₃ |
| 5-Me, 7-CN | SCF₃ |
| 5-Me, 7-OMe | SCF₃ |
| 5-(C≡CH), 7-Me | SCF₃ |
| 5,7-di-F | SCF₃ |
| 5,7-di-Cl | SCF₃ |
| 5,7-di-Br | SCF₃ |
| — | Et |
| 4-Me | Et |
| 5-Me | Et |
| 6-Me | Et |
| 7-Me | Et |
| 4-Et | Et |
| 5-Et | Et |
| 6-Et | Et |
| 7-Et | Et |
| 4-Pr | Et |
| 5-Pr | Et |
| 6-Pr | Et |
| 7-Pr | Et |
| 4-OMe | Et |
| 5-OMe | Et |
| 6-OMe | Et |
| 7-OMe | Et |
| 4-CN | Et |
| 5-CN | Et |
| 6-CN | Et |
| 7-CN | Et |
| 4-CF₃ | Et |
| 5-CF₃ | Et |
| 6-CF₃ | Et |
| 7-CF₃ | Et |
| 4-F | Et |
| 5-F | Et |
| 6-F | Et |
| 7-F | Et |
| 4-Cl | Et |
| 5-Cl | Et |
| 6-Cl | Et |
| 7-Cl | Et |
| 4-Br | Et |
| 5-Br | Et |
| 6-Br | Et |
| 7-Br | Et |
| 4-OCHF₂ | Et |
| 5OCHF₂ | Et |
| 6-OCHF₂ | Et |
| 7-OCHF₂ | Et |
| 4-(C≡CH) | Et |
| 5-(C≡CH) | Et |
| 6-(C≡CH) | Et |
| 7-(C≡CH) | Et |
| 4,5-di-Me | Et |
| 4,6-di-Me | Et |
| 4,7-di-Me | Et |
| 5,6-di-Me | Et |
| 5,7-di-Me | Et |
| 5-Cl, 7-Me | Et |
| 5-Cl, 7-OMe | Et |
| 5-F, 7-Me | Et |
| 5-Me, 7-F | Et |
| 5-Me, 7-Cl | Et |
| 5-Me, 7-CN | Et |
| 5-Me, 7-OMe | Et |
| 5-(C≡CH), 7-Me | Et |
| 5,7-di-F | Et |
| 5,7-di-Cl | Et |
| 5,7-di-Br | Et |
| — | Cl |
| 4-Me | Cl |
| 5-Me | Cl |
| 6-Me | Cl |
| 7-Me | Cl |
| 4-Et | Cl |
| 5-Et | Cl |

TABLE 1-continued

X is S, R¹ is Me, R² is Me, and Pyr is 2-pyridinyl.

| $(R^3)_n$ | $R^4$ |
|---|---|
| 6-Et | Cl |
| 7-Et | Cl |
| 4-Pr | Cl |
| 5-Pr | Cl |
| 6-Pr | Cl |
| 7-Pr | Cl |
| 4-OMe | Cl |
| 5-OMe | Cl |
| 6-OMe | Cl |
| 7-OMe | Cl |
| 4-CN | Cl |
| 5-CN | Cl |
| 6-CN | Cl |
| 7-CN | Cl |
| 4-CF$_3$ | Cl |
| 5-CF$_3$ | Cl |
| 6-CF$_3$ | Cl |
| 7-CF$_3$ | Cl |
| 4-F | Cl |
| 5-F | Cl |
| 6-F | Cl |
| 7-F | Cl |
| 4-Cl | Cl |
| 5-Cl | Cl |
| 6-Cl | Cl |
| 7-Cl | Cl |
| 4-Br | Cl |
| 5-Br | Cl |
| 6-Br | Cl |
| 7-Br | Cl |
| 4-OCHF$_2$ | Cl |
| 5OCHF$_2$ | Cl |
| 6-OCHF$_2$ | Cl |
| 7-OCHF$_2$ | Cl |
| 4-(C≡CH) | Cl |
| 5-(C≡CH) | Cl |
| 6-(C≡CH) | Cl |
| 7-(C≡CH) | Cl |
| 4,5-di-Me | Cl |
| 4,6-di-Me | Cl |
| 4,7-di-Me | Cl |
| 5,6-di-Me | Cl |
| 5,7-di-Me | Cl |
| 5-Cl, 7-Me | Cl |
| 5-Cl, 7-OMe | Cl |
| 5-F, 7-Me | Cl |
| 5-Me, 7-F | Cl |
| 5-Me, 7-Cl | Cl |
| 5-Me, 7-CN | Cl |
| 5-Me, 7-OMe | Cl |
| 5-(C≡CH), 7-Me | Cl |
| 5,7-di-F | Cl |
| 5,7-di-Cl | Cl |
| 5,7-di-Br | Cl |
| — | C≡CH |
| 4-Me | C≡CH |
| 5-Me | C≡CH |
| 6-Me | C≡CH |
| 7-Me | C≡CH |
| 4-Et | C≡CH |
| 5-Et | C≡CH |
| 6-Et | C≡CH |
| 7-Et | C≡CH |
| 4-Pr | C≡CH |
| 5-Pr | C≡CH |
| 6-Pr | C≡CH |
| 7-Pr | C≡CH |
| 4-OMe | C≡CH |
| 5-OMe | C≡CH |
| 6-OMe | C≡CH |
| 7-OMe | C≡CH |
| 4-CN | C≡CH |
| 5-CN | C≡CH |
| 6-CN | C≡CH |
| 7-CN | C≡CH |
| 4-CF$_3$ | C≡CH |
| 5-CF$_3$ | C≡CH |
| 6-CF$_3$ | C≡CH |
| 7-CF$_3$ | C≡CH |
| 4-F | C≡CH |
| 5-F | C≡CH |
| 6-F | C≡CH |
| 7-F | C≡CH |
| 4-Cl | C≡CH |
| 5-Cl | C≡CH |
| 6-Cl | C≡CH |
| 7-Cl | C≡CH |
| 4-Br | C≡CH |
| 5-Br | C≡CH |
| 6-Br | C≡CH |
| 7-Br | C≡CH |
| 4-OCHF$_2$ | C≡CH |
| 5OCHF$_2$ | C≡CH |
| 6-OCHF$_2$ | C≡CH |
| 7-OCHF$_2$ | C≡CH |
| 4-(C≡CH) | C≡CH |
| 5-(C≡CH) | C≡CH |
| 6-(C≡CH) | C≡CH |
| 7-(C≡CH) | C≡CH |
| 4,5-di-Me | C≡CH |
| 4,6-di-Me | C≡CH |
| 4,7-di-Me | C≡CH |
| 5,6-di-Me | C≡CH |
| 5,7-di-Me | C≡CH |
| 5-Cl, 7-Me | C≡CH |
| 5-Cl, 7-OMe | C≡CH |
| 5-F, 7-Me | C≡CH |
| 5-Me, 7-F | C≡CH |
| 5-Me, 7-Cl | C≡CH |
| 5-Me, 7-CN | C≡CH |
| 5-Me, 7-OMe | C≡CH |
| 5-(C≡CH), 7-Me | C≡CH |
| 5,7-di-F | C≡CH |
| 5,7-di-Cl | C≡CH |
| 5,7-di-Br | C≡CH |
| — | SMe |
| 4-Me | SMe |
| 5-Me | SMe |
| 6-Me | SMe |
| 7-Me | SMe |
| 4-Et | SMe |
| 5-Et | SMe |
| 6-Et | SMe |
| 7-Et | SMe |
| 4-Pr | SMe |
| 5-Pr | SMe |
| 6-Pr | SMe |
| 7-Pr | SMe |

TABLE 1-continued

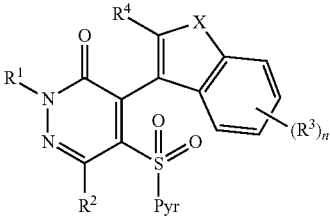

X is S, R¹ is Me, R² is Me, and Pyr is 2-pyridinyl.

| $(R^3)_n$ | $R^4$ |
|---|---|
| 4-OMe | SMe |
| 5-OMe | SMe |
| 6-OMe | SMe |
| 7-OMe | SMe |
| 4-CN | SMe |
| 5-CN | SMe |
| 6-CN | SMe |
| 7-CN | SMe |
| 4-CF₃ | SMe |
| 5-CF₃ | SMe |
| 6-CF₃ | SMe |
| 7-CF₃ | SMe |
| 4-F | SMe |
| 5-F | SMe |
| 6-F | SMe |
| 7-F | SMe |
| 4-Cl | SMe |
| 5-Cl | SMe |
| 6-Cl | SMe |
| 7-Cl | SMe |
| 4-Br | SMe |
| 5-Br | SMe |
| 6-Br | SMe |
| 7-Br | SMe |
| 4-OCHF₂ | SMe |
| 5-OCHF₂ | SMe |
| 6-OCHF₂ | SMe |
| 7-OCHF₂ | SMe |
| 4-(C≡CH) | SMe |

TABLE 1-continued

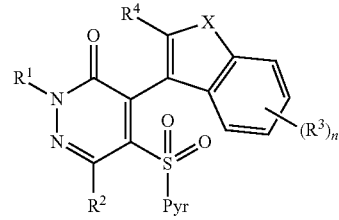

X is S, R¹ is Me, R² is Me, and Pyr is 2-pyridinyl.

| $(R^3)_n$ | $R^4$ |
|---|---|
| 5-(C≡CH) | SMe |
| 6-(C≡CH) | SMe |
| 7-(C≡CH) | SMe |
| 4,5-di-Me | SMe |
| 4,6-di-Me | SMe |
| 4,7-di-Me | SMe |
| 5,6-di-Me | SMe |
| 5,7-di-Me | SMe |
| 5-Cl, 7-Me | SMe |
| 5-Cl, 7-OMe | SMe |
| 5-F, 7-Me | SMe |
| 5-Me, 7-F | SMe |
| 5-Me, 7-Cl | SMe |
| 5-Me, 7-CN | SMe |
| 5-Me, 7-OMe | SMe |
| 5-(C≡CH), 7-Me | SMe |
| 5,7-di-F | SMe |
| 5,7-di-Cl | SMe |
| 5,7-di-Br | SMe |

Table 2 is constructed in the same manner except that the Row Heading "X is S, R¹ is Me and R² is Me." is replaced with the Row Heading listed for Table 2 below (i.e. "X is S, R¹ is Me and R² is Me."). Therefore the first entry in Table 2 is a compound of Formula 1 wherein X is S, R¹ is Me, R² is Me, $(R^3)_n$ is "-" (i.e. n is 0; no substitution with R³) and R⁴ is H. Tables 3 through 643 are constructed similarly.

| Table | Row Heading |
|---|---|
| 2 | X is S, R¹ is Me, R² is Me, and Pyr is 3-pyridinyl. |
| 3 | X is S, R¹ is Me, R² is Me, and Pyr is 4-pyridinyl. |
| 4 | X is S, R¹ is Me, R² is Me, and Pyr is 2-pyridinyl(3-CH₃). |
| 5 | X is S, R¹ is Me, R² is Me, and Pyr is 2-pyridinyl(4-CH₃). |
| 6 | X is S, R¹ is Me, R₂ is Me, and Pyr is 3-pyridinyl(2-CH₃). |
| 7 | X is S, R¹ is Me, R² is Me, and Pyr is 3-pyridinyl(4-CH₃). |
| 8 | X is S, R¹ is Me, R₂ is Me, and Pyr is 2-pyridinyl(3-Cl). |
| 9 | X is S, R¹ is Me, R² is Me, and Pyr is 2-pyridinyl(4-Cl). |
| 10 | X is S, R¹ is Me, R² is Me, and Pyr is 3-pyridinyl(5-Cl). |
| 11 | X is S, R¹ is Me, R² is H, and Pyr is 2-pyridinyl. |
| 12 | X is S, R¹ is Me, R² is H, and Pyr is 3-pyridinyl. |
| 13 | X is S, R¹ is Me, R² is H, and Pyr is 4-pyridinyl. |
| 14 | X is S, R¹ is Me, R² is H, and Pyr is 2-pyridinyl(3-CH₃). |
| 15 | X is S, R¹ is Me, R² is H, and Pyr is 2-pyridinyl(4-CH₃). |
| 16 | X is S, R¹ is Me, R² is H, and Pyr is 3-pyridinyl(2-CH₃). |
| 17 | X is S, R¹ is Me, R² is H, and Pyr is 3-pyridinyl(4-CH₃). |
| 18 | X is S, R¹ is Me, R² is H, and Pyr is 2-pyridinyl(3-Cl). |
| 19 | X is S, R¹ is Me, R² is H, and Pyr is 2-pyridinyl(4-Cl). |
| 20 | X is S, R¹ is Me, R² is H, and Pyr is 3-pyridinyl(5-Cl). |
| 21 | X is S, R¹ is Me, R² is Et, and Pyr is 2-pyridinyl. |
| 22 | X is S, R¹ is Me, R² is Et, and Pyr is 3-pyridinyl. |
| 23 | X is S, R¹ is Me, R² is Et, and Pyr is 4-pyridinyl. |
| 24 | X is S, R¹ is Me, R² is Et, and Pyr is 2-pyridinyl(3-CH₃). |
| 25 | X is S, R¹ is Me, R² is Et, and Pyr is 2-pyridinyl(4-CH₃). |
| 26 | X is S, R¹ is Me, R² is Et, and Pyr is 3-pyridinyl(2-CH₃). |
| 27 | X is S, R¹ is Me, R² is Et, and Pyr is 3-pyridinyl(4-CH₃). |
| 28 | X is S, R¹ is Me, R² is Et, and Pyr is 2-pyridinyl(3-Cl). |
| 29 | X is S, R¹ is Me, R² is Et, and Pyr is 2-pyridinyl(4-Cl). |
| 30 | X is S, R¹ is Me, R² is Et, and Pyr is 3-pyridinyl(5-Cl). |
| 31 | X is S, R¹ is Me, R² is Pr, and Pyr is 2-pyridinyl. |

-continued

| Table | Row Heading |
|---|---|
| 32 | X is S, $R^1$ is Me, $R^2$ is Pr, and Pyr is 3-pyridinyl. |
| 33 | X is S, $R^1$ is Me, $R^2$ is Pr, and Pyr is 4-pyridinyl. |
| 34 | X is S, $R^1$ is Me, $R^2$ is Pr, and Pyr is 2-pyridinyl(3-$CH_3$). |
| 35 | X is S, $R^1$ is Me, $R^2$ is Pr, and Pyr is 2-pyridinyl(4-$CH_3$). |
| 36 | X is S, $R^1$ is Me, $R^2$ is Pr, and Pyr is 3-pyridinyl(2-$CH_3$). |
| 37 | X is S, $R^1$ is Me, $R^2$ is Pr, and Pyr is 3-pyridinyl(4-$CH_3$). |
| 38 | X is S, $R^1$ is Me, $R^2$ is Pr, and Pyr is 2-pyridinyl(3-Cl). |
| 39 | X is S, $R^1$ is Me, $R^2$ is Pr, and Pyr is 2-pyridinyl(4-Cl). |
| 40 | X is S, $R^1$ is Me, $R^2$ is Pr, and Pyr is 3-pyridinyl(5-Cl). |
| 41 | X is S, $R^1$ is Me, $R^2$ is $CF_3$, and Pyr is 2-pyridinyl. |
| 42 | X is S, $R^1$ is Me, $R^2$ is $CF_3$, and Pyr is 3-pyridinyl. |
| 43 | X is S, $R^1$ is Me, $R^2$ is $CF_3$, and Pyr is 4-pyridinyl. |
| 44 | X is S, $R^1$ is Me, $R^2$ is $CF_3$, and Pyr is 2-pyridinyl(3-$CH_3$). |
| 45 | X is S, $R^1$ is Me, $R^2$ is $CF_3$, and Pyr is 2-pyridinyl(4-$CH_3$). |
| 46 | X is S, $R^1$ is Me, $R^2$ is $CF_3$, and Pyr is 3-pyridinyl(2-$CH_3$). |
| 47 | X is S, $R^1$ is Me, $R^2$ is $CF_3$, and Pyr is 3-pyridinyl(4-$CH_3$). |
| 48 | X is S, $R^1$ is Me, $R^2$ is $CF_3$, and Pyr is 2-pyridinyl(3-Cl). |
| 49 | X is S, $R^1$ is Me, $R^2$ is $CF_3$, and Pyr is 2-pyridinyl(4-Cl). |
| 50 | X is S, $R^1$ is Me, $R^2$ is $CF_3$, and Pyr is 3-pyridinyl(5-Cl). |
| 51 | X is S, $R^1$ is Me, $R^2$ is Cl, and Pyr is 2-pyridinyl. |
| 52 | X is S, $R^1$ is Me, $R^2$ is Cl, and Pyr is 3-pyridinyl. |
| 53 | X is S, $R^1$ is Me, $R^2$ is Cl, and Pyr is 4-pyridinyl. |
| 54 | X is S, $R^1$ is Me, $R^2$ is Cl, and Pyr is 2-pyridinyl(3-$CH_3$). |
| 55 | X is S, $R^1$ is Me, $R^2$ is Cl, and Pyr is 2-pyridinyl(4-$CH_3$). |
| 56 | X is S, $R^1$ is Me, $R^2$ is Cl, and Pyr is 3-pyridinyl(2-$CH_3$). |
| 57 | X is S, $R^1$ is Me, $R^2$ is Cl, and Pyr is 3-pyridinyl(4-$CH_3$). |
| 58 | X is S, $R^1$ is Me, $R^2$ is Cl, and Pyr is 2-pyridinyl(3-Cl). |
| 59 | X is S, $R^1$ is Me, $R^2$ is Cl, and Pyr is 2-pyridinyl(4-Cl). |
| 60 | X is S, $R^1$ is Me, $R^2$ is Cl, and Pyr is 3-pyridinyl(5-Cl). |
| 61 | X is S, $R^1$ is Me, $R^2$ is Br, and Pyr is 2-pyridinyl. |
| 62 | X is S, $R^1$ is Me, $R^2$ is Br, and Pyr is 3-pyridinyl. |
| 63 | X is S, $R^1$ is Me, $R^2$ is Br, and Pyr is 4-pyridinyl. |
| 64 | X is S, $R^1$ is Me, $R^2$ is Br, and Pyr is 2-pyridinyl(3-$CH_3$). |
| 65 | X is S, $R^1$ is Me, $R^2$ is Br, and Pyr is 2-pyridinyl(4-$CH_3$). |
| 66 | X is S, $R^1$ is Me, $R^2$ is Br, and Pyr is 3-pyridinyl(2-$CH_3$). |
| 67 | X is S, $R^1$ is Me, $R^2$ is Br, and Pyr is 3-pyridinyl(4-$CH_3$). |
| 68 | X is S, $R^1$ is Me, $R^2$ is Br, and Pyr is 2-pyridinyl(3-Cl). |
| 69 | X is S, $R^1$ is Me, $R^2$ is Br, and Pyr is 2-pyridinyl(4-Cl). |
| 70 | X is S, $R^1$ is Me, $R^2$ is Br, and Pyr is 3-pyridinyl(5-Cl). |
| 71 | X is S, $R^1$ is Me, $R^2$ is I, and Pyr is 2-pyridinyl. |
| 72 | X is S, $R^1$ is Me, $R^2$ is I, and Pyr is 3-pyridinyl. |
| 73 | X is S, $R^1$ is Me, $R^2$ is I, and Pyr is 4-pyridinyl. |
| 74 | X is S, $R^1$ is Me, $R^2$ is I, and Pyr is 2-pyridinyl(3-$CH_3$). |
| 75 | X is S, $R^1$ is Me, $R^2$ is I, and Pyr is 2-pyridinyl(4-$CH_3$). |
| 76 | X is S, $R^1$ is Me, $R^2$ is I, and Pyr is 3-pyridinyl(2-$CH_3$). |
| 77 | X is S, $R^1$ is Me, $R^2$ is I, and Pyr is 3-pyridinyl(4-$CH_3$). |
| 78 | X is S, $R^1$ is Me, $R^2$ is I, and Pyr is 2-pyridinyl(3-Cl). |
| 79 | X is S, $R^1$ is Me, $R^2$ is I, and Pyr is 2-pyridinyl(4-Cl). |
| 80 | X is S, $R^1$ is Me, $R^2$ is I, and Pyr is 3-pyridinyl(5-Cl). |
| 81 | X is S, $R^1$ is Me, $R^2$ is OMe, and Pyr is 2-pyridinyl. |
| 82 | X is S, $R^1$ is Me, $R^2$ is OMe, and Pyr is 3-pyridinyl. |
| 83 | X is S, $R^1$ is Me, $R^2$ is OMe, and Pyr is 4-pyridinyl. |
| 84 | X is S, $R^1$ is Me, $R^2$ is OMe, and Pyr is 2-pyridinyl(3-$CH_3$). |
| 85 | X is S, $R^1$ is Me, $R^2$ is OMe, and Pyr is 2-pyridinyl(4-$CH_3$). |
| 86 | X is S, $R^1$ is Me, $R^2$ is OMe, and Pyr is 3-pyridinyl(2-$CH_3$). |
| 87 | X is S, $R^1$ is Me, $R^2$ is OMe, and Pyr is 3-pyridinyl(4-$CH_3$). |
| 88 | X is S, $R^1$ is Me, $R^2$ is OMe, and Pyr is 2-pyridinyl(3-Cl). |
| 89 | X is S, $R^1$ is Me, $R^2$ is OMe, and Pyr is 2-pyridinyl(4-Cl). |
| 90 | X is S, $R^1$ is Me, $R^2$ is OMe, and Pyr is 3-pyridinyl(5-Cl). |
| 91 | X is S, $R^1$ is Me, $R^2$ is OEt, and Pyr is 2-pyridinyl. |
| 92 | X is S, $R^1$ is Me, $R^2$ is OEt, and Pyr is 3-pyridinyl. |
| 93 | X is S, $R^1$ is Me, $R^2$ is OEt, and Pyr is 4-pyridinyl. |
| 94 | X is S, $R^1$ is Me, $R^2$ is OEt, and Pyr is 2-pyridinyl(3-$CH_3$). |
| 95 | X is S, $R^1$ is Me, $R^2$ is OEt, and Pyr is 2-pyridinyl(4-$CH_3$). |
| 96 | X is S, $R^1$ is Me, $R^2$ is OEt, and Pyr is 3-pyridinyl(2-$CH_3$). |
| 97 | X is S, $R^1$ is Me, $R^2$ is OEt, and Pyr is 3-pyridinyl(4-$CH_3$). |
| 98 | X is S, $R^1$ is Me, $R^2$ is OEt, and Pyr is 2-pyridinyl(3-Cl). |
| 99 | X is S, $R^1$ is Me, $R^2$ is OEt, and Pyr is 2-pyridinyl(4-Cl). |
| 100 | X is S, $R^1$ is Me, $R^2$ is OEt, and Pyr is 3-pyridinyl(5-Cl). |
| 101 | X is S, $R^1$ is Et, $R^2$ is Me, and Pyr is 2-pyridinyl. |
| 102 | X is S, $R^1$ is Et, $R^2$ is Me, and Pyr is 3-pyridinyl. |
| 103 | X is S, $R^1$ is Et, $R^2$ is Me, and Pyr is 4-pyridinyl. |
| 104 | X is S, $R^1$ is Et, $R^2$ is Me, and Pyr is 2-pyridinyl(3-$CH_3$). |
| 105 | X is S, $R^1$ is Et, $R^2$ is Me, and Pyr is 2-pyridinyl(4-$CH_3$). |
| 106 | X is S, $R^1$ is Et, $R^2$ is Me, and Pyr is 3-pyridinyl(2-$CH_3$). |
| 107 | X is S, $R^1$ is Et, $R^2$ is Me, and Pyr is 3-pyridinyl(4-$CH_3$). |
| 108 | X is S, $R^1$ is Et, $R^2$ is Me, and Pyr is 2-pyridinyl(3-Cl). |

| Table | Row Heading |
|---|---|
| 109 | X is S, $R^1$ is Et, $R^2$ is Me, and Pyr is 2-pyridinyl(4-Cl). |
| 110 | X is S, $R^1$ is Et, $R^2$ is Me, and Pyr is 3-pyridinyl(5-Cl). |
| 111 | X is S, $R^1$ is Et, $R^2$ is H, and Pyr is 2-pyridinyl. |
| 112 | X is S, $R^1$ is Et, $R^2$ is H, and Pyr is 3-pyridinyl. |
| 113 | X is S, $R^1$ is Et, $R^2$ is H, and Pyr is 4-pyridinyl. |
| 114 | X is S, $R^1$ is Et, $R^2$ is H, and Pyr is 2-pyridinyl(3-$CH_3$). |
| 115 | X is S, $R^1$ is Et, $R^2$ is H, and Pyr is 2-pyridinyl(4-$CH_3$). |
| 116 | X is S, $R^1$ is Et, $R^2$ is H, and Pyr is 3-pyridinyl(2-$CH_3$). |
| 117 | X is S, $R^1$ is Et, $R^2$ is H, and Pyr is 3-pyridinyl(4-$CH_3$). |
| 118 | X is S, $R^1$ is Et, $R^2$ is H, and Pyr is 2-pyridinyl(3-Cl). |
| 119 | X is S, $R^1$ is Et, $R^2$ is H, and Pyr is 2-pyridinyl(4-Cl). |
| 120 | X is S, $R^1$ is Et, $R^2$ is H, and Pyr is 3-pyridinyl(5-Cl). |
| 121 | X is S, $R^1$ is Et, $R^2$ is Et, and Pyr is 2-pyridinyl. |
| 122 | X is S, $R^1$ is Et, $R^2$ is Et, and Pyr is 3-pyridinyl. |
| 123 | X is S, $R^1$ is Et, $R^2$ is Et, and Pyr is 4-pyridinyl. |
| 124 | X is S, $R^1$ is Et, $R^2$ is Et, and Pyr is 2-pyridinyl(3-$CH_3$). |
| 125 | X is S, $R^1$ is Et, $R^2$ is Et, and Pyr is 2-pyridinyl(4-$CH_3$). |
| 126 | X is S, $R^1$ is Et, $R^2$ is Et, and Pyr is 3-pyridinyl(2-$CH_3$). |
| 127 | X is S, $R^1$ is Et, $R^2$ is Et, and Pyr is 3-pyridinyl(4-$CH_3$). |
| 128 | X is S, $R^1$ is Et, $R^2$ is Et, and Pyr is 2-pyridinyl(3-Cl). |
| 129 | X is S, $R^1$ is Et, $R^2$ is Et, and Pyr is 2-pyridinyl(4-Cl). |
| 130 | X is S, $R^1$ is Et, $R^2$ is Et, and Pyr is 3-pyridinyl(5-Cl). |
| 131 | X is S, $R^1$ is Et, $R^2$ is Pr, and Pyr is 2-pyridinyl. |
| 132 | X is S, $R^1$ is Et, $R^2$ is Pr, and Pyr is 3-pyridinyl. |
| 133 | X is S, $R^1$ is Et, $R^2$ is Pr, and Pyr is 4-pyridinyl. |
| 134 | X is S, $R^1$ is Et, $R^2$ is Pr, and Pyr is 2-pyridinyl(3-$CH_3$). |
| 135 | X is S, $R^1$ is Et, $R^2$ is Pr, and Pyr is 2-pyridinyl(4-$CH_3$). |
| 136 | X is S, $R^1$ is Et, $R^2$ is Pr, and Pyr is 3-pyridinyl(2-$CH_3$). |
| 137 | X is S, $R^1$ is Et, $R^2$ is Pr, and Pyr is 3-pyridinyl(4-$CH_3$). |
| 138 | X is S, $R^1$ is Et, $R^2$ is Pr, and Pyr is 2-pyridinyl(3-Cl). |
| 139 | X is S, $R^1$ is Et, $R^2$ is Pr, and Pyr is 2-pyridinyl(4-Cl). |
| 140 | X is S, $R^1$ is Et, $R^2$ is Pr, and Pyr is 3-pyridinyl(5-Cl). |
| 141 | X is S, $R^1$ is Et, $R^2$ is $CF_3$, and Pyr is 2-pyridinyl. |
| 142 | X is S, $R^1$ is Et, $R^2$ is $CF_3$, and Pyr is 3-pyridinyl. |
| 143 | X is S, $R^1$ is Et, $R^2$ is $CF_3$, and Pyr is 4-pyridinyl. |
| 144 | X is S, $R^1$ is Et, $R^2$ is $CF_3$, and Pyr is 2-pyridinyl(3-$CH_3$).). |
| 145 | X is S, $R^1$ is Et, $R^2$ is $CF_3$, and Pyr is 2-pyridinyl(4-$CH_3$). |
| 146 | X is S, $R^1$ is Et, $R^2$ is $CF_3$, and Pyr is 3-pyridinyl(2-$CH_3$). |
| 147 | X is S, $R^1$ is Et, $R^2$ is $CF_3$, and Pyr is 3-pyridinyl(4-$CH_3$). |
| 148 | X is S, $R^1$ is Et, $R^2$ is $CF_3$, and Pyr is 2-pyridinyl(3-Cl). |
| 149 | X is S, $R^1$ is Et, $R^2$ is $CF_3$, and Pyr is 2-pyridinyl(4-Cl). |
| 150 | X is S, $R^1$ is Et, $R^2$ is $CF_3$, and Pyr is 3-pyridinyl(5-Cl). |
| 151 | X is S, $R^1$ is Et, $R^2$ is Cl, and Pyr is 2-pyridinyl. |
| 152 | X is S, $R^1$ is Et, $R^2$ is Cl, and Pyr is 3-pyridinyl. |
| 153 | X is S, $R^1$ is Et, $R^2$ is Cl, and Pyr is 4-pyridinyl. |
| 154 | X is S, $R^1$ is Et, $R^2$ is Cl, and Pyr is 2-pyridinyl(3-$CH_3$). |
| 155 | X is S, $R^1$ is Et, $R^2$ is Cl, and Pyr is 2-pyridinyl(4-$CH_3$). |
| 156 | X is S, $R^1$ is Et, $R^2$ is Cl, and Pyr is 3-pyridinyl(2-$CH_3$). |
| 157 | X is S, $R^1$ is Et, $R^2$ is Cl, and Pyr is 3-pyridinyl(4-$CH_3$). |
| 158 | X is S, $R^1$ is Et, $R^2$ is Cl, and Pyr is 2-pyridinyl(3-Cl). |
| 159 | X is S, $R^1$ is Et, $R^2$ is Cl, and Pyr is 2-pyridinyl(4-Cl). |
| 160 | X is S, $R^1$ is Et, $R^2$ is Cl, and Pyr is 3-pyridinyl(5-Cl). |
| 161 | X is S, $R^1$ is Et, $R^2$ is Br, and Pyr is 2-pyridinyl. |
| 162 | X is S, $R^1$ is Et, $R^2$ is Br, and Pyr is 3-pyridinyl. |
| 163 | X is S, $R^1$ is Et, $R^2$ is Br, and Pyr is 4-pyridinyl. |
| 164 | X is S, $R^1$ is Et, $R^2$ is Br, and Pyr is 2-pyridinyl(3-$CH_3$). |
| 165 | X is S, $R^1$ is Et, $R^2$ is Br, and Pyr is 2-pyridinyl(4-$CH_3$). |
| 166 | X is S, $R^1$ is Et, $R^2$ is Br, and Pyr is 3-pyridinyl(2-$CH_3$). |
| 167 | X is S, $R^1$ is Et, $R^2$ is Br, and Pyr is 3-pyridinyl(4-$CH_3$). |
| 168 | X is S, $R^1$ is Et, $R^2$ is Br, and Pyr is 2-pyridinyl(3-Cl). |
| 169 | X is S, $R^1$ is Et, $R^2$ is Br, and Pyr is 2-nyridinyl(4-Cl). |
| 170 | X is S, $R^1$ is Et, $R^2$ is Br, and Pyr is 3-pyridinyl(5-Cl). |
| 171 | X is S, $R^1$ is Et, $R^2$ is I, and Pyr is 2-pyridinyl. |
| 172 | X is S, $R^1$ is Et, $R^2$ is I, and Pyr is 3-pyridinyl. |
| 173 | X is S, $R^1$ is Et, $R^2$ is I, and Pyr is 4-pyridinyl. |
| 174 | X is S, $R^1$ is Et, $R^2$ is I, and Pyr is 2-pyridinyl(3-$CH_3$). |
| 175 | X is S, $R^1$ is Et, $R^2$ is I, and Pyr is 2-pyridinyl(4-$CH_3$). |
| 176 | X is S, $R^1$ is Et, $R^2$ is I, and Pyr is 3-pyridinyl(2-$CH_3$). |
| 177 | X is S, $R^1$ is Et, $R^2$ is I, and Pyr is 3-pyridinyl(4-$CH_3$). |
| 178 | X is S, $R^1$ is Et, $R^2$ is I, and Pyr is 2-pyridinyl(3-Cl). |
| 179 | X is S, $R^1$ is Et, $R^2$ is I, and Pyr is 2-pyridinyl(4-Cl). |
| 180 | X is S, $R^1$ is Et, $R^2$ is I, and Pyr is 3-pyridinyl(5-Cl). |
| 181 | X is S, $R^1$ is Et, $R^2$ is OMe, and Pyr is 2-pyridinyl. |
| 182 | X is S, $R^1$ is Et, $R^2$ is OMe, and Pyr is 3-pyridinyl. |
| 183 | X is S, $R^1$ is Et, $R^2$ is OMe, and Pyr is 4-pyridinyl. |
| 184 | X is S, $R^1$ is Et, $R^2$ is OMe, and Pyr is 2-pyridinyl(3-$CH_3$). |
| 185 | X is S, $R^1$ is Et, $R^2$ is OMe, and Pyr is 2-pyridinyl(4-$CH_3$). |

| Table | Row Heading |
|---|---|
| 186 | X is S, $R^1$ is Et, $R^2$ is OMe, and Pyr is 3-pyridinyl(2-$CH_3$). |
| 187 | X is S, $R^1$ is Et, $R^2$ is OMe, and Pyr is 3-pyridinyl(4-$CH_3$). |
| 188 | X is S, $R^1$ is Et, $R^2$ is OMe, and Pyr is 2-pyridinyl(3-Cl). |
| 189 | X is S, $R^1$ is Et, $R^2$ is OMe, and Pyr is 2-pyridinyl(4-Cl). |
| 190 | X is S, $R^1$ is Et, $R^2$ is OMe, and Pyr is 3-pyridinyl(5-Cl). |
| 191 | X is S, $R^1$ is Et, $R^2$ is OEt, and Pyr is 2-pyridinyl. |
| 192 | X is S, $R^1$ is Et, $R^2$ is OEt, and Pyr is 3-pyridinyl. |
| 193 | X is S, $R^1$ is Et, $R^2$ is OEt, and Pyr is 4-pyridinyl. |
| 194 | X is S, $R^1$ is Et, $R^2$ is OEt, and Pyr is 2-pyridinyl(3-$CH_3$). |
| 195 | X is S, $R^1$ is Et, $R^2$ is OEt, and Pyr is 2-pyridinyl(4-$CH_3$). |
| 196 | X is S, $R^1$ is Et, $R^2$ is OEt, and Pyr is 3-pyridinyl(2-$CH_3$). |
| 197 | X is S, $R^1$ is Et, $R^2$ is OEt, and Pyr is 3-pyridinyl(4-$CH_3$). |
| 198 | X is S, $R^1$ is Et, $R^2$ is OEt, and Pyr is 2-pyridinyl(3-Cl). |
| 199 | X is S, $R^1$ is Et, $R^2$ is OEt, and Pyr is 2-pyridinyl(4-Cl). |
| 200 | X is S, $R^1$ is Et, $R^2$ is OEt, and Pyr is 3-pyridinyl(5-Cl). |
| 201 | X is S, $R^1$ is Pr, $R^2$ is Me, and Pyr is 2-pyridinyl. |
| 202 | X is S, $R^1$ is Pr, $R^2$ is Me, and Pyr is 3-pyridinyl. |
| 203 | X is S, $R^1$ is Pr, $R^2$ is Me, and Pyr is 4-pyridinyl. |
| 204 | X is S, $R^1$ is Pr, $R^2$ is Me, and Pyr is 2-pyridinyl(3-$CH_3$). |
| 205 | X is S, $R^1$ is Pr, $R^2$ is Me, and Pyr is 2-pyridinyl(4-$CH_3$). |
| 206 | X is S, $R^1$ is Pr, $R^2$ is Me, and Pyr is 3-pyridinyl(2-$CH_3$). |
| 207 | X is S, $R^1$ is Pr, $R^2$ is Me, and Pyr is 3-pyridinyl(4-$CH_3$). |
| 208 | X is S, $R^1$ is Pr, $R^2$ is Me, and Pyr is 2-pyridinyl(3-Cl). |
| 209 | X is S, $R^1$ is Pr, $R^2$ is Me, and Pyr is 2-pyridinyl(4-Cl). |
| 210 | X is S, $R^1$ is Pr, $R^2$ is Me, and Pyr is 3-pyridinyl(5-Cl). |
| 211 | X is S, $R^1$ is Pr, $R^2$ is H, and Pyr is 2-pyridinyl. |
| 212 | X is S, $R^1$ is Pr, $R^2$ is H, and Pyr is 3-pyridinyl. |
| 213 | X is S, $R^1$ is Pr, $R^2$ is H, and Pyr is 4-pyridinyl. |
| 214 | X is S, $R^1$ is Pr, $R^2$ is H, and Pyr is 2-pyridinyl(3-$CH_3$). |
| 215 | X is S, $R^1$ is Pr, $R^2$ is H, and Pyr is 2-pyridinyl(4-$CH_3$). |
| 216 | X is S, $R^1$ is Pr, $R^2$ is H, and Pyr is 3-pyridinyl(2-$CH_3$). |
| 217 | X is S, $R^1$ is Pr, $R^2$ is H, and Pyr is 3-pyridinyl(4-$CH_3$). |
| 218 | X is S, $R^1$ is Pr, $R^2$ is H, and Pyr is 2-pyridinyl(3-Cl). |
| 219 | X is S, $R^1$ is Pr, $R^2$ is H, and Pyr is 2-pyridinyl(4-Cl). |
| 220 | X is S, $R^1$ is Pr, $R^2$ is H, and Pyr is 3-pyridinyl(5-Cl). |
| 221 | X is S, $R^1$ is Pr, $R^2$ is Et, and Pyr is 2-pyridinyl. |
| 222 | X is S, $R^1$ is Pr, $R^2$ is Et, and Pyr is 3-pyridinyl. |
| 223 | X is S, $R^1$ is Pr, $R^2$ is Et, and Pyr is 4-pyridinyl. |
| 224 | X is S, $R^1$ is Pr, $R^2$ is Et, and Pyr is 2-pyridinyl(3-$CH_3$). |
| 225 | X is S, $R^1$ is Pr, $R^2$ is Et, and Pyr is 2-pyridinyl(4-$CH_3$). |
| 226 | X is S, $R^1$ is Pr, $R^2$ is Et, and Pyr is 3-pyridinyl(2-$CH_3$). |
| 227 | X is S, $R^1$ is Pr, $R^2$ is Et, and Pyr is 3-pyridinyl(4-$CH_3$). |
| 228 | X is S, $R^1$ is Pr, $R^2$ is Et, and Pyr is 2-pyridinyl(3-Cl). |
| 229 | X is S, $R^1$ is Pr, $R^2$ is Et, and Pyr is 2-pyridinyl(4-Cl). |
| 230 | X is S, $R^1$ is Pr, $R^2$ is Et, and Pyr is 3-pyridinyl(5-Cl). |
| 231 | X is S, $R^1$ is Pr, $R^2$ is Pr, and Pyr is 2-pyridinyl. |
| 232 | X is S, $R^1$ is Pr, $R^2$ is Pr, and Pyr is 3-pyridinyl. |
| 233 | X is S, $R^1$ is Pr, $R^2$ is Pr, and Pyr is 4-pyridinyl. |
| 234 | X is S, $R^1$ is Pr, $R^2$ is Pr, and Pyr is 2-pyridinyl(3-$CH_3$). |
| 235 | X is S, $R^1$ is Pr, $R^2$ is Pr, and Pyr is 2-pyridinyl(4-$CH_3$). |
| 236 | X is S, $R^1$ is Pr, $R^2$ is Pr, and Pyr is 3-pyridinyl(2-$CH_3$). |
| 237 | X is S, $R^1$ is Pr, $R^2$ is Pr, and Pyr is 3-pyridinyl(4-$CH_3$). |
| 238 | X is S, $R^1$ is Pr, $R^2$ is Pr, and Pyr is 2-pyridinyl(3-Cl). |
| 239 | X is S, $R^1$ is Pr, $R^2$ is Pr, and Pyr is 2-pyridinyl(4-Cl). |
| 240 | X is S, $R^1$ is Pr, $R^2$ is Pr, and Pyr is 3-pyridinyl(5-Cl). |
| 241 | X is S, $R^1$ is Pr, $R^2$ is $CF_3$, and Pyr is 2-pyridinyl. |
| 242 | X is S, $R^1$ is Pr, $R^2$ is $CF_3$, and Pyr is 3-pyridinyl. |
| 243 | X is S, $R^1$ is Pr, $R^2$ is $CF_3$, and Pyr is 4-pyridinyl. |
| 244 | X is S, $R^1$ is Pr, $R^2$ is $CF_3$, and Pyr is 2-pyridinyl(3-$CH_3$). |
| 245 | X is S, $R^1$ is Pr, $R^2$ is $CF_3$, and Pyr is 2-pyridinyl(4-$CH_3$). |
| 246 | X is S, $R^1$ is Pr, $R^2$ is $CF_3$, and Pyr is 3-pyridinyl(2-$CH_3$). |
| 247 | X is S, $R^1$ is Pr, $R^2$ is $CF_3$, and Pyr is 3-pyridinyl(4-$CH_3$). |
| 248 | X is S, $R^1$ is Pr, $R^2$ is $CF_3$, and Pyr is 2-pyridinyl(3-Cl). |
| 249 | X is S, $R^1$ is Pr, $R^2$ is $CF_3$, and Pyr is 2-pyridinyl(4-Cl). |
| 250 | X is S, $R^1$ is Pr, $R^2$ is $CF_3$, and Pyr is 3-pyridinyl(5-Cl). |
| 251 | X is S, $R^1$ is Pr, $R^2$ is Cl, and Pyr is 2-pyridinyl. |
| 252 | X is S, $R^1$ is Pr, $R^2$ is Cl, and Pyr is 3-pyridinyl. |
| 253 | X is S, $R^1$ is Pr, $R^2$ is Cl, and Pyr is 4-pyridinyl. |
| 254 | X is S, $R^1$ is Pr, $R^2$ is Cl, and Pyr is 2-pyridinyl(3-$CH_3$). |
| 255 | X is S, $R^1$ is Pr, $R^2$ is Cl, and Pyr is 2-pyridinyl(4-$CH_3$). |
| 256 | X is S, $R^1$ is Pr, $R^2$ is Cl, and Pyr is 3-pyridinyl(2-$CH_3$). |
| 257 | X is S, $R^1$ is Pr, $R^2$ is Cl, and Pyr is 3-pyridinyl(4-$CH_3$). |
| 258 | X is S, $R^1$ is Pr, $R^2$ is Cl, and Pyr is 2-pyridinyl(3-Cl). |
| 259 | X is S, $R^1$ is Pr, $R^2$ is Cl, and Pyr is 2-pyridinyl(4-Cl). |
| 260 | X is S, $R^1$ is Pr, $R^2$ is Cl, and Pyr is 3-pyridinyl(5-Cl). |
| 261 | X is S, $R^1$ is Pr, $R^2$ is Br, and Pyr is 2-pyridinyl. |
| 262 | X is S, $R^1$ is Pr, $R^2$ is Br, and Pyr is 3-pyridinyl. |

| Table | Row Heading |
| --- | --- |
| 263 | X is S, $R^1$ is Pr, $R^2$ is Br, and Pyr is 4-pyridinyl. |
| 264 | X is S, $R^1$ is Pr, $R^2$ is Br, and Pyr is 2-pyridinyl(3-$CH_3$). |
| 265 | X is S, $R^1$ is Pr, $R^2$ is Br, and Pyr is 2-pyridinyl(4-$CH_3$). |
| 266 | X is S, $R^1$ is Pr, $R^2$ is Br, and Pyr is 3-pyridinyl(2-$CH_3$). |
| 267 | X is S, $R^1$ is Pr, $R^2$ is Br, and Pyr is 3-pyridinyl(4-$CH_3$). |
| 268 | X is S, $R^1$ is Pr, $R^2$ is Br, and Pyr is 2-pyridinyl(3-Cl). |
| 269 | X is S, $R^1$ is Pr, $R^2$ is Br, and Pyr is 2-pyridinyl(4-Cl). |
| 270 | X is S, $R^1$ is Pr, $R^2$ is Br, and Pyr is 3-pyridinyl(5-Cl). |
| 271 | X is S, $R^1$ is Pr, $R^2$ is I, and Pyr is 2-pyridinyl. |
| 272 | X is S, $R^1$ is Pr, $R^2$ is I, and Pyr is 3-pyridinyl. |
| 273 | X is S, $R^1$ is Pr, $R^2$ is I, and Pyr is 4-pyridinyl. |
| 274 | X is S, $R^1$ is Pr, $R^2$ is I, and Pyr is 2-pyridinyl(3-$CH_3$). |
| 275 | X is S, $R^1$ is Pr, $R^2$ is I, and Pyr is 2-pyridinyl(4-$CH_3$). |
| 276 | X is S, $R^1$ is Pr, $R^2$ is I, and Pyr is 3-pyridinyl(2-$CH_3$). |
| 277 | X is S, $R^1$ is Pr, $R^2$ is I, and Pyr is 3-pyridinyl(4-$CH_3$). |
| 278 | X is S, $R^1$ is Pr, $R^2$ is I, and Pyr is 2-pyridinyl(3-Cl). |
| 279 | X is S, $R^1$ is Pr, $R^2$ is I, and Pyr is 2-pyridinyl(4-Cl). |
| 280 | X is S, $R^1$ is Pr, $R^2$ is I, and Pyr is 3-pyridinyl(5-Cl). |
| 281 | X is S, $R^1$ is Pr, $R^2$ is OMe, and Pyr is 2-pyridinyl. |
| 282 | X is S, $R^1$ is Pr, $R^2$ is OMe, and Pyr is 3-pyridinyl. |
| 283 | X is S, $R^1$ is Pr, $R^2$ is OMe, and Pyr is 4-pyridinyl. |
| 284 | X is S, $R^1$ is Pr, $R^2$ is OMe, and Pyr is 2-pyridinyl(3-$CH_3$). |
| 285 | X is S, $R^1$ is Pr, $R^2$ is OMe, and Pyr is 2-pyridinyl(4-$CH_3$). |
| 286 | X is S, $R^1$ is Pr, $R^2$ is OMe, and Pyr is 3-pyridinyl(2-$CH_3$). |
| 287 | X is S, $R^1$ is Pr, $R^2$ is OMe, and Pyr is 3-pyridinyl(4-$CH_3$). |
| 288 | X is S, $R^1$ is Pr, $R^2$ is OMe, and Pyr is 2-pyridinyl(3-Cl). |
| 289 | X is S, $R^1$ is Pr, $R^2$ is OMe, and Pyr is 2-pyridinyl(4-Cl). |
| 290 | X is S, $R^1$ is Pr, $R^2$ is OMe, and Pyr is 3-pyridinyl(5-Cl). |
| 291 | X is S, $R^1$ is Pr, $R^2$ is OEt, and Pyr is 2-pyridinyl. |
| 292 | X is S, $R^1$ is Pr, $R^2$ is OEt, and Pyr is 3-pyridinyl. |
| 293 | X is S, $R^1$ is Pr, $R^2$ is OEt, and Pyr is 4-pyridinyl. |
| 294 | X is S, $R^1$ is Pr, $R^2$ is OEt, and Pyr is 2-pyridinyl(3-$CH_3$). |
| 295 | X is S, $R^1$ is Pr, $R^2$ is OEt, and Pyr is 2-pyridinyl(4-$CH_3$). |
| 296 | X is S, $R^1$ is Pr, $R^2$ is OEt, and Pyr is 3-pyridinyl(2-$CH_3$). |
| 297 | X is S, $R^1$ is Pr, $R^2$ is OEt, and Pyr is 3-pyridinyl(4-$CH_3$). |
| 298 | X is S, $R^1$ is Pr, $R^2$ is OEt, and Pyr is 2-pyridinyl(3-Cl). |
| 299 | X is S, $R^1$ is Pr, $R^2$ is OEt, and Pyr is 2-pyridinyl(4-Cl). |
| 300 | X is S, $R^1$ is Pr, $R^2$ is OEt, and Pyr is 3-pyridinyl(5-Cl). |
| 301 | X is —CH=CH—, $R^1$ is Me, $R^2$ is Me, and Pyr is 2-pyridinyl. |
| 302 | X is —CH=CH—, $R^1$ is Me, $R^2$ is Me, and Pyr is 3-pyridinyl. |
| 303 | X is —CH=CH—, $R^1$ is Me, $R^2$ is Me, and Pyr is 4-pyridinyl. |
| 304 | X is —CH=CH—, $R^1$ is Me, $R^2$ is Me, and Pyr is 2-pyridinyl(3-$CH_3$). |
| 305 | X is —CH=CH—, $R^1$ is Me, $R^2$ is Me, and Pyr is 2-pyridinyl(4-$CH_3$). |
| 306 | X is —CH=CH—, $R^1$ is Me, $R^2$ is Me, and Pyr is 3-pyridinyl(2-$CH_3$). |
| 307 | X is —CH=CH—, $R^1$ is Me, $R^2$ is Me, and Pyr is 3-pyridinyl(4-$CH_3$). |
| 308 | X is —CH=CH—, $R^1$ is Me, $R^2$ is Me, and Pyr is 2-pyridinyl(3-Cl). |
| 309 | X is —CH=CH—, $R^1$ is Me, $R^2$ is Me, and Pyr is 2-pyridinyl(4-Cl). |
| 310 | X is —CH=CH—, $R^1$ is Me, $R^2$ is Me, and Pyr is 3-pyridinyl(5-Cl). |
| 311 | X is —CH=CH—, $R^1$ is Me, $R^2$ is H, and Pyr is 2-pyridinyl. |
| 312 | X is —CH=CH—, $R^1$ is Me, $R^2$ is H, and Pyr is 3-pyridinyl. |
| 313 | X is —CH=CH—, $R^1$ is Me, $R^2$ is H, and Pyr is 4-pyridinyl. |
| 314 | X is —CH=CH—, $R^1$ is Me, $R^2$ is H, and Pyr is 2-pyridinyl(3-$CH_3$). |
| 315 | X is —CH=CH—, $R^1$ is Me, $R^2$ is H, and Pyr is 2-pyridinyl(4-$CH_3$). |
| 316 | X is —CH=CH—, $R^1$ is Me, $R^2$ is H, and Pyr is 3-pyridinyl(2-$CH_3$). |
| 317 | X is —CH=CH—, $R^1$ is Me, $R^2$ is H, and Pyr is 3-pyridinyl(4-$CH_3$). |
| 318 | X is —CH=CH—, $R^1$ is Me, $R^2$ is H, and Pyr is 2-pyridinyl(3-Cl). |
| 319 | X is —CH=CH—, $R^1$ is Me, $R^2$ is H, and Pyr is 2-pyridinyl(4-Cl). |
| 320 | X is —CH=CH—, $R^1$ is Me, $R^2$ is H, and Pyr is 3-pyridinyl(5-Cl). |
| 321 | X is —CH=CH—, $R^1$ is Me, $R^2$ is Et, and Pyr is 2-pyridinyl. |
| 322 | X is —CH=CH—, $R^1$ is Me, $R^2$ is Et, and Pyr is 3-pyridinyl. |
| 323 | X is —CH=CH—, $R^1$ is Me, $R^2$ is Et, and Pyr is 4-pyridinyl. |
| 324 | X is —CH=CH—, $R^1$ is Me, $R^2$ is Et, and Pyr is 2-pyridinyl(3-$CH_3$). |
| 325 | X is —CH=CH—, $R^1$ is Me, $R^2$ is Et, and Pyr is 2-pyridinyl(4-$CH_3$). |
| 326 | X is —CH=CH—, $R^1$ is Me, $R^2$ is Et, and Pyr is 3-pyridinyl(2-$CH_3$). |
| 327 | X is —CH=CH—, $R^1$ is Me, $R^2$ is Et, and Pyr is 3-pyridinyl(4-$CH_3$). |
| 328 | X is —CH=CH—, $R^1$ is Me, $R^2$ is Et, and Pyr is 2-pyridinyl(3-Cl). |
| 329 | X is —CH=CH—, $R^1$ is Me, $R^2$ is Et, and Pyr is 2-pyridinyl(4-Cl). |
| 330 | X is —CH=CH—, $R^1$ is Me, $R^2$ is Et, and Pyr is 3-pyridinyl(5-Cl). |
| 331 | X is —CH=CH—, $R^1$ is Me, $R^2$ is Pr, and Pyr is 2-pyridinyl. |
| 332 | X is —CH=CH—, $R^1$ is Me, $R^2$ is Pr, and Pyr is 3-pyridinyl. |
| 333 | X is —CH=CH—, $R^1$ is Me, $R^2$ is Pr, and Pyr is 4-pyridinyl. |
| 334 | X is —CH=CH—, $R^1$ is Me, $R^2$ is Pr, and Pyr is 2-pyridinyl(3-$CH_3$). |
| 335 | X is —CH=CH—, $R^1$ is Me, $R^2$ is Pr, and Pyr is 2-pyridinyl(4-$CH_3$). |
| 336 | X is —CH=CH—, $R^1$ is Me, $R^2$ is Pr, and Pyr is 3-pyridinyl(2-$CH_3$). |
| 337 | X is —CH=CH—, $R^1$ is Me, $R^2$ is Pr, and Pyr is 3-pyridinyl(4-$CH_3$). |
| 338 | X is —CH=CH—, $R^1$ is Me, $R^2$ is Pr, and Pyr is 2-pyridinyl(3-Cl). |
| 339 | X is —CH=CH—, $R^1$ is Me, $R^2$ is Pr, and Pyr is 2-pyridinyl(4-Cl). |

-continued

| Table | Row Heading |
|---|---|
| 340 | X is —CH═CH—, $R^1$ is Me, $R^2$ is Pr, and Pyr is 3-pyridinyl(5-Cl). |
| 341 | X is —CH═CH—, $R^1$ is Me, $R^2$ is $CF_3$, and Pyr is 2-pyridinyl. |
| 342 | X is —CH═CH—, $R^1$ is Me, $R^2$ is $CF_3$, and Pyr is 3-pyridinyl. |
| 343 | X is —CH═CH—, $R^1$ is Me, $R^2$ is $CF_3$, and Pyr is 4-pyridinyl. |
| 344 | X is —CH═CH—, $R^1$ is Me, $R^2$ is $CF_3$, and Pyr is 2-pyridinyl(3-$CH_3$). |
| 345 | X is —CH═CH—, $R^1$ is Me, $R^2$ is $CF_3$, and Pyr is 2-pyridinyl(4-$CH_3$). |
| 346 | X is —CH═CH—, $R^1$ is Me, $R^2$ is $CF_3$, and Pyr is 3-pyridinyl(2-$CH_3$). |
| 347 | X is —CH═CH—, $R^1$ is Me, $R^2$ is $CF_3$, and Pyr is 3-pyridinyl(4-$CH_3$). |
| 348 | X is —CH═CH—, $R^1$ is Me, $R^2$ is $CF_3$, and Pyr is 2-pyridinyl(3-Cl). |
| 349 | X is —CH═CH—, $R^1$ is Me, $R^2$ is $CF_3$, and Pyr is 2-pyridinyl(4-Cl). |
| 350 | X is —CH═CH—, $R^1$ is Me, $R^2$ is $CF_3$, and Pyr is 3-pyridinyl(5-Cl). |
| 351 | X is —CH═CH—, $R^1$ is Me, $R^2$ is Cl, and Pyr is 2-pyridinyl. |
| 352 | X is —CH═CH—, $R^1$ is Me, $R^2$ is Cl, and Pyr is 3-pyridinyl. |
| 353 | X is —CH═CH—, $R^1$ is Me, $R^2$ is Cl, and Pyr is 4-pyridinyl. |
| 354 | X is —CH═CH—, $R^1$ is Me, $R^2$ is Cl, and Pyr is 2-pyridinyl(3-$CH_3$). |
| 355 | X is —CH═CH—, $R^1$ is Me, $R^2$ is Cl, and Pyr is 2-pyridinyl(4-$CH_3$). |
| 356 | X is —CH═CH—, $R^1$ is Me, $R^2$ is Cl, and Pyr is 3-pyridinyl(2-$CH_3$). |
| 357 | X is —CH═CH—, $R^1$ is Me, $R^2$ is Cl, and Pyr is 3-pyridinyl(4-$CH_3$). |
| 358 | X is —CH═CH—, $R^1$ is Me, $R^2$ is Cl, and Pyr is 2-pyridinyl(3-Cl). |
| 359 | X is —CH═CH—, $R^1$ is Me, $R^2$ is Cl, and Pyr is 2-pyridinyl(4-Cl). |
| 360 | X is —CH═CH—, $R^1$ is Me, $R^2$ is Cl, and Pyr is 3-pyridinyl(5-Cl). |
| 361 | X is —CH═CH—, $R^1$ is Me, $R^2$ is Br, and Pyr is 2-pyridinyl. |
| 362 | X is —CH═CH—, $R^1$ is Me, $R^2$ is Br, and Pyr is 3-pyridinyl. |
| 363 | X is —CH═CH—, $R^1$ is Me, $R^2$ is Br, and Pyr is 4-pyridinyl. |
| 364 | X is —CH═CH—, $R^1$ is Me, $R^2$ is Br, and Pyr is 2-pyridinyl(3-$CH_3$). |
| 365 | X is —CH═CH—, $R^1$ is Me, $R^2$ is Br, and Pyr is 2-pyridinyl(4-$CH_3$). |
| 366 | X is —CH═CH—, $R^1$ is Me, $R^2$ is Br, and Pyr is 3-pyridinyl(2-$CH_3$). |
| 367 | X is —CH═CH—, $R^1$ is Me, $R^2$ is Br, and Pyr is 3-pyridinyl(4-$CH_3$). |
| 368 | X is —CH═CH—, $R^1$ is Me, $R^2$ is Br, and Pyr is 2-pyridinyl(3-Cl). |
| 369 | X is —CH═CH—, $R^1$ is Me, $R^2$ is Br, and Pyr is 2-pyridinyl(4-Cl). |
| 370 | X is —CH═CH—, $R^1$ is Me, $R^2$ is Br, and Pyr is 3-pyridinyl(5-Cl). |
| 371 | X is —CH═CH—, $R^1$ is Me, $R^2$ is I, and Pyr is 2-pyridinyl. |
| 372 | X is —CH═CH—, $R^1$ is Me, $R^2$ is I, and Pyr is 3-pyridinyl. |
| 373 | X is —CH═CH—, $R^1$ is Me, $R^2$ is I, and Pyr is 4-pyridinyl. |
| 374 | X is —CH═CH—, $R^1$ is Me, $R^2$ is I, and Pyr is 2-pyridinyl(3-$CH_3$). |
| 375 | X is —CH═CH—, $R^1$ is Me, $R^2$ is I, and Pyr is 2-pyridinyl(4-$CH_3$). |
| 376 | X is —CH═CH—, $R^1$ is Me, $R^2$ is I, and Pyr is 3-pyridinyl(2-$CH_3$). |
| 377 | X is —CH═CH—, $R^1$ is Me, $R^2$ is I, and Pyr is 3-pyridinyl(4-$CH_3$). |
| 378 | X is —CH═CH—, $R^1$ is Me, $R^2$ is I, and Pyr is 2-pyridinyl(3-Cl). |
| 379 | X is —CH═CH—, $R^1$ is Me, $R^2$ is I, and Pyr is 2-pyridinyl(4-Cl). |
| 380 | X is —CH═CH—, $R^1$ is Me, $R^2$ is I, and Pyr is 3-pyridinyl(5-Cl). |
| 381 | X is —CH═CH—, $R^1$ is Me, $R^2$ is OMe, and Pyr is 2-pyridinyl. |
| 382 | X is —CH═CH—, $R^1$ is Me, $R^2$ is OMe, and Pyr is 3-pyridinyl. |
| 383 | X is —CH═CH—, $R^1$ is Me, $R^2$ is OMe, and Pyr is 4-pyridinyl. |
| 384 | X is —CH═CH—, $R^1$ is Me, $R^2$ is OMe, and Pyr is 2-pyridinyl(3-$CH_3$). |
| 385 | X is —CH═CH—, $R^1$ is Me, $R^2$ is OMe, and Pyr is 2-pyridinyl(4-$CH_3$). |
| 386 | X is —CH═CH—, $R^1$ is Me, $R^2$ is OMe, and Pyr is 3-pyridinyl(2-$CH_3$). |
| 387 | X is —CH═CH—, $R^1$ is Me, $R^2$ is OMe, and Pyr is 3-pyridinyl(4-$CH_3$). |
| 388 | X is —CH═CH—, $R^1$ is Me, $R^2$ is OMe, and Pyr is 2-pyridinyl(3-Cl). |
| 389 | X is —CH═CH—, $R^1$ is Me, $R^2$ is OMe, and Pyr is 2-pyridinyl(4-Cl). |
| 390 | X is —CH═CH—, $R^1$ is Me, $R^2$ is OMe, and Pyr is 3-pyridinyl(5-Cl). |
| 391 | X is —CH═CH—, $R^1$ is Me, $R^2$ is OEt, and Pyr is 2-pyridinyl. |
| 392 | X is —CH═CH—, $R^1$ is Me, $R^2$ is OEt, and Pyr is 3-pyridinyl. |
| 393 | X is —CH═CH—, $R^1$ is Me, $R^2$ is OEt, and Pyr is 4-pyridinyl. |
| 394 | X is —CH═CH—, $R^1$ is Me, $R^2$ is OEt, and Pyr is 2-pyridinyl(3-$CH_3$). |
| 395 | X is —CH═CH—, $R^1$ is Me, $R^2$ is OEt, and Pyr is 2-pyridinyl(4-$CH_3$). |
| 396 | X is —CH═CH—, $R^1$ is Me, $R^2$ is OEt, and Pyr is 3-pyridinyl(2-$CH_3$). |
| 397 | X is —CH═CH—, $R^1$ is Me, $R^2$ is OEt, and Pyr is 3-pyridinyl(4-$CH_3$). |
| 398 | X is —CH═CH—, $R^1$ is Me, $R^2$ is OEt, and Pyr is 2-pyridinyl(3-Cl). |
| 399 | X is —CH═CH—, $R^1$ is Me, $R^2$ is OEt, and Pyr is 2-pyridinyl(4-Cl). |
| 400 | X is —CH═CH—, $R^1$ is Me, $R^2$ is OEt, and Pyr is 3-pyridinyl(5-Cl). |
| 401 | X is —CH═CH—, $R^1$ is Et, $R^2$ is Me, and Pyr is 2-pyridinyl. |
| 402 | X is —CH═CH—, $R^1$ is Et, $R^2$ is Me, and Pyr is 3-pyridinyl. |
| 403 | X is —CH═CH—, $R^1$ is Et, $R^2$ is Me, and Pyr is 4-pyridinyl. |
| 404 | X is —CH═CH—, $R^1$ is Et, $R^2$ is Me, and Pyr is 2-pyridinyl(3-$CH_3$). |
| 405 | X is —CH═CH—, $R^1$ is Et, $R^2$ is Me, and Pyr is 2-pyridinyl(4-$CH_3$). |
| 406 | X is —CH═CH—, $R^1$ is Et, $R^2$ is Me, and Pyr is 3-pyridinyl(2-$CH_3$). |
| 407 | X is —CH═CH—, $R^1$ is Et, $R^2$ is Me, and Pyr is 3-pyridinyl(4-$CH_3$). |
| 408 | X is —CH═CH—, $R^1$ is Et, $R^2$ is Me, and Pyr is 2-pyridinyl(3-Cl). |
| 409 | X is —CH═CH—, $R^1$ is Et, $R^2$ is Me, and Pyr is 2-pyridinyl(4-Cl). |
| 410 | X is —CH═CH—, $R^1$ is Et, $R^2$ is Me, and Pyr is 3-pyridinyl(5-Cl). |
| 411 | X is —CH═CH—, $R^1$ is Et, $R^2$ is H, and Pyr is 2-pyridinyl. |
| 412 | X is —CH═CH—, $R^1$ is Et, $R^2$ is H, and Pyr is 3-pyridinyl. |
| 413 | X is —CH═CH—, $R^1$ is Et, $R^2$ is H, and Pyr is 4-pyridinyl. |
| 414 | X is —CH═CH—, $R^1$ is Et, $R^2$ is H, and Pyr is 2-pyridinyl(3-$CH_3$). |
| 415 | X is —CH═CH—, $R^1$ is Et, $R^2$ is H, and Pyr is 2-pyridinyl(4-$CH_3$). |
| 416 | X is —CH═CH—, $R^1$ is Et, $R^2$ is H, and Pyr is 3-pyridinyl(2-$CH_3$). |

| Table | Row Heading |
|---|---|
| 417 | X is —CH═CH—, $R^1$ is Et, $R^2$ is H, and Pyr is 3-pyridinyl(4-$CH_3$). |
| 418 | X is —CH═CH—, $R^1$ is Et, $R^2$ is H, and Pyr is 2-pyridinyl(3-Cl). |
| 419 | X is —CH═CH—, $R^1$ is Et, $R^2$ is H, and Pyr is 2-pyridinyl(4-Cl). |
| 420 | X is —CH═CH—, $R^1$ is Et, $R^2$ is H, and Pyr is 3-pyridinyl(5-Cl). |
| 421 | X is —CH═CH—, $R^1$ is Et, $R^2$ is Et, and Pyr is 2-pyridinyl. |
| 422 | X is —CH═CH—, $R^1$ is Et, $R^2$ is Et, and Pyr is 3-pyridinyl. |
| 423 | X is —CH═CH—, $R^1$ is Et, $R^2$ is Et, and Pyr is 4-pyridinyl. |
| 424 | X is —CH═CH—, $R^1$ is Et, $R^2$ is Et, and Pyr is 2-pyridinyl(3-$CH_3$). |
| 425 | X is —CH═CH—, $R^1$ is Et, $R^2$ is Et, and Pyr is 2-pyridinyl(4-$CH_3$). |
| 426 | X is —CH═CH—, $R^1$ is Et, $R^2$ is Et, and Pyr is 3-pyridinyl(2-$CH_3$). |
| 427 | X is —CH═CH—, $R^1$ is Et, $R^2$ is Et, and Pyr is 3-pyridinyl(4-$CH_3$). |
| 428 | X is —CH═CH—, $R^1$ is Et, $R^2$ is Et, and Pyr is 2-pyridinyl(3-Cl). |
| 429 | X is —CH═CH—, $R^1$ is Et, $R^2$ is Et, and Pyr is 2-pyridinyl(4-Cl). |
| 430 | X is —CH═CH—, $R^1$ is Et, $R^2$ is Et, and Pyr is 3-pyridinyl(5-Cl). |
| 431 | X is —CH═CH—, $R^1$ is Et, $R^2$ is Pr, and Pyr is 2-pyridinyl. |
| 432 | X is —CH═CH—, $R^1$ is Et, $R^2$ is Pr, and Pyr is 3-pyridinyl. |
| 433 | X is —CH═CH—, $R^1$ is Et, $R^2$ is Pr, and Pyr is 4-pyridinyl. |
| 434 | X is —CH═CH—, $R^1$ is Et, $R^2$ is Pr, and Pyr is 2-pyridinyl(3-$CH_3$). |
| 435 | X is —CH═CH—, $R^1$ is Et, $R^2$ is Pr, and Pyr is 2-pyridinyl(4-$CH_3$). |
| 436 | X is —CH═CH—, $R^1$ is Et, $R^2$ is Pr, and Pyr is 3-pyridinyl(2-$CH_3$). |
| 437 | X is —CH═CH—, $R^1$ is Et, $R^2$ is Pr, and Pyr is 3-pyridinyl(4-$CH_3$). |
| 438 | X is —CH═CH—, $R^1$ is Et, $R^2$ is Pr, and Pyr is 2-pyridinyl(3-Cl). |
| 439 | X is —CH═CH—, $R^1$ is Et, $R^2$ is Pr, and Pyr is 2-pyridinyl(4-Cl). |
| 440 | X is —CH═CH—, $R^1$ is Et, $R^2$ is Pr, and Pyr is 3-pyridinyl(5-Cl). |
| 441 | X is —CH═CH—, $R^1$ is Et, $R^2$ is $CF_3$, and Pyr is 2-pyridinyl. |
| 442 | X is —CH═CH—, $R^1$ is Et, $R^2$ is $CF_3$, and Pyr is 3-pyridinyl. |
| 443 | X is —CH═CH—, $R^1$ is Et, $R^2$ is $CF_3$, and Pyr is 4-pyridinyl. |
| 444 | X is —CH═CH—, $R^1$ is Et, $R^2$ is $CF_3$, and Pyr is 2-pyridinyl(3-$CH_3$). |
| 445 | X is —CH═CH—, $R^1$ is Et, $R^2$ is $CF_3$, and Pyr is 2-pyridinyl(4-$CH_3$). |
| 446 | X is —CH═CH—, $R^1$ is Et, $R^2$ is $CF_3$, and Pyr is 3-pyridinyl(2-$CH_3$). |
| 447 | X is —CH═CH—, $R^1$ is Et, $R^2$ is $CF_3$, and Pyr is 3-pyridinyl(4-$CH_3$). |
| 448 | X is —CH═CH—, $R^1$ is Et, $R^2$ is $CF_3$, and Pyr is 2-pyridinyl(3-Cl). |
| 449 | X is —CH═CH—, $R^1$ is Et, $R^2$ is $CF_3$, and Pyr is 2-pyridinyl(4-Cl). |
| 450 | X is —CH═CH—, $R^1$ is Et, $R^2$ is $CF_3$, and Pyr is 3-pyridinyl(5-Cl). |
| 451 | X is —CH═CH—, $R^1$ is Et, $R^2$ is Cl, and Pyr is 2-pyridinyl. |
| 452 | X is —CH═CH—, $R^1$ is Et, $R^2$ is Cl, and Pyr is 3-pyridinyl. |
| 453 | X is —CH═CH—, $R^1$ is Et, $R^2$ is Cl, and Pyr is 4-pyridinyl. |
| 454 | X is —CH═CH—, $R^1$ is Et, $R^2$ is Cl, and Pyr is 2-pyridinyl(3-$CH_3$). |
| 455 | X is —CH═CH—, $R^1$ is Et, $R^2$ is Cl, and Pyr is 2-pyridinyl(4-$CH_3$). |
| 456 | X is —CH═CH—, $R^1$ is Et, $R^2$ is Cl, and Pyr is 3-pyridinyl(2-$CH_3$). |
| 457 | X is —CH═CH—, $R^1$ is Et, $R^2$ is Cl, and Pyr is 3-pyridinyl(4-$CH_3$). |
| 458 | X is —CH═CH—, $R^1$ is Et, $R^2$ is Cl, and Pyr is 2-pyridinyl(3-Cl). |
| 459 | X is —CH═CH—, $R^1$ is Et, $R^2$ is Cl, and Pyr is 2-pyridinyl(4-Cl). |
| 460 | X is —CH═CH—, $R^1$ is Et, $R^2$ is Cl, and Pyr is 3-pyridinyl(5-Cl). |
| 461 | X is —CH═CH—, $R^1$ is Et, $R^2$ is Br, and Pyr is 2-pyridinyl. |
| 462 | X is —CH═CH—, $R^1$ is Et, $R^2$ is Br, and Pyr is 3-pyridinyl. |
| 463 | X is —CH═CH—, $R^1$ is Et, $R^2$ is Br, and Pyr is 4-pyridinyl. |
| 464 | X is —CH═CH—, $R^1$ is Et, $R^2$ is Br, and Pyr is 2-pyridinyl(3-$CH_3$). |
| 465 | X is —CH═CH—, $R^1$ is Et, $R^2$ is Br, and Pyr is 2-pyridinyl(4-$CH_3$). |
| 466 | X is —CH═CH—, $R^1$ is Et, $R^2$ is Br, and Pyr is 3-pyridinyl(2-$CH_3$). |
| 467 | X is —CH═CH—, $R^1$ is Et, $R^2$ is Br, and Pyr is 3-pyridinyl(4-$CH_3$). |
| 468 | X is —CH═CH—, $R^1$ is Et, $R^2$ is Br, and Pyr is 2-pyridinyl(3-Cl). |
| 469 | X is —CH═CH—, $R^1$ is Et, $R^2$ is Br, and Pyr is 2-pyridinyl(4-Cl). |
| 470 | X is —CH═CH—, $R^1$ is Et, $R^2$ is Br, and Pyr is 3-pyridinyl(5-Cl). |
| 471 | X is —CH═CH—, $R^1$ is Et, $R^2$ is I, and Pyr is 2-pyridinyl. |
| 472 | X is —CH═CH—, $R^1$ is Et, $R^2$ is I, and Pyr is 3-pyridinyl. |
| 473 | X is —CH═CH—, $R^1$ is Et, $R^2$ is I, and Pyr is 4-pyridinyl. |
| 474 | X is —CH═CH—, $R^1$ is Et, $R^2$ is I, and Pyr is 2-pyridinyl(3-$CH_3$). |
| 475 | X is —CH═CH—, $R^1$ is Et, $R^2$ is I, and Pyr is 2-pyridinyl(4-$CH_3$). |
| 476 | X is —CH═CH—, $R^1$ is Et, $R^2$ is I, and Pyr is 3-pyridinyl(2-$CH_3$). |
| 477 | X is —CH═CH—, $R^1$ is Et, $R^2$ is I, and Pyr is 3-pyridinyl(4-$CH_3$). |
| 478 | X is —CH═CH—, $R^1$ is Et, $R^2$ is I, and Pyr is 2-pyridinyl(3-Cl). |
| 479 | X is —CH═CH—, $R^1$ is Et, $R^2$ is I, and Pyr is 2-pyridinyl(4-Cl). |
| 480 | X is —CH═CH—, $R^1$ is Et, $R^2$ is I, and Pyr is 3-pyridinyl(5-Cl). |
| 481 | X is —CH═CH—, $R^1$ is Et, $R^2$ is OMe, and Pyr is 2-pyridinyl. |
| 482 | X is —CH═CH—, $R^1$ is Et, $R^2$ is OMe, and Pyr is 3-pyridinyl. |
| 483 | X is —CH═CH—, $R^1$ is Et, $R^2$ is OMe, and Pyr is 4-pyridinyl. |
| 484 | X is —CH═CH—, $R^1$ is Et, $R^2$ is OMe, and Pyr is 2-pyridinyl(3-$CH_3$). |
| 485 | X is —CH═CH—, $R^1$ is Et, $R^2$ is OMe, and Pyr is 2-pyridinyl(4-$CH_3$). |
| 486 | X is —CH═CH—, $R^1$ is Et, $R^2$ is OMe, and Pyr is 3-pyridinyl(2-$CH_3$). |
| 487 | X is —CH═CH—, $R^1$ is Et, $R^2$ is OMe, and Pyr is 3-pyridinyl(4-$CH_3$). |
| 488 | X is —CH═CH—, $R^1$ is Et, $R^2$ is OMe, and Pyr is 2-pyridinyl(3-Cl). |
| 489 | X is —CH═CH—, $R^1$ is Et, $R^2$ is OMe, and Pyr is 2-pyridinyl(4-Cl). |
| 490 | X is —CH═CH—, $R^1$ is Et, $R^2$ is OMe, and Pyr is 3-pyridinyl(5-Cl). |
| 491 | X is —CH═CH—, $R^1$ is Et, $R^2$ is OEt, and Pyr is 2-pyridinyl. |
| 492 | X is —CH═CH—, $R^1$ is Et, $R^2$ is OEt, and Pyr is 3-pyridinyl. |
| 493 | X is —CH═CH—, $R^1$ is Et, $R^2$ is OEt, and Pyr is 4-pyridinyl. |

| Table | Row Heading |
| --- | --- |
| 494 | X is —CH=CH—, $R^1$ is Et, $R^2$ is OEt, and Pyr is 2-pyridinyl(3-$CH_3$). |
| 495 | X is —CH=CH—, $R^1$ is Et, $R^2$ is OEt, and Pyr is 2-pyridinyl(4-$CH_3$). |
| 496 | X is —CH=CH—, $R^1$ is Et, $R^2$ is OEt, and Pyr is 3-pyridinyl(2-$CH_3$). |
| 497 | X is —CH=CH—, $R^1$ is Et, $R^2$ is OEt, and Pyr is 3-pyridinyl(4-$CH_3$). |
| 498 | X is —CH=CH—, $R^1$ is Et, $R^2$ is OEt, and Pyr is 2-pyridinyl(3-Cl). |
| 499 | X is —CH=CH—, $R^1$ is Et, $R^2$ is OEt, and Pyr is 2-pyridinyl(4-Cl). |
| 500 | X is —CH=CH—, $R^1$ is Et, $R^2$ is OEt, and Pyr is 3-pyridinyl(5-Cl). |
| 501 | X is —CH=CH—, $R^1$ is Pr, $R^2$ is Me, and Pyr is 2-pyridinyl. |
| 502 | X is —CH=CH—, $R^1$ is Pr, $R^2$ is Me, and Pyr is 3-pyridinyl. |
| 503 | X is —CH=CH—, $R^1$ is Pr, $R^2$ is Me, and Pyr is 4-pyridinyl. |
| 504 | X is —CH=CH—, $R^1$ is Pr, $R^2$ is Me, and Pyr is 2-pyridinyl(3-$CH_3$). |
| 505 | X is —CH=CH—, $R^1$ is Pr, $R^2$ is Me, and Pyr is 2-pyridinyl(4-$CH_3$). |
| 506 | X is —CH=CH—, $R^1$ is Pr, $R^2$ is Me, and Pyr is 3-pyridinyl(2-$CH_3$). |
| 507 | X is —CH=CH—, $R^1$ is Pr, $R^2$ is Me, and Pyr is 3-pyridinyl(4-$CH_3$). |
| 508 | X is —CH=CH—, $R^1$ is Pr, $R^2$ is Me, and Pyr is 2-pyridinyl(3-Cl). |
| 509 | X is —CH=CH—, $R^1$ is Pr, $R^2$ is Me, and Pyr is 2-pyridinyl(4-Cl). |
| 510 | X is —CH=CH—, $R^1$ is Pr, $R^2$ is Me, and Pyr is 3-pyridinyl(5-Cl). |
| 511 | X is —CH=CH—, $R^1$ is Pr, $R^2$ is H, and Pyr is 2-pyridinyl. |
| 512 | X is —CH=CH—, $R^1$ is Pr, $R^2$ is H, and Pyr is 3-pyridinyl. |
| 513 | X is —CH=CH—, $R^1$ is Pr, $R^2$ is H, and Pyr is 4-pyridinyl. |
| 514 | X is —CH=CH—, $R^1$ is Pr, $R^2$ is H, and Pyr is 2-pyridinyl(3-$CH_3$). |
| 515 | X is —CH=CH—, $R^1$ is Pr, $R^2$ is H, and Pyr is 2-pyridinyl(4-$CH_3$). |
| 516 | X is —CH=CH—, $R^1$ is Pr, $R^2$ is H, and Pyr is 3-pyridinyl(2-$CH_3$). |
| 517 | X is —CH=CH—, $R^1$ is Pr, $R^2$ is H, and Pyr is 3-pyridinyl(4-$CH_3$). |
| 518 | X is —CH=CH—, $R^1$ is Pr, $R^2$ is H, and Pyr is 2-pyridinyl(3-Cl). |
| 519 | X is —CH=CH—, $R^1$ is Pr, $R^2$ is H, and Pyr is 2-pyridinyl(4-Cl). |
| 520 | X is —CH=CH—, $R^1$ is Pr, $R^2$ is H, and Pyr is 3-pyridinyl(5-Cl). |
| 521 | X is —CH=CH—, $R^1$ is Pr, $R^2$ is Et, and Pyr is 2-pyridinyl. |
| 522 | X is —CH=CH—, $R^1$ is Pr, $R^2$ is Et, and Pyr is 3-pyridinyl. |
| 523 | X is —CH=CH—, $R^1$ is Pr, $R^2$ is Et, and Pyr is 4-pyridinyl. |
| 524 | X is —CH=CH—, $R^1$ is Pr, $R^2$ is Et, and Pyr is 2-pyridinyl(3-$CH_3$). |
| 525 | X is —CH=CH—, $R^1$ is Pr, $R^2$ is Et, and Pyr is 2-pyridinyl(4-$CH_3$). |
| 526 | X is —CH=CH—, $R^1$ is Pr, $R^2$ is Et, and Pyr is 3-pyridinyl(2-$CH_3$). |
| 527 | X is —CH=CH—, $R^1$ is Pr, $R^2$ is Et, and Pyr is 3-pyridinyl(4-$CH_3$). |
| 528 | X is —CH=CH—, $R^1$ is Pr, $R^2$ is Et, and Pyr is 2-pyridinyl(3-Cl). |
| 529 | X is —CH=CH—, $R^1$ is Pr, $R^2$ is Et, and Pyr is 2-pyridinyl(4-Cl). |
| 530 | X is —CH=CH—, $R^1$ is Pr, $R^2$ is Et, and Pyr is 3-pyridinyl(5-Cl). |
| 531 | X is —CH=CH—, $R^1$ is Pr, $R^2$ is Pr, and Pyr is 2-pyridinyl. |
| 532 | X is —CH=CH—, $R^1$ is Pr, $R^2$ is Pr, and Pyr is 3-pyridinyl. |
| 533 | X is —CH=CH—, $R^1$ is Pr, $R^2$ is Pr, and Pyr is 4-pyridinyl. |
| 534 | X is —CH=CH—, $R^1$ is Pr, $R^2$ is Pr, and Pyr is 2-pyridinyl(3-$CH_3$). |
| 535 | X is —CH=CH—, $R^1$ is Pr, $R^2$ is Pr, and Pyr is 2-pyridinyl(4-$CH_3$). |
| 536 | X is —CH=CH—, $R^1$ is Pr, $R^2$ is Pr, and Pyr is 3-pyridinyl(2-$CH_3$). |
| 537 | X is —CH=CH—, $R^1$ is Pr, $R^2$ is Pr, and Pyr is 3-pyridinyl(4-$CH_3$). |
| 538 | X is —CH=CH—, $R^1$ is Pr, $R^2$ is Pr, and Pyr is 2-pyridinyl(3-Cl). |
| 539 | X is —CH=CH—, $R^1$ is Pr, $R^2$ is Pr, and Pyr is 2-pyridinyl(4-Cl). |
| 540 | X is —CH=CH—, $R^1$ is Pr, $R^2$ is Pr, and Pyr is 3-pyridinyl(5-Cl). |
| 541 | X is —CH=CH—, $R^1$ is Pr, $R^2$ is $CF_3$, and Pyr is 2-pyridinyl. |
| 542 | X is —CH=CH—, $R^1$ is Pr, $R^2$ is $CF_3$, and Pyr is 3-pyridinyl. |
| 543 | X is —CH=CH—, $R^1$ is Pr, $R^2$ is $CF_3$, and Pyr is 4-pyridinyl. |
| 544 | X is —CH=CH—, $R^1$ is Pr, $R^2$ is $CF_3$, and Pyr is 2-pyridinyl(3-$CH_3$). |
| 545 | X is —CH=CH—, $R^1$ is Pr, $R^2$ is $CF_3$, and Pyr is 2-pyridinyl(4-$CH_3$). |
| 546 | X is —CH=CH—, $R^1$ is Pr, $R^2$ is $CF_3$, and Pyr is 3-pyridinyl(2-$CH_3$). |
| 547 | X is —CH=CH—, $R^1$ is Pr, $R^2$ is $CF_3$, and Pyr is 3-pyridinyl(4-$CH_3$). |
| 548 | X is —CH=CH—, $R^1$ is Pr, $R^2$ is $CF_3$, and Pyr is 2-pyridinyl(3-Cl). |
| 549 | X is —CH=CH—, $R^1$ is Pr, $R^2$ is $CF_3$, and Pyr is 2-pyridinyl(4-Cl). |
| 550 | X is —CH=CH—, $R^1$ is Pr, $R^2$ is $CF_3$, and Pyr is 3-pyridinyl(5-Cl). |
| 551 | X is —CH=CH—, $R^1$ is Pr, $R^2$ is Cl, and Pyr is 2-pyridinyl. |
| 552 | X is —CH=CH—, $R^1$ is Pr, $R^2$ is Cl, and Pyr is 3-pyridinyl. |
| 553 | X is —CH=CH—, $R^1$ is Pr, $R^2$ is Cl, and Pyr is 4-pyridinyl. |
| 554 | X is —CH=CH—, $R^1$ is Pr, $R^2$ is Cl, and Pyr is 2-pyridinyl(3-$CH_3$). |
| 555 | X is —CH=CH—, $R^1$ is Pr, $R^2$ is Cl, and Pyr is 2-pyridinyl(4-$CH_3$). |
| 556 | X is —CH=CH—, $R^1$ is Pr, $R^2$ is Cl, and Pyr is 3-pyridinyl(2-$CH_3$). |
| 557 | X is —CH=CH—, $R^1$ is Pr, $R^2$ is Cl, and Pyr is 3-pyridinyl(4-$CH_3$). |
| 558 | X is —CH=CH—, $R^1$ is Pr, $R^2$ is Cl, and Pyr is 2-pyridinyl(3-Cl). |
| 559 | X is —CH=CH—, $R^1$ is Pr, $R^2$ is Cl, and Pyr is 2-pyridinyl(4-Cl). |
| 560 | X is —CH=CH—, $R^1$ is Pr, $R^2$ is Cl, and Pyr is 3-pyridinyl(5-Cl). |
| 561 | X is —CH=CH—, $R^1$ is Pr, $R^2$ is Br, and Pyr is 2-pyridinyl. |
| 562 | X is —CH=CH—, $R^1$ is Pr, $R^2$ is Br, and Pyr is 3-pyridinyl. |
| 563 | X is —CH=CH—, $R^1$ is Pr, $R^2$ is Br, and Pyr is 4-pyridinyl. |
| 564 | X is —CH=CH—, $R^1$ is Pr, $R^2$ is Br, and Pyr is 2-pyridinyl(3-$CH_3$). |
| 565 | X is —CH=CH—, $R^1$ is Pr, $R^2$ is Br, and Pyr is 2-pyridinyl(4-$CH_3$). |
| 566 | X is —CH=CH—, $R^1$ is Pr, $R^2$ is Br, and Pyr is 3-pyridinyl(2-$CH_3$). |
| 567 | X is —CH=CH—, $R^1$ is Pr, $R^2$ is Br, and Pyr is 3-pyridinyl(4-$CH_3$). |
| 568 | X is —CH=CH—, $R^1$ is Pr, $R^2$ is Br, and Pyr is 2-pyridinyl(3-Cl). |
| 569 | X is —CH=CH—, $R^1$ is Pr, $R^2$ is Br, and Pyr is 2-pyridinyl(4-Cl). |
| 570 | X is —CH=CH—, $R^1$ is Pr, $R^2$ is Br, and Pyr is 3-pyridinyl(5-Cl). |

-continued

| Table | Row Heading |
|---|---|
| 571 | X is —CH═CH—, $R^1$ is Pr, $R^2$ is I, and Pyr is 2-pyridinyl. |
| 572 | X is —CH═CH—, $R^1$ is Pr, $R^2$ is I, and Pyr is 3-pyridinyl. |
| 573 | X is —CH═CH—, $R^1$ is Pr, $R^2$ is I, and Pyr is 4-pyridinyl. |
| 574 | X is —CH═CH—, $R^1$ is Pr, $R^2$ is I, and Pyr is 2-pyridinyl(3-$CH_3$). |
| 575 | X is —CH═CH—, $R^1$ is Pr, $R^2$ is I, and Pyr is 2-pyridinyl(4-$CH_3$). |
| 576 | X is —CH═CH—, $R^1$ is Pr, $R^2$ is I, and Pyr is 3-pyridinyl(2-$CH_3$). |
| 577 | X is —CH═CH—, $R^1$ is Pr, $R^2$ is I, and Pyr is 3-pyridinyl(4-$CH_3$). |
| 578 | X is —CH═CH—, $R^1$ is Pr, $R^2$ is I, and Pyr is 2-pyridinyl(3-Cl). |
| 579 | X is —CH═CH—, $R^1$ is Pr, $R^2$ is I, and Pyr is 2-pyridinyl(4-Cl). |
| 580 | X is —CH═CH—, $R^1$ is Pr, $R^2$ is I, and Pyr is 3-pyridinyl(5-Cl). |
| 581 | X is —CH═CH—, $R^1$ is Pr, $R^2$ is OMe, and Pyr is 2-pyridinyl. |
| 582 | X is —CH═CH—, $R^1$ is Pr, $R^2$ is OMe, and Pyr is 3-pyridinyl. |
| 583 | X is —CH═CH—, $R^1$ is Pr, $R^2$ is OMe, and Pyr is 4-pyridinyl. |
| 584 | X is —CH═CH—, $R^1$ is Pr, $R^2$ is OMe, and Pyr is 2-pyridinyl(3-$CH_3$). |
| 585 | X is —CH═CH—, $R^1$ is Pr, $R^2$ is OMe, and Pyr is 2-pyridinyl(4-$CH_3$). |
| 586 | X is —CH═CH—, $R^1$ is Pr, $R^2$ is OMe, and Pyr is 3-pyridinyl(2-$CH_3$). |
| 587 | X is —CH═CH—, $R^1$ is Pr, $R^2$ is OMe, and Pyr is 3-pyridinyl(4-$CH_3$). |
| 588 | X is —CH═CH—, $R^1$ is Pr, $R^2$ is OMe, and Pyr is 2-pyridinyl(3-Cl). |
| 589 | X is —CH═CH—, $R^1$ is Pr, $R^2$ is OMe, and Pyr is 2-pyridinyl(4-Cl). |
| 590 | X is —CH═CH—, $R^1$ is Pr, $R^2$ is OMe, and Pyr is 3-pyridinyl(5-Cl). |
| 591 | X is —CH═CH—, $R^1$ is Pr, $R^2$ is OEt, and Pyr is 2-pyridinyl. |
| 592 | X is —CH═CH—, $R^1$ is Pr, $R^2$ is OEt, and Pyr is 3-pyridinyl. |
| 593 | X is —CH═CH—, $R^1$ is Pr, $R^2$ is OEt, and Pyr is 4-pyridinyl. |
| 594 | X is —CH═CH—, $R^1$ is Pr, $R^2$ is OEt, and Pyr is 2-pyridinyl(3-$CH_3$). |
| 595 | X is —CH═CH—, $R^1$ is Pr, $R^2$ is OEt, and Pyr is 2-pyridinyl(4-$CH_3$). |
| 596 | X is —CH═CH—, $R^1$ is Pr, $R^2$ is OEt, and Pyr is 3-pyridinyl(2-$CH_3$). |
| 597 | X is —CH═CH—, $R^1$ is Pr, $R^2$ is OEt, and Pyr is 3-pyridinyl(4-$CH_3$). |
| 598 | X is —CH═CH—, $R^1$ is Pr, $R^2$ is OEt, and Pyr is 2-pyridinyl(3-Cl). |
| 599 | X is —CH═CH—, $R^1$ is Pr, $R^2$ is OEt, and Pyr is 2-pyridinyl(4-Cl). |
| 600 | X is —CH═CH—, $R^1$ is Pr, $R^2$ is OEt, and Pyr is 3-pyridinyl(5-Cl). |
| 601 | X is S, $R^1$ is $CH_2CF_3$, $R^2$ is Me, and Pyr is 2-pyridinyl. |
| 602 | X is S, $R^1$ is $CH_2CF_3$, $R^2$ is Me, and Pyr is 3-pyridinyl. |
| 603 | X is S, $R^1$ is $CH_2CF_3$, $R^2$ is Br, and Pyr is 2-pyridinyl. |
| 604 | X is S, $R^1$ is $CH_2CF_3$, $R^2$ is Br, and Pyr is 3-pyridinyl. |
| 605 | X is S, $R^1$ is $CH_2CH_2CN$, $R^2$ is Me, and Pyr is 2-pyridinyl. |
| 606 | X is S, $R^1$ is $CH_2CH_2CN$, $R^2$ is Me, and Pyr is 3-pyridinyl. |
| 607 | X is S, $R^1$ is $CH_2CH_2CN$, $R^2$ is Br, and Pyr is 2-pyridinyl. |
| 608 | X is S, $R^1$ is $CH_2CH_2CN$, $R^2$ is Br, and Pyr is 3-pyridinyl. |
| 609 | X is —CH═CH—, $R^1$ is $CH_2CF_3$, $R^2$ is Me, and Pyr is 2-pyridinyl. |
| 610 | X is —CH═CH—, $R^1$ is $CH_2CF_3$, $R^2$ is Me, and Pyr is 3-pyridinyl. |
| 611 | X is —CH═CH—, $R^1$ is $CH_2CF_3$, $R^2$ is Br, and Pyr is 2-pyridinyl. |
| 612 | X is —CH═CH—, $R^1$ is $CH_2CF_3$, $R^2$ is Br, and Pyr is 3-pyridinyl. |
| 613 | X is —CH═CH—, $R^1$ is $CH_2CH_2CN$, $R^2$ is Me, and Pyr is 2-pyridinyl. |
| 614 | X is —CH═CH—, $R^1$ is $CH_2CH_2CN$, $R^2$ is Me, and Pyr is 3-pyridinyl. |
| 615 | X is —CH═CH—, $R^1$ is $CH_2CH_2CN$, $R^2$ is Br, and Pyr is 2-pyridinyl. |
| 616 | X is —CH═CH—, $R^1$ is $CH_2CH_2CN$, $R^2$ is Br, and Pyr is 3-pyridinyl. |
| 617 | X is O, $R^1$ is Me, $R^2$ is Me, and Pyr is 2-pyridinyl. |
| 618 | X is O, $R^1$ is Me, $R^2$ is Me, and Pyr is 3-pyridinyl(2-$CH_3$). |
| 619 | X is O, $R^1$ is Me, $R^2$ is Br, and Pyr is 2-pyridinyl. |
| 620 | X is O, $R^1$ is Me, $R^2$ is Br, and Pyr is 3-pyridinyl(2-$CH_3$). |
| 621 | X is —CH═C(Me)—, $R^1$ is Me, $R^2$ is Me, and Pyr is 2-pyridinyl. |
| 622 | X is —CH═C(Me)—, $R^1$ is Me, $R^2$ is Me, and Pyr is 3-pyridinyl(2-$CH_3$). |
| 623 | X is —CH═C(Me)—, $R^1$ is Me, $R^2$ is Br, and Pyr is 2-pyridinyl. |
| 624 | X is —CH═C(Me)—, $R^1$ is Me, $R^2$ is Br, and Pyr is 3-pyridinyl(2-$CH_3$). |
| 625 | X is N(Me), $R^1$ is Me, $R^2$ is Me, and Pyr is 2-pyridinyl. |
| 626 | X is N(Me), $R^1$ is Me, $R^2$ is Me, and Pyr is 3-pyridinyl. |
| 627 | X is N(Me), $R^1$ is Me, $R^2$ is Br, and Pyr is 2-pyridinyl. |
| 628 | X is N(Me), $R^1$ is Me, $R^2$ is Br, and Pyr is 3-pyridinyl. |
| 629 | X is —CH═C(F)—, $R^1$ is Me, $R^2$ is Me, and Pyr is 2-pyridinyl. |
| 630 | X is —CH═C(F)—, $R^1$ is Me, $R^2$ is Me, and Pyr is 3-pyridinyl. |
| 631 | X is —CH═C(F)—, $R^1$ is Me, $R^2$ is Br, and Pyr is 2-pyridinyl. |
| 632 | X is —CH═C(F)—, $R^1$ is Me, $R^2$ is Br, and Pyr is 3-pyridinyl. |
| 632 | X is —CH═C(Cl)—, $R^1$ is Me, $R^2$ is Me, and Pyr is 2-pyridinyl. |
| 633 | X is —CH═C(Cl)—, $R^1$ is Me, $R^2$ is Me, and Pyr is 3-pyridinyl. |
| 634 | X is —CH═C(Cl)—, $R^1$ is Me, $R^2$ is Br, and Pyr is 2-pyridinyl. |
| 635 | X is —CH═C(Cl)—, $R^1$ is Me, $R^2$ is Br, and Pyr is 3-pyridinyl. |
| 636 | X is —CH═C(OMe)—, $R^1$ is Me, $R^2$ is Me, and Pyr is 2-pyridinyl. |
| 637 | X is —CH═C(OMe)—, $R^1$ is Me, $R^2$ is Me, and Pyr is 3-pyridinyl. |
| 638 | X is —CH═C(OMe)—, $R^1$ is Me, $R^2$ is Br, and Pyr is 2-pyridinyl. |
| 639 | X is —CH═C(OMe)—, $R^1$ is Me, $R^2$ is Br, and Pyr is 3-pyridinyl. |
| 640 | X is —CH═C(CN)—, $R^1$ is Me, $R^2$ is Me, and Pyr is 2-pyridinyl. |
| 641 | X is —CH═C(CN)—, $R^1$ is Me, $R^2$ is Me, and Pyr is 3-pyridinyl. |
| 642 | X is —CH═C(CN)—, $R^1$ is Me, $R^2$ is Br, and Pyr is 2-pyridinyl. |
| 643 | X is —CH═C(CN)—, $R^1$ is Me, $R^2$ is Br, and Pyr is 3-pyridinyl. |

TABLE 644

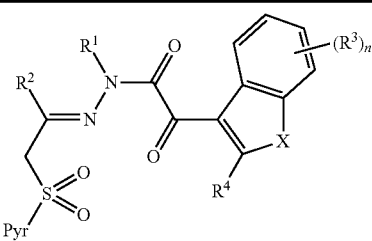

Table 644 is constructed the same as Table 1 except that the structure in Table 1 is replaced with the structure above for Table 644.

Table 645 Through Table 1288

Table 645 is constructed the same as Table 2 except that the structure in Table 2 is replaced with the structure above for Table 644. Tables 646 through 1288 are constructed in the same fashion as Tables 3 through 644.

TABLE 1289

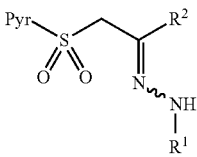

Pyr is 2-pyridinyl

| $R^1$ | $R^2$ |
|---|---|
| $CH_3$ | $CH_3$ |
| $CH_2CH_3$ | $CH_3$ |
| $CH_3$ | $CH_2CH_3$ |

This disclosure also includes the compounds described in Tables 1289A through 1289I where the header row of Table 1289 (i.e. Pyr is 2-pyridinyl) is replaced with the Header Row listed for each Table below.

| Table | Header Row |
|---|---|
| 1289A | Pyr is 3-pyridinyl. |
| 1289B | Pyr is 4-pyridinyl. |
| 1289C | Pyr is 2-pyridinyl(3-$CH_3$). |
| 1289D | Pyr is 2-pyridinyl(4-$CH_3$). |
| 1289E | Pyr is 3-pyridinyl(2-$CH_3$). |
| 1289F | Pyr is 3-pyridinyl(4-$CH_3$). |
| 1289G | Pyr is 2-pyridinyl(3-Cl). |
| 1289H | Pyr is 2-pyridinyl(4-Cl). |
| 1289I | Pyr is 3-pyridinyl(5-Cl). |

TABLE 1290

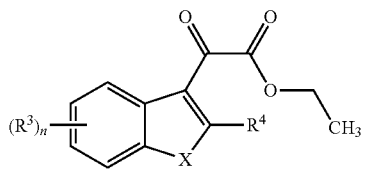

| X is S, $R^1$ is Me, and $R^2$ is Me. | | | | | |
|---|---|---|---|---|---|
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is S, $R^1$ is Me, and $R^2$ is Et. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is S, $R^1$ is Et, and $R^2$ is Me. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is S, $R^1$ is Et, and $R^2$ is Et. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is —CH=CH—, $R^1$ is Me, and $R^2$ is Me. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is —CH=CH—, $R^1$ is Me, and $R^2$ is Et. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is —CH=CH—, $R^1$ is Et, and $R^2$ is Me. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is —CH=CH—, $R^1$ is Et, and $R^2$ is Et. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is —CH=CCl—, $R^1$ is Et, and $R^2$ is Me. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |
| X is —CH=CCl—, $R^1$ is Et, and $R^2$ is Et. | | | | | |
| $(R^3)_n$ | $R^4$ | $(R^3)_n$ | $R^4$ | $(R^3)_n$ | $R^4$ |
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |

TABLE 1290-continued

X is —CH=CF—, R¹ is Me, and R² is Me.

| $(R^3)_n$ | $R^4$ | $(R^3)_n$ | $R^4$ | $(R^3)_n$ | $R^4$ |
|---|---|---|---|---|---|
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |

X is —CH=CF—, R¹ is Me, and R² is Et.

| $(R^3)_n$ | $R^4$ | $(R^3)_n$ | $R^4$ | $(R^3)_n$ | $R^4$ |
|---|---|---|---|---|---|
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |

X is —CH=CF—, R¹ is Et, and R² is Me.

| $(R^3)_n$ | $R^4$ | $(R^3)_n$ | $R^4$ | $(R^3)_n$ | $R^4$ |
|---|---|---|---|---|---|
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |

X is —CH=CF—, R¹ is Et, and R² is Et.

| $(R^3)_n$ | $R^4$ | $(R^3)_n$ | $R^4$ | $(R^3)_n$ | $R^4$ |
|---|---|---|---|---|---|
| — | H | — | Me | — | Et |
| 5-Me | H | 5-Me | Me | 5-Me | Et |
| 4,6-di-Me | H | 4,6-di-Me | Me | 4,6-di-Me | Et |
| 5,7-di-Me | H | 5,7-di-Me | Me | 5,7-di-Me | Et |

TABLE 1291

Table 1291 is constructed the same way as Table 1290 except the structure is replaced with

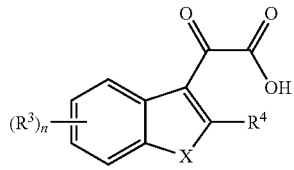

TABLE 1292

Table 1292 is constructed the same way as Table 1291 except the structure is replaced with

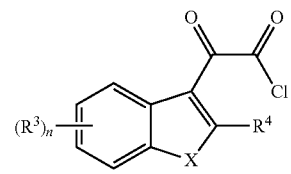

TABLE 1293

Pyr is 2-pyridinyl

| $R^2$ |
|---|
| $CH_3$(**) |
| $CH_2CH_3$ |

**See Synthesis Example 1, Step A for ¹H NMR

This disclosure also includes the compounds listed in Tables 1293A through 1293I where the Header Row of Table 1293 (i.e. Pyr is 2-pyridinyl) is replaced with the Header Row listed for each Table below.

| Table | Header Row |
|---|---|
| 1293A | Pyr is 3-pyridinyl. |
| 1293B | Pyr is 4-pyridinyl. |
| 1293C | Pyr is 2-pyridinyl(3-$CH_3$). |
| 1293D | Pyr is 2-pyridinyl(4-$CH_3$). |
| 1293E | Pyr is 3-pyridinyl(2-$CH_3$). |
| 1293F | Pyr is 3-pyridinyl(4-$CH_3$). |
| 1293G | Pyr is 2-pyridinyl(3-Cl). |
| 1293H | Pyr is 2-pyridinyl(4-Cl). |
| 1293I | Pyr is 3-pyridinyl(5-Cl). |

TABLE 1294

Pyr is 2-pyridyl

| $R^2$ |
|---|
| $CH_3$ |
| $CH_2CH_3$ |

This disclosure also includes the compounds listed in Tables 1294A through 1294I where the Header Row of Table 1294 is replaced with the Header Row listed for each Table below.

| Table | Header Row |
|---|---|
| 1294A | Pyr is 3-pyridinyl. |
| 1294B | Pyr is 4-pyridinyl. |
| 1294C | Pyr is 2-pyridinyl(3-$CH_3$). |
| 1294D | Pyr is 2-pyridinyl(4-$CH_3$). |
| 1294E | Pyr is 3-pyridinyl(2-$CH_3$). |
| 1294F | Pyr is 3-pyridinyl(4-$CH_3$). |
| 1294G | Pyr is 2-pyridinyl(3-Cl). |
| 1294H | Pyr is 2-pyridinyl(4-Cl). |
| 1294I | Pyr is 3-pyridinyl(5-Cl). |

The following abbreviations are used in the Index Table which follows: Me is methyl, "Cmpd. No." is "Compound Number", "Ex." is "Example" and is followed by a number indicating in which example the compound is prepared.

INDEX TABLE A

| Cmpd. No. | R¹ | R² | (R³)ₙ | R⁴ | X | Pyr | NMR |
|---|---|---|---|---|---|---|---|
| 1 (Ex. 1) | Me | Me | — | | —CH=CF— | 2-pyridinyl | * |
| 2 (Ex. 2) | Me | Me | 5-Me | Me | S | 2-pyridinyl | ** |

\* See Synthesis Example for ¹H NMR data.

INDEX TABLE B

| Cmpd. No. | R¹ | R² | Pyr | NMR |
|---|---|---|---|---|
| 3 (Ex. 1) | Me | Me | 2-pyridinyl | * |

\* See Synthesis Example for ¹H NMR data.

What is claimed is:

1. A herbicide intermediate compound of Formula 2 wherein
R¹ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_1$-$C_7$ haloalkyl, $C_3$-$C_7$ haloalkenyl, $C_2$-$C_7$ alkoxyalkyl or $C_3$-$C_7$ alkylthioalkyl;
R² is $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl or $C_2$-$C_3$ alkoxycarbonyl; or phenyl optionally substituted by halogen, $C_1$-$C_4$ alkyl or $C_1$-$C_4$ haloalkyl;
X is O or S; or
X is —C(R⁶)=C(R⁷)—, wherein the carbon atom bonded to R⁶ is also bonded to the carbon atom bonded to R⁴, and the carbon atom bonded to R⁷ is also bonded to the phenyl ring moiety in Formula 2;
each R³ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;
n is 0, 1 or 2;
R⁴, R⁶ and R⁷ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl; and
Pyr is a pyridine ring optionally substituted with halogen or $C_1$-$C_4$ alkyl.

2. The herbicide intermediate compound of claim 1 wherein
R¹ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_1$-$C_7$ haloalkyl, $C_2$-$C_7$ alkoxyalkyl or $C_3$-$C_7$ alkylthioalkyl;
R² is $C_1$-$C_7$ alkyl, $C_3$-$C_7$ cycloalkyl, $C_4$-$C_7$ cycloalkylalkyl, $C_1$-$C_7$ haloalkyl or $C_2$-$C_7$ alkoxyalkyl;
each R³ is independently halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy, $C_1$-$C_5$ haloalkoxy or $C_1$-$C_5$ alkylthio;
R⁴, R⁶ and R⁷ are independently H, halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy or $C_1$-$C_5$ alkylthio; and
Pyr is a pyridine ring optionally substituted with F, Cl, Br or CH₃.

3. The herbicide intermediate compound of claim 2 wherein
R¹ is H, $C_1$-$C_7$ alkyl, $C_3$-$C_7$ alkenyl, $C_3$-$C_7$ alkynyl, $C_3$-$C_7$ cycloalkyl or $C_4$-$C_7$ cycloalkylalkyl;
R² is $C_1$-$C_7$ alkyl, $C_3$-$C_7$ cycloalkyl, $C_4$-$C_7$ cycloalkylalkyl or $C_2$-$C_7$ alkoxyalkyl;
X is S; or
X is —C(R⁶)=C(R⁷)—, wherein the carbon atom bonded to R⁶ is also bonded to the carbon atom bonded to R⁴, and the carbon atom bonded to R⁷ is also bonded to the phenyl ring moiety in Formula 2;
each R³ is independently halogen, $C_1$-$C_5$ alkyl, $C_3$-$C_5$ cycloalkyl or $C_1$-$C_5$ alkoxy;
R⁴, R⁶ and R⁷ are independently H, halogen, $C_1$-$C_5$ alkyl or $C_1$-$C_5$ alkoxy; and
Pyr is a 2-pyridinyl ring optionally substituted with F, Cl, Br or CH₃.

4. The herbicide intermediate compound of claim 3 wherein
R¹ is H or $C_1$-$C_7$ alkyl;
R² is $C_1$-$C_7$ alkyl or $C_3$-$C_7$ cycloalkyl;
X is S;
each R³ is independently halogen $C_1$-$C_5$ alkyl or $C_1$-$C_5$ alkoxy;
R⁴ is H, halogen or $C_1$-$C_5$ alkyl; and
Pyr is an unsubstituted 2-pyridinyl ring.

5. The herbicide intermediate compound of claim 3 wherein
R¹ is H or $C_1$-$C_7$ alkyl;
R² is $C_1$-$C_7$ alkyl or $C_3$-$C_7$ cycloalkyl;
X is —C(R⁶)=C(R⁷)—, wherein the carbon atom bonded to R⁶ is also bonded to the carbon atom bonded to R⁴, and the carbon atom bonded to $R^7$ is also bonded to the phenyl ring moiety in Formula 2;

each $R^3$ is independently halogen, $C_1$-$C_5$ alkyl or $C_1$-$C_5$ alkoxy;

$R^4$, $R^6$ and $R^7$ are independently H, halogen or $C_1$-$C_5$ alkyl; and

Pyr is an unsubstituted 2-pyridinyl ring.

6. A process for preparing the herbicide intermediate compound of Formula 2

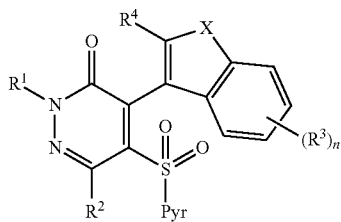

2 wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, nitroalkyl, $C_1$-$C_7$ haloalkyl, $C_3$-$C_7$ haloalkenyl, $C_2$-$C_7$ alkoxyalkyl or $C_3$-$C_7$ alkylthioalkyl;

$R^2$ is $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl or $C_2$-$C_3$ alkoxycarbonyl; or phenyl optionally substituted by halogen, $C_1$-$C_4$ alkyl or $C_1$-$C_4$ haloalkyl;

X is O or S; or
X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 2;

each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

n is 0, 1 or 2;

$R^4$, $R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, alkylsulfinyl, alkylsulfonyl, $C_1$-$C_5$ haloalkylthio or $C_2$-$C_5$ alkoxycarbonyl; and Pyr is a pyridine ring optionally substituted with halogen or alkyl;

comprising cyclizing the product of the reaction between a herbicide intermediate compound of Formula 4

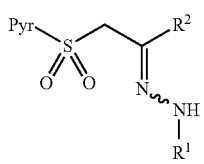

4 wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_1$-$C_7$ haloalkyl, $C_3$-$C_7$ haloalkenyl, $C_2$-$C_7$ alkoxyalkyl or $C_3$-$C_7$ alkylthioalkyl;

$R^2$ is $C_1$-$C_7$ alkyl, $C_3$-$C_8$ alkylcarbonylalkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_2$-$C_3$ cyanoalkyl, $C_1$-$C_4$ nitroalkyl, $C_2$-$C_7$ haloalkoxyalkyl, $C_1$-$C_7$ haloalkyl, $C_3$-$C_7$ haloalkenyl, $C_2$-$C_7$ alkoxyalkyl or $C_2$-$C_3$ alkoxycarbonyl; or phenyl optionally substituted by halogen, $C_1$-$C_4$ alkyl or $C_1$-$C_4$ haloalkyl; and Pyr is a pyridine ring optionally substituted with halogen or $C_1$-$C_4$ alkyl;

with a compound of Formula 3

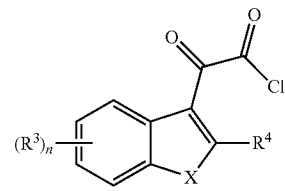

3 wherein
X is O or S; or
X is —C($R^6$)=C($R^7$)—, wherein the carbon atom bonded to $R^6$ is also bonded to the carbon atom bonded to $R^4$, and the carbon atom bonded to $R^7$ is also bonded to the phenyl ring moiety in Formula 3;

each $R^3$ is independently halogen, —CN, nitro, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxyalkyl, $C_1$-$C_5$ alkoxy, $C_1$-$C_5$ haloalkoxy, $C_1$-$C_5$ alkylthio, $C_1$-$C_5$ haloalkylthio or $C_2$-$C_5$ alkoxycarbonyl;

n is 0, 1 or 2; and $R^4$, $R^6$ and $R^7$ are independently H, halogen, nitro, —CN, $C_1$-$C_5$ alkyl, $C_2$-$C_5$ alkenyl, $C_2$-$C_5$ alkynyl, $C_3$-$C_5$ cycloalkyl, $C_4$-$C_5$ cycloalkylalkyl, $C_1$-$C_5$ haloalkyl, $C_3$-$C_5$ haloalkenyl, $C_3$-$C_5$ haloalkynyl, $C_2$-$C_5$ alkoxy-alkyl, $C_1$-$C_5$ alkoxy, $C_1$-$C_5$ haloalkoxy, $C_1$-$C_5$ alkylthio, $C_1$-$C_4$ alkylsulfinyl, $C_1$-$C_4$ alkylsulfonyl, $C_1$-$C_5$ haloalkylthio or $C_2$-$C_5$ alkoxycarbonyl.

7. The process of claim 6 wherein
$R^1$ is H, $C_1$-$C_7$ alkyl, $C_3$-$C_8$ alkoxycarbonylalkyl, $C_4$-$C_7$ alkylcycloalkyl, $C_3$-$C_7$ alkenyl, $C_3$-$C_7$ alkynyl, $C_3$-$C_7$ cycloalkyl, $C_4$-$C_7$ cycloalkylalkyl, $C_1$-$C_7$ haloalkyl, $C_2$-$C_7$ alkoxyalkyl or $C_3$-$C_7$ alkylthioalkyl;

$R^2$ is $C_1$-$C_7$ alkyl, $C_3$-$C_7$ cycloalkyl, $C_4$-$C_7$ cycloalkylalkyl, $C_1$-$C_7$ haloalkyl or $C_2$-$C_7$ alkoxyalkyl;

each $R^3$ is independently halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy, $C_1$-$C_5$ haloalkoxy or $C_1$-$C_5$ alkylthio;

$R^4$, $R^6$ and $R^7$ are independently H, halogen, $C_1$-$C_5$ alkyl, $C_3$-$C_5$ cycloalkyl, $C_4$-$C_5$ cycloalkylalkyl, $C_1$-$C_5$ haloalkyl, $C_2$-$C_5$ alkoxyalkyl, $C_1$-$C_5$ alkoxy or $C_1$-$C_5$ alkylthio; and Pyr is a pyridine ring optionally substituted with F, Cl, Br or $CH_3$.

8. The process of claim 6 wherein
$R^1$ is H, $C_1$-$C_7$ alkyl, $C_3$-$C_7$ alkenyl, $C_3$-$C_7$ alkynyl, $C_3$-$C_7$ cycloalkyl or $C_4$-$C_7$ cycloalkylalkyl;
$R^2$ is $C_1$-$C_7$ alkyl, $C_3$-$C_7$ cycloalkyl, $C_4$-$C_7$ cycloalkylalkyl or $C_2$-$C_7$ alkoxyalkyl;
X is S; or
X is —$C(R^6)$=$C(R^7)$—, wherein the carbon atom bonded to $R^6$ is also bonded to the carbon atom bonded to $R^4$, and the carbon atom bonded to $R^7$ is also bonded to the phenyl ring moiety in Formula 2;
each $R^3$ is independently halogen, $C_1$-$C_5$ alkyl, $C_3$-$C_5$ cycloalkyl or $C_1$-$C_5$ alkoxy;
$R^4$, $R^6$ and $R^7$ are independently H, halogen, $C_1$-$C_5$ alkyl or $C_1$-$C_5$ alkoxy; and
Pyr is a 2-pyridinyl ring optionally substituted with F, Cl, Br or $CH_3$.

9. The process of claim 6 wherein
$R^1$ is H or $C_1$-$C_7$ alkyl;
$R^2$ is $C_1$-$C_7$ alkyl or $C_3$-$C_7$ cycloalkyl;
X is S;
each $R^3$ is independently halogen $C_1$-$C_5$ alkyl or $C_1$-$C_5$ alkoxy;
$R^4$ is H, halogen or $C_1$-$C_5$ alkyl; and
Pyr is an unsubstituted 2-pyridinyl ring.

10. The process of claim 6 wherein
$R^1$ is H or $C_1$-$C_7$ alkyl;
$R^2$ is $C_1$-$C_7$ alkyl or $C_3$-$C_7$ cycloalkyl;
X is —$C(R^6)$=$C(R^7)$—, wherein the carbon atom bonded to $R^6$ is also bonded to the carbon atom bonded to $R^4$, and the carbon atom bonded to $R^7$ is also bonded to the phenyl ring moiety in Formula 2;
each $R^3$ is independently halogen, $C_1$-$C_5$ alkyl or $C_1$-$C_5$ alkoxy;
$R^4$, $R^6$ and $R^7$ are independently H, halogen or $C_1$-$C_5$ alkyl; and
Pyr is an unsubstituted 2-pyridinyl ring.

* * * * *